United States Patent [19]
Dijcks et al.

[11] Patent Number: 6,080,773
[45] Date of Patent: Jun. 27, 2000

[54] BENZYLAMINE DERIVATIVES WHICH ARE USEFUL IN TREATING PSYCHIATRIC DISORDERS

[75] Inventors: Fredericus Antonius Dijcks, Oss, Netherlands; Dirk Leysen, Lommel, Belgium; Joannes Theodorus Maria Linders; Gerardus Stephanus Franciscus Ruigt, both of Oss, Netherlands; Ian Craig Carlyle, Hamilton-Lanarlshire, United Kingdom; Simon James Anthony Grove, Glasgow, United Kingdom; Duncan Robertson Rae, Lanarkshire, United Kingdom; Simon N. Thorn, Kirknewton, United Kingdom

[73] Assignee: Akzo Nobel, N.V., Arnhem, Netherlands

[21] Appl. No.: 08/950,359

[22] Filed: Oct. 14, 1997

[51] Int. Cl.[7] .......................... A61K 31/42; A61K 31/415; C07D 261/20; C07D 231/56
[52] U.S. Cl. ..................... 514/379; 514/403; 514/406; 548/241; 548/361.1; 548/362.5
[58] Field of Search ............................ 548/241, 361.1, 548/362.5; 514/379, 403, 406

[56] References Cited

U.S. PATENT DOCUMENTS 5,552,412  9/1996  Cameron et al. ........................ 514/317

*Primary Examiner*—Laura L. Stockton
*Attorney, Agent, or Firm*—Mary E. Gormley

[57] ABSTRACT

The present invention relates to certain novel benzylamine derivatives, to processes for their preparation, to pharmaceutical formulations containing them and to their use in medical therapy, particularly in the treatment of depression.

8 Claims, No Drawings

BENZYLAMINE DERIVATIVES WHICH ARE USEFUL IN TREATING PSYCHIATRIC DISORDERS

The present invention relates to certain novel benzylamine derivatives, to processes for their preparation, to pharmaceutical formulations containing them and to their use in medical therapy, particularly in the treatment of depression.

European patent specification No.0 299 349 discloses certain propyl-1,2-benzisoxazole derivatives having analgesic and hypotensive activity. A number of arylethylamine derivatives which are useful in treating or in preventing a disorder of the melatoninergic system are disclosed in U.S. Pat. No. 5,276,051.

A group of benzylamine derivatives have now been found which show activity as antidepressants and are useful in treating a number of other conditions described herein. Thus, according to one aspect, the present invention provides the compounds of formula (I)

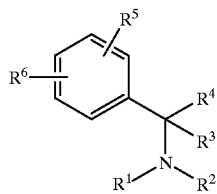

(I)

wherein $R^1$ and $R^2$, which may be the same or different, are each selected from $C_{6-12}$aryl, $C_{2-14}$heteroaryl, $C_{6-12}$aryl$C_{1-6}$alkyl, $C_{2-14}$heteroaryl$C_{1-6}$alkyl (where the alkyl, aryl or heteroaryl moiety may be optionally substituted by one or more substituents selected from $C_{1-6}$alkoxy, $C_{1-6}$alkyl, $C_{3-6}$cycloalkyl, $C_{4-6}$cycloalkenyl, $C_{6-12}$aryl, $C_{2-14}$heteroaryl, halogen, amino, hydroxy, halo$C_{1-6}$alkyl, nitro, $C_{1-6}$alkylthio, sulphonamide, $C_{1-6}$alkylsulphonyl, hydroxy$C_{1-6}$alkyl, $C_{1-6}$alkoxycarbonyl, carboxyl, carboxy$C_{1-6}$alkyl, carboxamide and $C_{1-6}$alkylcarboxamide), hydrogen, $C_{1-6}$alkyl, $C_{3-6}$cycloalkyl, $C_{3-6}$cycloalkyl-$C_{1-6}$alkyl, $C_{4-6}$cycloalkenyl, $C_{2-6}$alkenyl, $C_{2-6}$alkynyl and $C_{1-6}$alkoxy$C_{1-6}$alkyl (where the alkyl, cycloalkyl, cycloalkenyl, alkenyl, alkynyl, or alkoxyalkyl moieties may be optionally substituted by one or more substituents selected from amino, halogen, hydroxy, $C_{1-6}$alkylcarboxamide, carboxamide, carboxy, $C_{1-6}$alkoxycarbonyl, $C_{1-6}$alkylcarboxy and carboxy$C_{1-6}$alkyl) or one of $R^1$ and $R^2$ are as hereinbefore defined and one is hydroxy;

$R^3$ and $R^4$, which may be the same or different, are each selected from $C_{6-12}$aryl, $C_{2-14}$heteroaryl, $C_{6-12}$aryl$C_{1-6}$alkyl, $C_{2-14}$heteroaryl$C_{1-6}$alkyl (where the alkyl, aryl or heteroaryl moiety may be optionally substituted by one or more substituents selected from $C_{1-6}$alkoxy, $C_{1-6}$alkyl, $C_{3-6}$cycloalkyl, $C_{4-6}$cycloalkenyl, $C_{6-12}$aryl, $C_{2-14}$heteroaryl, halogen, amino, hydroxy, halo$C_{1-6}$alkyl, nitro, $C_{1-6}$alkylthio, sulphonamide, $C_{1-6}$alkylsulphonyl, hydroxy $C_{1-6}$alkyl, $C_{1-6}$alkoxycarbonyl, carboxyl, carboxy$C_{1-6}$alkyl, $C_{1-6}$alkylcarboxamide and carboxamide), hydrogen, $C_{1-6}$alkyl, $C_{3-6}$cycloalkyl, $C_{3-6}$cycloalkyl$C_{1-6}$alkyl, $C_{4-6}$cycloalkenyl, $C_{2-6}$alkenyl, $C_{2-6}$alkynyl, $C_{1-6}$alkoxy$C_{1-6}$alkyl, halo$C_{1-6}$alkyl, halo$C_{2-6}$alkenyl, halo$C_{2-6}$alkynyl, cyano, carboxyl, $C_{1-6}$alkylcarboxy and carboxy$C_{1-6}$alkyl (where the alkyl, cycloalkyl, cycloalkenyl, alkenyl, alkynyl, or alkoxyalkyl moieties may be optionally substituted by one or more substituents selected from amino, hydroxy, $C_{1-6}$alkylcarboxamide, carboxamide, carboxy, $C_{1-6}$alkoxycarbonyl, $C_{1-6}$alkylcarboxy and carboxy$C_{1-6}$alkyl); or one of $R^3$ or $R^4$ together with one of $R^1$ or $R^2$ and the N atom to which it is attached form a 5- or 6-membered heterocyclic ring.

$R^5$ represents one or more ring substituents selected from halogen, hydrogen $C_{1}$6alkyl and $C_{1-6}$alkoxy; and $R^6$ represents a single ring substituent of formula:

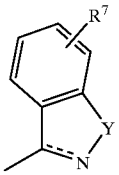

wherein the dotted line represents an optional bond; Y is oxygen or —NR$^8$ (where R$^8$ is hydrogen or $C_{1-6}$alkyl) and $R^7$ represents one or more substituents selected from hydrogen, halogen, halo$C_{1-6}$alkyl, $C_{1-6}$alkyl and $C_{1-6}$alkoxy; or a pharmaceutically acceptable salt or solvate thereof.

The present invention further includes the compounds of formula (I) wherein:

1. One of $R^1$ and $R^2$ is hydrogen and the other is $C_{6-12}$aryl$C_{1-6}$alkyl, $C_{2-14}$heteroaryl$C_{1-6}$alkyl(where the alkyl, aryl or heteroaryl moiety may be optionally substituted by one or more ring substituents selected from $C_{1-6}$alkoxy, $C_{2-14}$heteroaryl, and carboxamide), hydrogen, $C_{1-6}$alkyl, $C_{2-6}$alkenyl and hydroxy; or a pharmaceutically acceptable salt or solvate thereof.

2. One of $R^1$ and $R^2$ is hydrogen and the other is $C_{6-12}$aryl$C_{1-6}$alkyl, $C_{2-14}$heteroaryl$C_{1-6}$alkyl(where the alkyl, aryl or heteroaryl moiety may be optionally substituted by one or more ring substituents selected from $C_{1-6}$alkoxy, $C_{2-14}$heteroaryl, $C_{1-6}$alkylcarboxamide and carboxamide), hydrogen, $C_{1-6}$alkyl, $C_{2-6}$alkenyl and hydroxy where the alkyl or alkenyl, moieties may be optionally substituted by one or more substituents selected from hydroxy, $C_{1-6}$alkylcarboxy and carboxy$C_{1-6}$alkyl); or a pharmaceutically acceptable salt or solvate thereof.

3. $R^1$ and $R^2$ are both $C_{1-6}$alkyl.

4. One of $R^3$ and $R^4$ is hydrogen and the other is $C_{6-12}$aryl$C_{1-6}$alkyl, hydrogen, $C_{1-6}$alkyl, $C_{2-6}$alkenyl, $C_{2-6}$alkynyl, cyano; or a pharmaceutically acceptable salt or solvate thereof.

5. One of $R^3$ and $R^4$ is hydrogen and the other is $C_{6-12}$aryl, $C_{6-12}$aryl$C_{1-6}$alkyl (where the aryl moiety may be optionally substituted by halogen), $C_{1-6}$alkylcarboxy, halo$C_{1-6}$alkyl, halo$C_{2-6}$alkenyl, $C_{3-6}$cycloalkyl$C_{1-6}$alkyl, $C_{4-6}$cycloalkenyl, $C_{2-14}$heteroaryl$C_{1-6}$alkyl 6. $R^6$ is in the ortho position.

7. $R^6$ is in the meta or para positions.

8. Y is oxygen or —NCH$_3$, $R^7$ is hydrogen and the dotted line represents a bond.

9. $R^7$ is halogen, halo$C_{1-6}$alkyl

10. $R^1$,$R^2$,$R^3$,$R^4$, $R^5$,$R^6$,$R^7$,Y and the dotted line are as defined in points 1 to 9 supra,; or a pharmaceutically acceptable salt or solvate thereof.

The present invention further provides the compounds of formula (I) wherein $R^1$, $R^2$, $R^5$ and $R^6$ are as defined in relation to formula (I) supra, $R^3$ and $R^4$, which may be the same or different, are each selected from $C_{6-12}$aryl, $C_{2-14}$heteroaryl, $C_{6-12}$aryl$C_{1-6}$alkyl, $C_{2-14}$heteroaryl$C_{1-}$ 6alkyl (where the alkyl, aryl or heteroaryl moiety may be optionally substituted by one or more substituents selected from $C_{1-6}$alkoxy, $C_{1-6}$alkyl, $C_{3-6}$cycloalkyl, $C_{4-6}$cycloalkenyl, $C_{6-12}$aryl, $C_{2-14}$heteroaryl, halogen, amino, hydroxy, halo$C_{1-6}$alkyl, nitro, $C_{1-6}$alkylthio, sulphonamide, $C_{1-6}$alkylsulphonyl, $C_{1-6}$alkylcarboxamide and carboxamide), hydrogen, $C_{1-6}$alkyl, $C_{3-6}$cycloalkyl, $C_{4-6}$cycloalkenyl, $C_{2-6}$alkenyl, $C_{2-6}$alkynyl, $C_{1-6}$alkoxy$C_{1-6}$alkyl, cyano, carboxyl and carboxy$C_{1-6}$alkyl; and $R^7$ is hydrogen, halogen, $C_{1-6}$alkyl or $C_{1-6}$alkoxy;
or
a pharmaceutically acceptable salt or solvate thereof.

Further examples of compounds of formula (I) above include Examples 1 to 40.

As used herein the term alkyl as a group or part of a group means a straight or branched chain alkyl group. Such alkyl groups include methyl, ethyl, i-propyl, n-propyl, n-butyl, s-butyl, t-butyl, n-pentyl, isopently, neopentyl, n-hexyl, isohexyl and neohexyl. References to alkenyl groups include groups which may be in the E- or Z-form or a mixture thereof and which when they contain at least three carbon atoms, may be branched. Examples of particular alkenyl groups include vinyl, allyl, butenyl, isobutenyl, pentenyl, isopentenyl, hexenyl, isohexenyl, neohexenyl and 1-methyl-2-propenyl. The terms alkoxy and alkynyl have meanings as understood by the person skilled in the art and include straight and branched chains. Examples of alkoxy groups include methoxy and ethoxy and examples of alkynyl groups include ethynyl, propynyl and butynyl.

As used herein the terms cycloalkyl and cycloalkenyl have meanings as understood by the person skilled in the art and include cyclopropyl, cyclobutyl, cyclobutenyl, cyclopentyl, cyclopentenyl, cyclopentadienyl, cyclohexyl, cyclohexenyl and cyclohexadienyl.

The term halogen includes chloro, bromo, fluoro and iodo. The term halo$C_{1-6}$alkyl means an alkyl group in which one or more hydrogens is replaced by halo and preferably containing one, two or three halo atoms. Examples of such groups include trifluoromethyl and fluoroisopropyl.

As used herein the term aryl as a group or part of a group means $C_{6-12}$aryl aromatic groups and includes one or two $C_6$ aromatic rings. The term covers fused ring systems as well as systems in which rings are connected through a linking group, for example —N—, —C—, —O— or —S—, or a bond. Examples of such groups include phenyl, naphthyl, and biphenyl.

As used herein the term heteroaryl as a group or part of a group means $C_{2-14}$heteroaryl aromatic groups optionally substituted with one or more substituents independently selected from hydrogen, halogen, $C_1$6alkyl or $C_{1-6}$alkoxy and includes one or two $C_{5-7}$ aromatic rings containing one or more (for example, one to three) heteroatoms selected from oxygen, sulphur, and nitrogen. The term includes the substituent $R^6$ as hereinbefore defined, fused ring systems as well as systems in which rings are connected through a linking group, for example —N—, —C—, —O— or —S—, or a bond. Examples of such groups include 1,2-benzoisoxazolyl, pyridyl, thiadiazolyl, indazolyl, benzofuryl, quinolyl, thienyl and isoquinolyl.

The term 5- and 6-membered heterocyclic ring means a saturated or partially saturated 5- and 6-membered ring. Examples of such saturated groups include piperidinyl and pyrrolidinyl and partially saturated groups include tetrahydropyridinyl. The term halo$C_{1-6}$alkyl means an alkyl group in which one or more hydrogens is replaced by halo and preferably containing one, two or three halo atoms. Examples of such groups include trifluorobutyl and trifluoromethyl.

The term halo$C_{2-6}$alkenyl means an alkenyl group in which one or more hydrogens is replaced by halo and preferably containing one, two or three halo groups. The halo atoms may be present on saturated or unsaturated carbon atoms. Examples of such groups include 2-chloropropenyl, 3,3-difluoropropenyl and 1,1-difluoropropenyl.

The term halo$C_{2-6}$alkynyl means an alkynyl group in which one or more hydrogens is replaced by halo and preferably containing one, two or three halo groups. The term includes alkynyl groups with a terminal halo atom. Examples of such groups include 3-chloropropynyl and 3-bromopropynyl.

It will be appreciated that some of the compounds of formula (I) and their salts and solvates may contain one or more centres of chirality and exist as stereoisomers including diastereomers and enantiomers. The present invention includes the aforementioned stereoisomers within its scope and each of the individual (R) and (S) enantiomers of the compounds of formula (I) and their salts and solvates substantially free, ie associated with less than 5%, preferably less than 2%, in particular less than 1% of the other enantiomer and mixtures of such enantiomers in any proportions including racemic mixtures containing substantially equal amounts of the two enantiomers. The preferred enantiomers are the (S) enantiomers.

Preferred compounds according to the present invention include compounds of formula (I) wherein one of $R^1$ and $R^2$ is hydrogen; or a pharmaceutically acceptable salt or solvate thereof.

$R^6$ is preferably in the ortho position.

Further preferred compounds of formula (I) include those wherein one of $R^1$ and $R^2$ is hydrogen and the other is $C_{6-12}$aryl$C_{1-6}$alkyl (where the alkyl or aryl moiety may be optionally substituted by one or more substituents selected from $C_{1-6}$alkoxy and $C_{2-14}$heteroaryl); $R^3$, $R^4$ and $R^5$ are hydrogen, Y is oxygen, the dotted line represents a bond and $R^7$ is hydrogen or halogen; or a pharmaceutically acceptable salt or solvate thereof.

In another preferred embodiment of the present invention, the compounds of formula (I) include those wherein $R^1$ and $R^2$ are both hydrogen; one of $R^3$ and $R^4$ is hydrogen and the other is $C_{1-6}$alkyl, $C_{2-6}$alkenyl, $C_{2-6}$alkynyl, $C_{1-6}$alkoxy-$C_{1-6}$alkyl or $C_{6-12}$arylalkyl; $R^5$ is hydrogen, Y is oxygen or —NCH$_3$, the dotted line represents a bond and $R^7$ is hydrogen or halogen; or a pharmaceutically acceptable salt or solvate thereof.

A further preferred embodiment of the present invention includes the compounds of formula (I) wherein $R^1$ and $R^2$ are both hydrogen; one of $R^3$ and $R^4$ is hydrogen and the other is $C_{1-6}$alkyl, $C_{2-6}$alkenyl, $C_{2-6}$alkynyl, $C_{1-6}$alkoxy$C_{1-6}$alkyl, $C_{6-12}$arylalkyl, halo$C_{1-6}$alkyl or halo$C_{2-6}$alkenyl; $R^5$ is hydrogen, Y is oxygen or —NCH$_3$, the dotted line represents a bond and $R^7$ is hydrogen or halogen; or a pharmaceutically acceptable salt or solvate thereof.

Particularly preferred compounds of formula (I) include those wherein $R^1$ and $R^2$ are both hydrogen; one of $R^3$ and $R^4$is hydrogen and the other is $C_{1-6}$alkyl, $C_{2-6}$alkenyl, $C_{2-6}$alkynyl, $R^5$ is hydrogen, Y is oxygen, the dotted line represents a bond and $R^7$ is hydrogen or halogen; or a pharmaceutically acceptable salt or solvate thereof.

Particularly preferred compounds according to the invention, which have been found to be useful in the treatment of depression, are:
2-(1,2-Benzisoxazol-3-yl)-benzenemethanamine;
2-(1,2-Benzisoxazol-3-yl)-α-2-propenyl-benzenemethanamine;

(R)-(+)-2-(1,2-Benzisoxazol-3-yl)-α-2-propenyl-benzenemethanamine;
(S)-(−)-2-(1,2-Benzisoxazol-3-yl)-α-2-propenyl-benzenemethanamine;
2-(1,2-Benzisoxazol-3-yl)-α-butyl-benzenemethanamine;
2-(1,2-Benzisoxazol-3-yl)-α-2-propynyl-benzenemethanamine;
2-(1-Methyl-IH-indazol-3-yl)-α-2-propenyl-benzenemethanamine;
(−)-2-(6-chloro-1,2-benzisoxazol-3-yl)-α-2-propynyl-benzenemethanamine;
(S)-(−)-2-(6-chloro-1,2-benzisoxazol-3-yl)-α-2-propenyl-benzene-methanamine;
and pharmaceutically acceptable salts and solvates thereof.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

Salts according to the invention include ammonium salts, alkali metal salts such as those of sodium or potassium, alkali earth metals salts such as those of calcium and magnesium, salts with organic bases such as dicyclohexylamine and N-methyl-D-glucamine, and salts with amino acids, such as arginine and lysine. Examples of pharmaceutically acceptable acid addition salts include those derived from mineral acids such as hydrochloric, hydrobromic, hydroiodic, phosphoric, metaphosphoric, nitric and sulphuric acids, and organic acids, such as tartaric, acetic, trifluoroacetic, citric, malic, lactic, maleic, malonic, fumaric, benzoic, ascorbic, propionic, glycolic, gluconic, succinic and methanesulphonic and arylsulphonic, for example p-toluenesulphonic acids.

Preferred salts according to the invention include hydrochloric, fumaric ((E)butenedioate) and maleic acid ((Z)butenedioate) addition salts.

Solvates according to the invention include hydrates.

In a further aspect of the invention there are provided the compounds of formula (I) and their pharmaceutically acceptable salts and solvates for use in therapy, more particularly in the treatment or prevention of depression.

Depression states in the treatment of which the compounds of formula (I) and their pharmaceutically acceptable salts and solvates are particularly useful, are those classified as *affective disorders* in the Diagnostic and Statistical Manual of Mental Disorders. Fourth Edition-Revised, American Psychiatric Association, Washington, D.C. (1994), including the mood disorders, other specific affective disorders and bipolar and depressive disorders not otherwise specified.

Other uses in human therapy for the compounds of formula (I) or a pharmaceutically acceptable salt or solvate thereof includes the treatment of the following conditions:

anxiety disorders, including phobic neuroses, panic neuroses, anxiety neuroses, post-traumatic stress disorder and acute stress disorder. attention deficit disorders.

eating disorders, including obesity, anorexia nervosa and bulimia.

personality disorders, including borderline personality disorders.

schizophrenia and other psychotic disorders, including schizo affective disorders, dilusional disorders, shared psychotic disorder, brief psychotic disorder and psychotic disorder.

narcolepsy-cataplexy syndrome.
substance related disorders.
sexual function disorders.
sleep disorders.

The present invention further includes a method for the treatment of an animal, for example, a mammal including a human, suffering from or liable to suffer from depression or any of the aforementioned disorders, which comprises administering an effective amount of a compound of formula (I) or a pharmaceutically acceptable salt or solvate thereof.

In yet a further aspect, the present invention provides the use of a compound of formula (I) or a pharmaceutically acceptable salt or solvate thereof in the manufacture of a medicament for the treatment or prevention of depression or any of the aforementioned disorders.

The amount of a compound of formula (I) or a pharmaceutically acceptable salt or solvate, also referred to herein as the active ingredient, which is required to achieve a therapeutic effect will, of course, vary with the particular compound, the route of administration, the age and condition of the recipient, and the particular disorder or disease being treated.

A suitable daily dose for any of the above mentioned disorders will be in the range of 0.01 to 125 mg per kilogram body weight of the recipient (e.g. a human) per day, preferably in the range of 0.1 to 50 mg per kilogram body weight per day and most preferably in the range 0.25 to 25 mg per kilogram body weight per day. The desired dose may be presented as one, two, three, four, five or more sub-doses administered at appropriate intervals throughout the day.

While it is possible for the active ingredient to be administered alone, it is preferable to present it as a pharmaceutical formulation. Accordingly, the present invention further provides a pharmaceutical formulation comprising a compound of formula (I) or a pharmaceutically acceptable salt or solvate thereof, together with a pharmaceutically acceptable carrier thereof and optionally other therapeutic agents. The carrier must be "acceptable" in the sense of being compatible with the other ingredients of the formulation and not deleterious to the recipients thereof.

Formulations include those suitable for oral, rectal, nasal, topical (including transdermal, buccal and sublingual), vaginal or parenteral (including subcutaneous, intramuscular, intravenous, intradermal and intravitreal) administration. The formulations may be prepared by any methods well known in the art of pharmacy, for example, using methods such as those described in Gennaro et al., Remington's Pharmaceutical Sciences (18th ed., Mack Publishing company, 1990, see especially Part 8: Pharmaceutical Preparations and their Manufacture). Such methods include the step of bringing into association the active ingredient with the carrier which constitutes one or more accessory ingredients. Such accessory ingredients include those conventional in the art, such as, fillers, binders, diluents, disintegrants, lubricants, colorants, flavoring agents and wetting agents.

Formulations suitable for oral administration may be presented as discrete units such as pills, tablets or capsules each containing a predetermined amount of active ingredient; as a powder or granules; as a solution or suspension. The active ingredient may also be presented as a bolus or paste, or may be contained within liposomes.

Formulations for rectal administration may be presented as a suppository or enema.

For parenteral administration, suitable formulations include aqueous and non-aqueous sterile injection. The formulations may be presented in unit-dose or multi-dose containers, for example, sealed vials and ampoules, and may be stored in a freeze dried (lyophilised) condition requiring only the addition of the sterile liquid carrier, for example, water prior to use.

Formulations suitable for administration by nasal inhalation include fine dusts or mists which may be generated by means of metered dose pressurised aerosols, nebulisers or insufflators.

The present invention further includes the following processes for the preparation of compounds of formula(I).

In the following description the symbols $R^1$, $R^2$, $R^3$, $R^4$, $R^5$, $R^6$, $R^7$, $R^8$ and Y have the meanings ascribed to them in formula (I) unless otherwise stated.

According to a first general process A, compounds of formula (I) wherein $R^3$ is as hereinbefore defined and $R^4$ is hydrogen, may be prepared by reductive amination, by reacting the compound of formula (II)

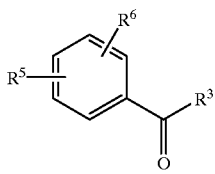

(II)

with an amine of formula $R^1$—NH—$R^2$ wherein $R^1$ and $R^2$ are not both hydrogen to prepare an intermediate imine. The reaction may be carried out azeotropically by distillation, or with a drying agent, such as titanium(IV)chloride or more preferably using molecular sieves in an apolar solvent, for example hexane, toluene or tetrahydrofuran; at a temperature of 0° to 110° C. The addition of an acid catalyst such as p-toluenesulfonic acid may be advantageous.

The resulting intermediate imine is subsequently reduced, for example, by reaction with hydrogen in the presence of a suitable hydrogenation catalyst, either heterogeneous or homogeneous. Alternatively, metals such as zinc or activated zinc in the presence of an acid, for example hydrochloric, or borane or formic acid may be used to carry out the reduction. The reduction is preferably carried out in the presence of a hydride, such as sodium cyanoborohydride, sodium triacetoxyborohydride or sodium borohydride in a polar solvent, preferably a lower alcohol, for example methanol or isopropanol, at a temperature of 0° to 100° C.

According to a second general process B, compounds of formula (I) wherein $R^3$ is as hereinbefore defined and $R^4$ is not hydrogen may be synthesised by treating the intermediate imines prepared in the manner described in process A above, with an appropriate organometallic reagent, such as a Grignard, or a lithium or zinc reagent derived from $R^4$—$L^1$ in which $L^1$ is a suitable leaving group, for example, a halogen, such as a chloro or bromo atom, in the presence of an apolar solvent such as hexane, toluene or tetrahydrofuran, at a temperature of −100° C. to 100° C., typically at room temperature.

The $R^4$ substituent may be introduced stereoselectively by the use of chiral amines i.e. amines of formula $R^1$-NH-$R^2$ wherein $R^1$ and $R^2$ are chiral and optically pure. For example, chirally pure amino acid esters such as valine or alanine. This reaction may conveniently be carried out in a manner analogous to that developed for the enantioselective synthesis of homoallylic amines (A. Bocoum et al., J. Chem. Soc. Chem. Commun., 1993, 1542–1544).

Alternatively, compounds of formula (I) wherein $R^3$ is as hereinbefore defined, $R^4$ is not hydrogen and $R^1$ and $R^2$ are both hydrogen may be prepared by reacting a compound of formula (II) with a suitable amide, for example bis (trimethylsilyl)amide in tetrahydrofuran at a reduced temperature of 0° to −100° C., followed by treatment with an appropriate organometallic reagent as described above.

According to a third general process C, compounds of formula (I) wherein $R^1$ and $R^2$ are both hydrogen may be prepared by reacting a compound of formula (X)

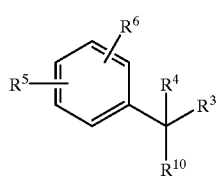

(X)

wherein $R^{10}$ is an azido group with a suitable reducing agent, for example lithium aluminium hydride, sodium borohydride or hydrazine in the presence of palladium or tin complexes. Alternatively, the reaction may be carried out in hydrogen and a suitable hydrogenation catalyst or triphenylphosphine in a mixture of solvents such as water and diethyl ether or tetrahyrofuran at an elevated temperature, for example 20° to 60° C. Alternatively, compounds of formula (I) wherein $R^1$ and $R^2$ are both hydrogen may be synthesised from compounds of formula (X) wherein $R^{10}$ is a suitable leaving group such as mesylate, triflate or a halogen for example a chloro, bromo or iodo atom by a Gabriel synthesis. For example, the Gabriel synthesis may be carried out using potassium phtalimide in a polar aprotic solvent such as N,N-dimethylformamide at an elevated temperature, for example 25° to 140° C., followed by hydrolysis with hydrazine in a polar solvent such as ethanol at an elevated temperature, for example 25° to 80° C.

Compounds of formula (X) wherein $R^{10}$ is a mesylate or triflate group may be prepared by methods described in Advanced Organic Chemistry, March G., 4th Ed, pages 404–405.

Compounds of formula (X) wherein $R^{10}$ is an azido group may be prepared from compounds of formula (X) wherein $R^{10}$ is a leaving group as hereinbefore defined by substitution with inorganic azide salts in a polar solvent at an elevated temperature or by reacting a compound of formula (XI)

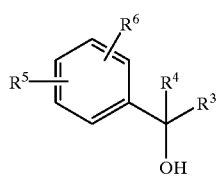

(XI)

with a mixture of triphenylphosphine, diethyl azodicarboxylate and diphenylphosphoryl azide in an apolar solvent such as toluene or benzene at an elevated temperature, for example 20° to 60° C.

Compounds of formula (XI) wherein $R^4$ is hydrogen may conveniently be prepared by reduction of a compound of formula (II) using methods known to those skilled in the art. Suitable reducing agents include hydrides such as lithium alkylborohydride, lithium aluminium hydride or borane or substituted boranes. The reaction may be carried out in an aprotic solvent such as diethyl ether and/or tetrahydrofuran.

Other suitable hydrides include sodium borohydride in a polar solvent such as an alcohol at a temperature of −30° to 100° C. Compounds of formula (II) wherein $R^3$ is other than hydrogen may be asymmetrically reduced using chiral boranes or optically active catalysts and achiral reducing agents. Compounds of formula (XI) wherein $R^4$ is other than hydrogen may be prepared by reacting a compound of formula (II) with a suitable organometallic reagent in the manner described above for process A.

According to a fourth process D, compounds of formula (I) wherein one of $R^3$ or $R^4$ is cyano or carboxyl may be prepared from a compound of formula (I) by a Strecker synthesis. This process may be performed in an analogous manner to that described for DL-2-aminophenylacetic acid (Vogel, Textbook of Practical Organic Chemistry, 5th Edition, 1989, p754). The carboxylic acid obtained may be esterified to carboxy$C_{1-6}$alkyl groups by reaction with an alcohol. The reaction may be carried out azeotropically by distillation, by adding a dehydrating agent such as dicyclohexylcarbodiimide, N,N'-carbonyldiimidazole or diethyl azodicarboxylate with triphenylphosphine or by the addition of molecular sieves. This reaction may be catalysed by the addition of an acid. Alternatively, carboxylic acid esters may be prepared by treating the compound of formula (I) wherein $R^3$ or $R^4$ is a carboxyl group with an alkylether such as $C_{1-6}$alkyl-t-butyl ethers in the presence of an acid catalyst, alkylation using a diazo compound such as diazomethane in aprotic solvent, for example tetrahydrofuran or diethyl ether at a temperature of −30° C. to 30° C. Esters may also be prepared by transesterification under basic or acidic conditions or by alkylation of the inorganic salts of the carboxylic acid compound using methods known to a person skilled in the art.

According to a fifth process E, compounds of formula (I) wherein one of $R^3$ and $R^4$ is hydrogen and the other is as hereinbefore defined and one of $R^1$ and $R^2$ is hydrogen and the other is a $C_{6-12}$aryl$C_{1-6}$alkyl wherein the aryl or alkyl moiety may be substituted as hereinbefore described, may be prepared by reductive di-alkylation by reacting a corresponding compound of formula (II) with ammonia or an ammonium salt such as ammonium acetate to prepare an intermediate imine. Reduction of the imine may be carried out in accordance with the procedure described in process A above.

According to a sixth process F, compounds of formula (I) may be prepared by solid phase chemistry using methods known to a skilled person or available from the chemical literature. For example, compounds of formula (I) wherein one of $R^1$ and $R^2$ is hydrogen and the other is $C_{6-12}$aryl$C_{1-6}$alkyl, $C_{2-14}$heteroaryl$C_{1-6}$alkyl, or $C_{1-6}$alkyl where the alkyl moiety is substituted with a substituent selected from amino, hydroxy, $C_{1-6}$alkylcarboxamide, carboxamide, carboxy and carboxy$C_{1-6}$alkyl and in addition the alkyl, aryl or heteroaryl moiety may be optionally substituted by one or more substituents selected from amino, hydroxy, $C_{1-6}$alkoxy, $C_{1-6}$alkyl, $C_{3-6}$cycloalkyl, $C_{4-6}$cycloalkenyl, $C_{6-12}$aryl, $C_{2-14}$heteroaryl, halogen, amino, hydroxy, halo$C_{1-6}$alkyl, nitro, $C_{1-6}$alkylthio, sulphonamide, $C_{1-6}$alkylsulphonyl, hydroxy$C_{1-6}$alkyl, carboxyl, carboxy$C_{1-6}$alkyl, carboxamide, and $C_{1-6}$alkylcarboxamide, and one of $R^3$ and $R^4$ is hydrogen and the other is as hereinbefore defined, may conveniently be prepared by reductive alkylation, arylalkylation or heteroarylalkylation of an amino acid bound to benzyl alcohol resin such as a Wang or SASRIN resin, with a compound of formula (II) wherein $R^3$ is hydrogen using standard methods (see for example D. W. Gordon and J. Steele, Bioorganic Med. Chem. Lett., 1995, 5, 47–50 & G. C. Look et al., Tetrahedron Lett. 1995, 36, 2937–2940). Suitable reducing agents include hydrides, for example cyanoborohydride, sodium triacetoxyborohydride or sodium borohydride. The reaction may be carried out in trimethyl orthoformate, dimethylformamide or mixtures thereof in the presence of a small amount of acetic acid (typically 1% v/v).

The compound of formula (I) may conveniently be obtained by treating the solid phase with ammonia or a lower alkylamine such as methylamine in a manner analogous to that used for the preparation of peptide amides from resin bound peptides (M. Mergler and Nyfeler, Solid Phase Synthesis, 1992, R. Epton (Ed), Andover, p429).

According to a seventh general process G, compounds of formula (I) wherein $R^1$ and $R^2$ are both hydrogen and $R^3$, $R^4$, $R^5$ and $R^6$ are as hereinbefore defined may be prepared by treating a compound of formula (XII)

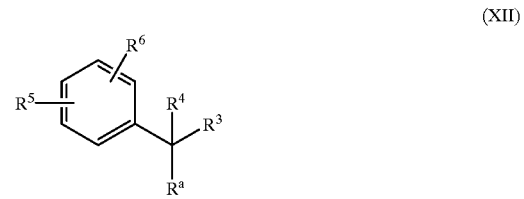

(XII)

wherein $R^a$ is a carboxyl group, with a suitable agent which converts the carboxylic acid group into an amine. This may be carried out using methods well known in the art or readily available from the chemical literature. Such methods include the Curtius rearrangement, Hofmann rearrangement or Schmidt reaction.

According to an eighth general process H, compounds of formula (I) wherein $R^1$, $R^2$ and $R^3$ and are hydrogen and $R^4$ $R^5$ and $R^6$ are as defined above, may be prepared from compounds of formula (XVIII) by hydrolysis. The reaction may conveniently be carried out in the presence of an acid, for example 1M HCl in acetone. Compounds of formula (XVIII) may be prepared from the imine of formula (XIX), for example, by deprotonation by the addition of a base preferably potassium tert-butoxide in an inert solvent, preferably tetrahydrofuran at a temperature of −100° to 25° C. followed by the addition of a reagent $R^4$–$L^a$ in which $L^a$ is a suitable leaving group such as a mesylate- or triflate group or a halo atom, including iodo, bromo or chloro. This general process is described by C. Gianfranco et al (J. Org. Chem., 1996, 61, 5134

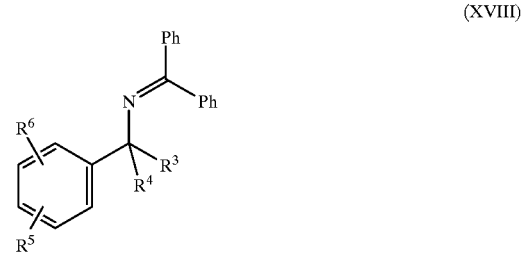

(XVIII)

(XIX)

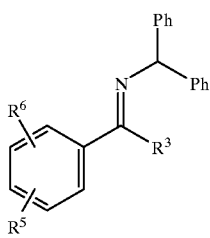

Compounds of formula (XIX) may be prepared by reacting a compound of formula (II) wherein $R^3$ is hydrogen and $R^5$ and $R^6$ are hereinbefore defined with diphenylmethanamine. The reaction may be carried out azeotropically by distillation, or with a drying agent such as titanium (IV) chloride or molecular sieves in an apolar solvent, preferably magnesium sulfate in methylene chloride.

Compounds of formula (I) wherein one of $R^3$ or $R^4$ together with one of $R^1$ or $R^2$ and the N atom to which it is attached form a 5- or 6-membered heterocyclic ring may similarly be prepared by hydrolysis of a compound of formula (XVIII) as described supra. Compounds of formula (XVIII) may be prepared by reacting a compound of formula (XIX) and a compound of formula (XX) wherein $L^b$ and $L^c$ may be the same or different and are leaving groups such as a mesylate- or triflate-group or a halo atom, including iodo, bromo, chloro or fluoro and $R^d$ is a $C_{6-12}$aryl, $C_{2-14}$heteroaryl, $C_{6-12}$aryl$C_{1-6}$alkyl, $C_{2-14}$heteroaryl$C_{1-6}$alkyl, $C_{3-6}$cycloalkyl, $C_{4-6}$cycloalkenyl.

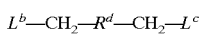

Where necessary or desired, following one or more of processes A to H above, any one or more of the following further steps in any order may be performed:

(i) removing any remaining protecting group(s);
(ii) converting a compound of formula (I) or a protected form thereof into a further compound of formula (I) or a protected form thereof;
(iii) converting a compound of formula (I) or a protected form thereof into a pharmaceutically acceptable salt or solvate of a compound of formula (I) or a protected form thereof;
(iv) converting a pharmaceutically acceptable salt or solvate of a compound of formula (I) or a protected form thereof into a compound of formula (I) or a protected form thereof;
(v) converting a pharmaceutically acceptable salt or solvate of a compound of formula (I) or a protected form thereof into another pharmaceutically acceptable salt or solvate of formula (I);
(vi) where the compound of formula (I) is obtained as a mixture of (R) and (S) enantiomers resolving the mixture to obtain the desired enantiomer.
(vii) cleavage of a compound of fomula (I) from a solid phase resin.

Compounds of formula (II) supra wherein $R^6$ is a benzisoxazol-3-yl group may be prepared from a compound of formula (III)

(III)

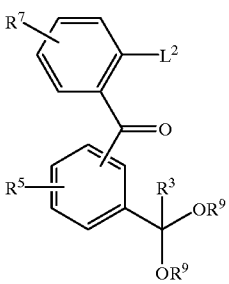

wherein $L^2$ is a leaving group such as a nitro or halogen, preferably a fluoro atom and $R^9$ is a $C_{1-4}$alkyl, for example methyl or ethyl, via the intermediate compound of formula (IV)

(IV)

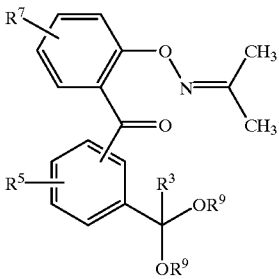

using the process described by Shutske G. M. (J. Org. Chem., 1984, 49, 180–183) for the synthesis of 3-phenyl-1,2-benzisoxazole. Hydrolysis to the aldehyde may be carried out using various catalysts, for example dilute acids such as hydrogen chloride at an elevated temperature, for example 20° to 100° C.

Compounds of formula (III) may be prepared by oxidation of the corresponding compound of formula(V)

(V)

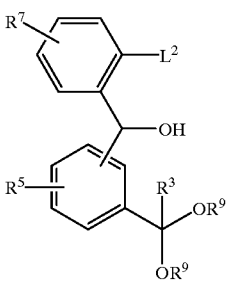

The oxidation may be carried out in the presence of a strong oxidising agent such as potassium permanganate, bromine, ruthenium tetroxide or chromium reagents, for example Jones or Corey's reagent, preferably chromium trioxide in pyridine. The reaction may be carried out at a temperature of 0° to 40° C., in an apolar solvent such as dichloromethane.

Compounds of formula (III) may be prepared by the addition of an organometallic reagent derived, using methods well known to a person skilled in the art, from a compound of formula (VI), to a compound of formula (XXI) wherein $L^2$ is as hereinbefore defined. The addition is typically carried out in the presence of an aprotic solvent such as diethyl ether or tetrahydrofuran at a reduced temperature, for example −100 to 0° C.

(XXI)

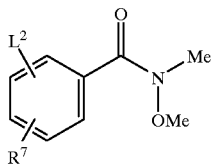

Compounds of formula (XXI) may be obtained commercially or prepared from commercial compounds using the general process described by S. Nahm and S. Weinreb (Tetrahedron Lett., 1981, 22, 3815) using methods well known to a skilled person.

Compounds of formula (V) may be prepared by the addition of an organometallic reagent such as a Grignard or aryllithium, derived using methods well known to a person skilled in the art from a compound of formula (VI)

(VI)

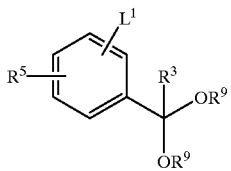

wherein $R^9$ is as hereinbefore defined and $L^1$ is a suitable leaving group such as a nitro-, mesylate- or triflate-group or a halo atom, including iodo, fluoro, bromo or chloro, to an aldehyde of formula (VII)

(VII)

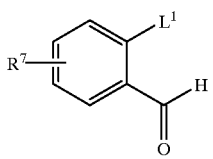

wherein $L^2$ is as hereinbefore defined. The addition is typically carried out in the presence of an aprotic solvent such as diethyl ether or tetrahydrofuran at reduced temperature, for example −100° C. to 0° C.

Aldehydes of formula (VII) may be obtained commercially or prepared by methods well known to a person skilled in the art or readily available from the chemical literature.

Compounds of formula (VI) may be prepared from compounds of formula (VIII)

(VIII)

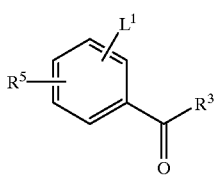

wherein $L^1$ is as herein before defined, by methods well known to a skilled person. This conversion may, for example be carried out by the addition of an alcohol such as ethanol or methanol in the presence of an acid catalyst, for example toluene sulphonic acid or with the use of a drying agent such as aluminium oxide or molecular sieves. Alternatively, the conversion may be carried out transacetalation using an ortho ester such as triethyl orthoformate in the presence of an acid catalyst such as ammonium chloride at a temperature of 0° to 80° C.

Aldehydes of formula (VIII) may be obtained commercially or prepared by methods well known to a person skilled in the art or readily available from the chemical literature.

For process G supra, compounds of formula (XII) may be prepared from compounds of formula (XIII)

(XIII)

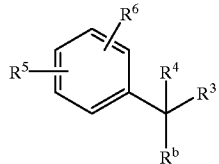

wherein $R^b$ is a carboxy$C_{1-16}$alkyl, for example methyl, ethyl or a chiral ester (such as that derived from (+)- or (−)-menthol) by reaction with an aqueous caustic solution such as 10M potassium hydroxide in a solvent such as 2-methoxyethanol at an elevated temperature such as 60° to 125° C. Compounds of formula (XIII) may be prepared from compounds of formula (XII) by literature methods well known to a person skilled in the art for example acid chloride formation followed by esterification.

Compounds of formula (XIII) may be prepared by the treatment a compound of formula (XIV) with lithium diisopropylamide and a compound of formula $R^4$—$L^2$ wherein $R^4$ is as hereinbefore defined and $L^a$ is as hereinbefore defined, at a temperature of −78° to 25° C. by the general process described by L. A. Paquette and J. P. Gilday (J. Org. Chem., 1988, 53, 4972.).

(XIV)

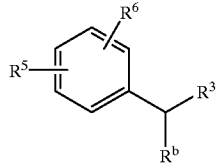

Compounds of formula (XIV) may be prepared from a compound of formula (XV)

(XV)

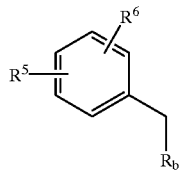

wherein $R^b$, $R^5$ and $R^6$ are hereinbefore defined, by treatment with lithium diisopropylamide and a compound of formula $R^3$—$L^a$ wherein $R^3$ and $L^a$ are as hereinbefore defined, at a temperature of −78° to 25° C.

Compounds of formula (XV) may be prepared from a compound of formula (XVI)

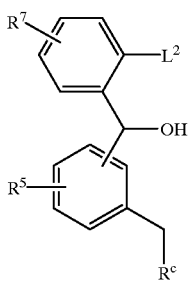

(XVI)

wherein $R^c$ is a $C_{1-6}$ orthoester, such as a trimethyl orthoester, triethyl orthoester or a 2,6,7-trioxabicyclo[2.2.2] octane such as described by E. J. Corey and N. Raju (Tetrahedron Lett., 1983, 24, 5571) and $R^5$, $R^7$ and $L^2$ have been hereinbefore defined, by the general process decribed by G. M. Shutske (J. Org. Chem., 1984, 49, 180) for the synthesis of 3-phenyl-1,2-benzisoxazole and using methods herein described for the conversion of compounds of formula (V) to compounds of formula (II) wherein $R^6$ is a benzisoxazol-3-yl group.

Compounds of formula (XVI) may be prepared by the addition of an organometallic reagent derived using methods well known to a person skilled in the art from a compound of formula (XVII)

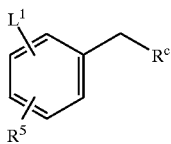

(XVII)

to a compound of formula (VII) hereinbefore defined. The addition is typically carried out in the presence of an aprotic solvent such as diethyl ether or tetrahydrofuran at a reduced temperature, for example −100° to 0° C.

Compounds of formula (XVII) may be prepared by methods well known to person skilled in the art starting from commercially available starting materials.

Compounds of formula (II) wherein $R^6$ is an indazol-3-yl or 1-$C_{1-6}$alkyl-benzopyrazol-3-yl group may be prepared from compounds of formula (IX)

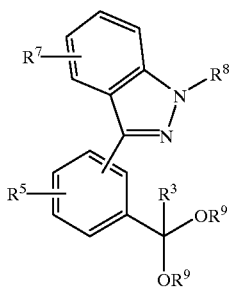

(IX)

where $R^9$ is as hereinbefore defined, by hydrolysis. Hydrolysis may be carried out under conditions described above for the hydrolysis of the compound of formula (III). Such compounds of formula (IX) may be prepared from compounds of formula (III) supra in accordance with the method of B. Bradley (J. Chem. Soc., 1954, 1894–1897.).

Salts according to the present invention may be prepared by treating a compound of formula (I) with an appropriate base, for example an alkali metal, alkaline earth metal or ammonium hydroxide, or an appropriate organic or inorganic acid, such as hydrochloric, fumaric or maleic acid.

Compounds of formula (I), prepared by any of the methods hereinbefore described, may be converted to other compounds of formula (I) by methods well known to a person skilled in the art or readily available from the chemical literature. For example, compounds of formula (I) wherein $R^1$ and/or $R^2$ are hydrogen may be converted to compounds wherein $R^1$ and/or $R^2$ are alkyl, arylalkyl or heteroarylalkyl groups as hereinbefore defined by reaction with the appropriate alkylating agent. Suitable alkylating agents include halides and organic and inorganic esters. The reaction may be carried out in the presence of a base in a polar solvent such as ethanol or N,N-dimethylformamide at an elevated temperature.

Alternatively, these compounds can be prepared by reductive alkylation, for example the Leuchart-Wallach reaction, using carbonyl compounds such as ketones or aldehydes and formic acid or formamides or the Eschweiler-Clarke reaction.

The individual enantiomers of compounds of formula (I) may be prepared as hereinbefore described or obtained from a mixture of stereoisomers using any method well known in the art for separating such isomers into their constituent enantiomers. For example, using methods described in Stereochemistry of Organic Compounds, E. L. Eliel and S. H. Wilen, chapter 7, 1994. In particular they may be obtained by conversion to diastereomers followed by separation of the constituent diastereomers by methods such as salt formation with optically active acids followed by fractional crystallisation or by differential absorption using columns packed with chiral material, for example preparative chiral liquid or gas chromatography.

The present invention further includes all novel intermediates hereinbefore described and in particular compounds of formula (II) provided that the compound of formula (II) is not 4-(1,2-benzisoxazol-3-yl)-benzaldehyde or 4-(6-chloro-1,2-benzisoxazol-3-yl)-benzaldehyde. Preferred compounds of formula (II) include those wherein $R^5$ and $R^6$ are as herein before defined and $R^3$ is hydrogen, $C_{1-6}$alkyl, $C_{2-6}$alkenyl, $C_{2-6}$alkynyl, $C_{1-6}$alkoxy$C_{1-6}$alkyl or $C_{6-12}$arylalky.

Also included are intermediates of formulae (X) and (XI), provided that compound of formula (X) is not 3-(4-bromomethyl-phenyl)-1,2-benzisoxazole or 3-(4-bromomethyl-phenyl)-6-chloro-1,2-benzisoxazole.

Particularly preferred intermediates according to the present invention include:

2-(Diethoxymethyl)-α-(2-fluorophenyl)-benzenemethanol
[2-(Diethoxymethyl)phenyl](2-fluorophenyl)-methanone
O-[2-[2-(Diethoxymethyl)benzoylphenyl]oxime 2-propanone
2-(1,2-Benzisoxazol-3-yl)-benzaldehyde
2-(1-Methyl-1H-indazol-3-yl)-benzaldehyde
(S)-N-[1-[2-(1,2-Benzisoxazol-3-yl)phenyl]-3-butenyl]-L-valine methyl ester

[S-(R*,R*)]-2-[[1-[2-(1,2-Benzisoxazol-3-yl)phenyl]-3-butenyl]amino]-3-methyl-1-butanol
2-(1,2-benzisoxazol-3-yl)-α-2-propenyl-benzenemethanol
3-[2-(1-Azido-3-butynyl)phenyl]-1,2-benzisoxazole
2-(1,2-Benzisoxazol-3-yl)-benzenemethanol
2-[[2-(1,2-Benzisoxazol-3-yl)phenyl]methyl]-1H-isoindole-1,3 (2H)-dione
N-Methoxy-N-methyl-4-chloro-2-fluorobenzamide
[2-(Diethoxymethyl)-phenyl](4-chloro-2-fluorophenyl)-methanone
2-(6-Chloro-1,2-benzisoxazol-3-yl)-benzaldehyde
(S)-N-[1-[2-(6-chloro-1,2-benzisoxazol-3-yl)phenyl]-3-butenyl]-L-valine methyl ester
[S-(R*,R*)]-2-[[ 1-[2-(6-Chloro-1,2-benzisoxazol-3-yl)phenyl]-3-butenyl]amino]-3-methyl-1-butanol
N-[2-(6-chloro-1,2-benzisoxazol-3-yl)-benzylidene]-1,1-diphenylmethanamine The following examples are intended for illustration only and are not intended to limit the scope of the invention in any way.

EXAMPLE 1

2-Bromobenzaldehyde diethyl acetal

To a solution of 634 g of 2-bromobenzaldehyde and 7.17 g ammonium chloride in 400 ml ethanol was added 633 ml of triethyl orthoformate. The mixture was stirred for 16 h at room temperature. After filtration of the remaining salts, the filtrate was evaporated to dryness under reduced pressure, yielding 894 g of an oil. Distillation under reduced pressure afforded 2-bromobenzaldehyde diethyl acetal as a liquid, boiling at 135–140° C. at 270 Pa.

EXAMPLE 2

2-(Diethoxymethyl)-α-(2-fluorophenyl)-benzenemethanol

A solution of 345 g of 2-bromobenzaldehyde diethyl acetal in 3 l of dry tetrahydofuran was cooled to −40° C. In one portion, 913 ml of a 1.6 M solution of butyllithium in hexane were added under vigorous stirring. The resulting solution was stirred for 0.5 h at −25° C., after which a solution of 140 ml of 2-fluorobenzaldehyde in 350 ml tetrahydrofuran was added drop-wise. In a period of 4 h, the mixture was allowed to reach room temperature. The resulting mixture was pored upon ice-water and extracted several times with ethyl acetate. The organic layers were combined, washed with water, dried over magnesium sulphate and evaporated to dryness under reduced pressure to yield 404 g of 2-(diethoxymethyl)-α-(2-fluorophenyl)-benzenemethanol as an oil, M.S. (C.I.) (M/Z): 305 [M+H]$^+$.

EXAMPLE 3

[2-(Diethoxymethyl)phenyl](2-fluorophenyl)-methanone

Under a nitrogen atmosphere, 758 ml of pyridine and 469 g of dicalite were added to 6 l of dry dichloromethane. In one portion 469 g of chromium trioxide were added under vigorous stirring. The resulting mixture was stirred at room temperature for 0.5 h, after which a solution of 238 g of 2-(diethoxymethyl)-α-(2-fluorophenyl)-benzenemethanol in 600 ml dry dichloromethane was added. After stirring at room temperature for 2 h, the mixture was filtered. The filtrate was washed with 3×1 l of 1N sodium hydroxide in water and 1 l of water, dried over magnesium sulphate and evaporated to dryness under reduced pressure to yield 224 g of [2-(diethoxymethyl)phenyl](2-fluorophenyl)-methanone as an oil, M.S. (C.I.) (M/Z): 303 [M+H]$^+$.

EXAMPLE 4

O-[2-[2-(Diethoxymethyl)benzoylphenyl]oxime 2-propanone

To a stirred solution of 63.76 g of acetone oxime in 2 l of dry tetrahydrofuran, were added 97.93 g of potassium tert-butoxide under a nitrogen atmosphere. After stirring for 0.5 h at room temperature, the resulting suspension was treated with a solution of 242 g of [2-(diethoxymethyl)phenyl](2-fluorophenyl)-methanone in 1 l of tetrahydrofuran. The mixture was heated at reflux for 24 h. After cooling to room temperature, water was added. The mixture was extracted several times with ethyl acetate, the organic layers were collected, washed with water, dried over magnesium sulphate and evaporated to dryness under reduced pressure to yield 269.5 g of O-[2-[2-(diethoxymethyl)benzoylphenyl] oxime 2-propanone, M.S. (C.I.) (M/Z): 356 [M+H]$^+$.

EXAMPLE 5

2-(1,2-Benzisoxazol-3-yl)-benzaldehyde

To a solution of 252 g of O-[2-[2-(diethoxymethyl) benzoylphenyl]oxime 2-propanone in 710 ml of ethanol were added 710 ml of a 2N aqueous solution of hydrogen chloride. The mixture was stirred at 70° C. for 1 h and allowed to cool to room temperature. The pH of the solution was adjusted to 7 with an aqueous solution of potassium carbonate. The precipitate was filtered off and dried to afford 159 g of a solid. The compound was recrystallised from ethanol/hexane, affording pure 2-(1,2-benzisoxazol-3-yl)-benzaldehyde, melting at 149° C.

EXAMPLE 6

2-(1-Methyl-1H-indazol-3-yl)-benzaldehyde

A solution of 1.5 g of [2-(diethoxymethyl)phenyl](2-fluorophenyl)-methanone and 0.5 g of methylhydrazine in 50 ml of toluene was refluxed for 24 h. Water was added and the mixture was extracted with ethyl acetate. The combined organic layers were washed with brine, dried over magnesium sulphate and evaporated to dryness under reduced pressure to yield 1.12 g of 2.1. as an oil.

To a solution of 1.1 g of this oil in 50 ml of ethanol were added 50 ml of a 2N aqueous solution of hydrogen chloride. The mixture was stirred at 70° C. for 1 h and allowed to cool to room temperature. The pH of the solution was adjusted to 7 with an aqueous solution of potassium carbonate. This solution was extracted several times with dichloromethane. The combined organic layers were washed with brine, dried over magnesium sulphate and evaporated to dryness under reduced pressure to yield 0.78 g of 2-(1-methyl-1H-indazol-3-yl)-benzaldehyde as a solid, melting at 106° C.

EXAMPLE 7

2-Bromo-4-fluoro-benzaldehyde diethyl acetal

To a solution of 6.5 g of 2-bromo-4-fluoro-benzaldehyde (prepared by the oxidation of 2-bromo-4-fluoro-toluene by the method reported by V. J. Bauer, B. J. Duffy, D. Hoffman, S. S. Klioze, R. W. Kosley, Jr., A. R. McFadden, L. L. Martin, H. H. Ong and H. M. Geyer III, J. Med. Chem., 1976, 19, 1315) in 25 ml of ethanol was added triethylorthoformate followed by 0.05 g of p-toluene sulfonic acid. The solution was stirred at room temperature for 2.25 h then diluted with 100 ml of a 5% sodium carbonate solution and extracted with two 100 ml portions of ether. The combined organic layers were washed with 50 ml of brine and dried over sodium sulfate. Evaporation of the solvent yielded 8.8 g of 2-bromo-4-fluoro-benzaldehyde diethyl acetal as an oil, $^1$H NMR (200 MHz; CDCl$_3$)$\delta_H$ 5.60 (CHO$_3$).

In a similar way were prepared:
1. 2-bromo-5-fluoro-benzaldehyde diethyl acetal: starting from 2-bromo-5-fluoro-benzaldehyde (F. B. Mallory, C. W. Mallory, W. M. Ricker, J. Org Chem., 1985, 50, 4), $^1$H NMR (200 MHz; CDCl$_3$)$\delta_H$ 5.60 (CHO$_3$).
2. 2-bromo-4-chloro-benzaldehyde diethyl acetal: starting from 2-bromo-4-chloro-benzaldehyde (K. Murakami, S. Shuhei, T. Yano, M. Itoh, Eur. Pat. Appl. EP 684235 A1 951129), $^1$H NMR (200 MHz; CDCl$_3$) 8H 5.60 (CHO$_3$).
3. 3-bromobenzaldehyde diethylacetal; starting from 3-bromobenzaldehyde, boiling at 102–110° C. at 2.5 mmHg,
4. 4-bromobenzaldehyde diethylacetal; starting from 4-bromobenzaldehyde, $^1$H NMR (200 MHz; CDCl$_3$)$\delta_H$ 5.48 (CHO$_3$).

EXAMPLE 8

N-Methoxy-N-methyl-4-chloro-2-fluorobenzamide

A suspension of 19.7 g of 4-chloro-2-fluorobenzoic acid in 80 ml of thionyl chloride was refluxed for 1.5 h. The excess thionyl chloride was removed under reduced pressure to give the crude intermediate acid chloride as an oil. This crude acid chloride was dissolved in 300 ml of methylene chloride and 20 ml of pyridine was added. The solution was cooled to 0° C. and 12.9 g of N,O-dimethylhydroxylamine hydrochoride was added in one portion. The solution was stirred at room temperature overnight then diluted with 200 ml of methylene chloride and washed with 100 ml each of water, 2M hydrochloric acid, 5% sodium carbonate solution and brine. The organic layer was dried over sodium sulfate and evaporated to give 23.5 g of N-Methoxy-N-methyl-4-chloro-2-fluorobenzamide as a gum, GC-M.S. (E.I.) (M/Z): 217 [M]$^+$.

In a similar way were prepared:
1. N-Methoxy-N-methyl-2-fluorobenzamide, $^1$H NMR (200 MHz; CDCl$_3$)$\delta_H$ 3.60, 3.35 (CH$_3$).
2. N-Methoxy-N-methyl-2,4-difluorobenzamide, $^1$H NMR (200 MHz; CDCl$_3$)$\delta_H$ 3.56, 3.35 (CH$_3$).
3. N-Methoxy-N-methyl-2,5-difluorobenzamide, $^1$H NMR (200 MHz; CDCl$_3$)$\delta_H$ 3.55, 3.36 (CH$_3$).
4. N-Methoxy-N-methyl-4-chloro-2-fluorobenzamide, $^1$H NMR (200 MHz; CDCl$_3$)$\delta_H$ 3.56, 3.35 (CH$_3$).
5. N-Methoxy-N-methyl-4-trifluoromethyl-2-fluorobenzamide, $^1$H NMR (200 MHz; CDCl$_3$)$\delta_H$ 3.53, 3.38 (CH$_3$).

EXAMPLE 9

[2-(Diethoxymethyl)-phenyl](4-chloro-2-fluorophenyl)-methanone

A stirred solution of 10.6 g of 2-bromobenzaldehyde diethyl acetal in 100 ml of diethyl ether was cooled to −40° C. To this cold solution was added rapidly 46 ml of a 1.2 M solution of butyllithium in hexane. The solution was warmed to 0° C. over 30 min. The solution was cooled down to −40° C. and a solution of 11.9 g of N-Methoxy-N-methyl-4-chloro-2-fluorobenzamide in 100 ml of diethyl ether added by cannular. The solution was warmed to 0° C. and stirred for 0.75 h then quenched by the addition of 100 ml of water and 200 ml of ether added. The organic layer was separated and the aqueous layer was extracted with 200 ml of ether. The combined organic layers were dried over sodium sulfate and evaporated to yield 19.6 g of crude [2-(diethoxymethyl)-phenyl](4-chloro-2-fluorophenyl)-methanone as a gum, GC-M.S. (E.I.) (M/Z) 336 [M]$^+$.

In a similar way were prepared:
1. [2-(Diethoxymethyl)-phenyl](2,4-difluorophenyl)-methanone; starting from N-Methoxy-N-methyl-2,4-difluorobenzamide and 2-bromobenzaldehyde 2. [2-(Diethoxymethyl)-phenyl](2,5-difluorophenyl)-methanone; starting from N-Methoxy-N-methyl-2,5-difluorobenzamide and 2-bromobenzaldehyde diethyl acetal, $^1$H NMR (200 MHz; CDCl$_3$)$\delta_H$ 5.77 (CHO$_2$).
2. [2-(Diethoxymethyl)-5-fluorophenyl](2-fluorophenyl)-methanone; starting from N-Methoxy-N-methyl-2-fluorobenzamide and 2-bromo-4-fluorobenzaldehyde diethyl acetal, $^1$H NMR (200 MHz; CDCl$_3$)$\delta_H$ 5.83 (CHO$_2$).
3. [2-(Diethoxymethyl)-4-fluorophenyl](2-fluorophenyl)-methanone; starting from N-Methoxy-N-methyl-2-fluorobenzamide and 2-bromo-5-fluorobenzaldehyde diethyl acetal, $^1$H NMR (200 MHz; CDCl$_3$)$\delta_H$ 5.62 (CHO$_2$).
4. [4-Chloro-2-(diethoxymethyl)phenyl](2-fluorophenyl)-methanone; starting from N-Methoxy-N-methyl-2-fluorobenzamide and 2-bromo-5-chlorobenzaldehyde diethyl acetal, $^1$H NMR (200 MHz; CDCl$_3$)$\delta_H$ 5.76 (CHO$_2$).
5. [2-(Diethoxymethyl)-5-fluorophenyl](2,5-difluorophenyl)-methanone; starting from N-Methoxy-N-methyl-2,5-difluorobenzamide and 2-bromo-4-fluorobenzaldehyde diethyl acetal, $^1$H NMR (200 MHz; CDCl$_3$)$\delta_H$ 5.68 (CHO$_2$).
6. [2-(Diethoxymethyl)-4-fluorophenyl](2,5-difluorophenyl)-methanone; starting from N-Methoxy-N-methyl-2,5-difluorobenzamide and 2-bromo-5-fluorobenzaldehyde diethyl acetal, $^1$H NMR (200 MHz; CDCl$_3$)$\delta_H$ 5.80 (CHO$_2$).
7. [2-(Diethoxymethyl)-4-fluorophenyl](4-chloro-2-fluorophenyl)-methanone; starting from N-Methoxy-N-methyl-4-chloro-2-fluorobenzamide and 2-bromo5-fluoro-benzaldehyde diethyl acetal, $^1$H NMR (200 MHz; CDCl$_3$)$\delta_H$ 5.77 (CHO$_2$).
8. [4-Chloro-2-(diethoxymethyl)phenyl](4-chloro-2-fluorophenyl)-methanone; starting from N-Methoxy-N-methyl-4-chloro-2-fluorobenzamide and 2-bromo5-chloro-benzaldehyde diethyl acetal, $^1$H NMR (200 MHz; CDCl$_3$)$\delta_H$ 5.73 (CHO$_2$).
9. [(2-Diethoxymethyl)-4-trifluoromethyl phenyl](2-fluorophenyl)-methanone; starting from N-Methoxy-N-methyl-4-trifluoromethyl-2-fluorobenzamide and 2-bromobenzaldehyde diethyl acetal, $^1$H NMR (200 MHz; CDCl$_3$) $\delta_H$ 5.76 (CHO$_2$).
10. [(2-Diethoxymethyl)phenyl](2-fluorophenyl)-methanone; starting from N-Methoxy-N-methyl-2-fluorobenzamide and 2-bromobenzaldehyde diethyl acetal, $^1$H NMR (200 MHz; CDCl$_3$)$\delta_H$ 5.75 (CHO$_2$).
11. [(3-Diethoxymethyl)phenyl](2-fluorophenyl)-methanone; starting from N-Methoxy-N-methyl-2-fluorobenzamide and 3-bromobenzaldehyde diethyl acetal, $^1$H NMR (200 MHz; CDCl$_3$)$\delta_H$ 5.55 (CHO$_2$).
12. [(4-Diethoxymethyl)phenyl](2-fluorophenyl)-methanone; starting from N-Methoxy-N-methyl-2-fluorobenzamide and 4-bromobenzaldehyde diethyl acetal, $^1$H NMR (200 MHz; CDCl$_3$)$\delta_H$ 5.56 (CHO$_2$).

EXAMPLE 10

2-(6-Chloro-1,2-benzisoxazol-3-yl)-benzaldehyde

To a solution of 3.3 g of acetone oxime in 80 ml of tetrahydrofuran was added 5.3 g of potassium tert-butoxide. The suspension was stirred for 30 min then a solution of 14.5 g of crude [2-(diethoxymethyl)-phenyl](4-chloro-2-fluorophenyl)-methanone in 20 ml of tetrahydrofuran was added and the solution was refluxed for 3.5 h. The solution was cooled to room temperature and diluted with 200 ml of water then extracted with 400 ml then 200 ml portions of ethyl acetate. The combined organic layers were washed with 200 ml of brine then dried over sodium sulfate and evaporated to yield 14.6 g of crude O-[(2-(diethoxymethyl)benzoyl)-4-chlorophenyl] oxime 2-propanone as a gum. This material was suspension in 40 ml of ethanol and heated. To this suspesion was added 80 ml of methanol and the solution heated to reflux. To this solution was added 27 ml of 2M hydrochloric acid in one portion. A solid separated out and upon cooling this was filtered, washed with water and dried in vacuo over silica gel to yield 6.3 g of 2-(6-chloro-1,2-benzisoxazol-3-yl)-benzaldehyde melting at 160–162° C.

In a similar way were prepared:
1. 2-(6-fluoro-1,2-benzisoxazol-3-yl)-benzaldehyde; starting from [2-(diethoxymethyl)-phenyl](2,4-difluorophenyl)-methanone, melting at 168–170° C.
2. 2-(5-fluoro-1,2-benzisoxazol-3-yl)-benzaldehyde; starting from [2-(diethoxymethyl)-phenyl](2,5-difluorophenyl)-methanone, melting at 140–142° C.
3. 2-(1,2-benzisoxazol-3-yl)-4-fluoro-benzaldehyde; starting from [2-(diethoxymethyl)-5-fluorophenyl](2-fluorophenyl)-methanone, melting at 126–129° C.
4. 2-(1,2-benzisoxazol-3-yl)-5-fluoro-benzaldehyde; starting from [2-(diethoxymethyl)-4-fluorophenyl](2-fluorophenyl)-methanone, melting at 149–154° C.
5. 2-(1,2-benzisoxazol-3-yl)-5-chloro-benzaldehyde; starting from [4-chloro-2-(diethoxymethyl)phenyl](2-fluorophenyl)-methanone, melting at 178–179° C.
4-Fluoro-2-(5-fluoro-1,2-benzisoxazol-3-yl)-benzaldehyde; starting from [2-(diethoxymethyl)-5-fluorophenyl](2,5-difluorophenyl)-methanone, melting at 165–166° C.
6. 3-fluoro-6-(5-fluoro-1,2-benzisoxazol-3-yl)-benzaldehyde; starting from [2-(diethoxymethyl)-4-fluorophenyl](2,5-difluorophenyl)-methanone, melting at 167–173° C.
7. 2-(6-chloro-1,2-benzisoxazol-3-yl)-5-fluoro-benzaldehyde; starting from [2-(diethoxymethyl)-4-fluorophenyl](4-chloro-2-fluorophenyl)-methanone, melting at 188–192° C.
8. 3-chloro-6-(6-chloro-1,2-benzisoxazol-3-yl)-benzaldehyde; starting from [4-chloro-2-(diethoxymethyl)phenyl](4-chloro-2-fluorophenyl)-methanone, melting at 225–228° C.
9. 2-(6-trifluoromethyl-1,2-benzisoxazol-3-yl)-benzaldehyde; starting from [(2-diethoxymethyl)-4-trifluoromethylphenyl](2-fluorophenyl)-methanone, melting at 105–106° C.
10. 2-(1,2-benzisoxazol-3-yl)-benzaldehyde; starting from [(2-diethoxymethyl)phenyl](2-fluorophenyl)-methanone, melting at 149–155° C. 3-(1,2-benzisoxazol-3-yl)-benzaldehyde; starting from [(3-diethoxymethyl)phenyl](2-fluorophenyl)-methanone, $^{1}$H-NMR (200 MHz, DMSO-$d_6$) $d_H$ 10.15 (CHO),
11. 4-(1,2-benzisoxazol-3-yl)-benzaldehyde; starting from [(4-diethoxymethyl)phenyl](2-fluorophenyl)-methanone, melting at 116–117° C.

EXAMPLE 11

2-(1,2-Benzisoxazol-3-yl)-α-2-propenyl-benzenemethanamine hydrochloride

To a solution of 4.1 g of 2-(1,2-benzisoxazol-3-yl)-benzaldehyde in 50 ml of dry tetrahydrofuran, cooled at −78° C. under nitrogen atmosphere, were added 20 ml of a 1 M solution of lithium bis(trimethylsilyl)amide in hexane. The mixture was allowed to warm up to room temperature in a period of 1 h. After cooling to −78° C., this reaction mixture was added drop-wise to 20 ml of a 1 M solution of allylmagnesium bromide in tetrahydrofuran, cooled at −78° C., under a nitrogen atmosphere. The resulting suspension was allowed to warm up and stirred at room temperature for 2 h. Water was added and the mixture was extracted with ethyl acetate. The combined organic layers were washed with brine, dried over magnesium sulphate and evaporated to dryness under reduced pressure to yield 4.7 g of a solid. The compound was purified by chromatography on silica gel, eluting with 5% ethanol in toluene. The solid was dissolved in ethanol and triturated with a solution of hydrogen chloride in diethyl ether. The precipitated hydrochloride salt was filtered off and recrystallised from ethanol/diethyl ether/hexane, affording 2-(1,2-benzisoxazol-3-yl)-α-2-propenyl-benzenemethanamine hydrochloride, melting at 191° C.

In a similar way, the following compounds were prepared:
1. 2-(6-fluoro-1,2-benzisoxazol-3-yl)-a-2-propenyl-benzenemethanamine hydrochloride starting from 2-(6-fluoro-1,2-benzisoxazol-3-yl)-benzaldehyde, melting at 192–195° C.,
2. 2-(6-chloro-1,2-benzisoxazol-3-yl)-a-2-propenyl-benzenemethanamine hydrochloride starting from 2-(6-chloro-1,2-benzisoxazol-3-yl)-benzaldehyde, melting at 174–185° C.,
3. 2-(5-fluoro-1,2-benzisoxazol-3-yl)-a-2-propenyl-benzenemethanamine hydrochloride starting from 2-(5-fluoro-1,2-benzisoxazol-3-yl)-benzaldehyde, melting at 209–214° C.,
4. 2-(1,2-benzisoxazol-3-yl)-4-fluoro-a-2-propenyl-benzenemethanamine (E)-butenedioate (2:1 salt) starting from 2-(1,2-benzisoxazol-3-yl)-4-fluorobenzaldehyde, melting at 168–176° C.,
5. 2-(1,2-benzisoxazol-3-yl)-5-fluoro-a-2-propenyl-benzenemethanamine (E)-butenedioate starting from 2-(1,2-benzisoxazol-3-yl)-5-fluoro-benzaldehyde, melting at 176–180° C.,
6. 2-(1,2-benzisoxazol-3-yl)-5-chloro-a-2-propenyl-benzenemethanamine (E)-butenedioate starting from 2-(1,2-benzisoxazol-3-yl)-5-chloro-benzaldehyde, melting at 174–177° C.,
7. 3-fluoro-6-(5-fluoro-1,2-benzisoxazol-3-yl)-a-(2-propenyl)-benzene methanamine (E)-butenedioate starting from 3-fluoro-6-(5-fluoro-1,2-benzisoxazol-3-yl)-benzaldehyde, melting at 168–173° C.,
8. 4-fluoro-6-(5-fluoro-1,2-benzisoxazol-3-yl)-a-(2-propenyl)-benzenemethanamine (E)-butenedioate starting from 4-fluoro-6-(5-fluoro-1,2-benzisoxazol-3-yl)-benzaldehyde, melting at 164–169° C.,
9. 2-(6-chloro-1,2-benzisoxazol-3-yl)-5-fluoro-a-(2-propenyl)-benzenemethanamine (Z)-butenedioate starting from 2-(6-chloro-1,2-benzisoxazol-3-yl)-5-fluoro-benzaldehyde, melting at 162–164° C.,
10. 2-(6-trifluoromethyl-1,2-benzisoxazol-3-yl)-a-(2-propenyl)-benzene methanamine (E)-butenedioate starting from 2-(6-trifluoromethyl-1,2-benzisoxazol-3-yl)-5-fluoro-benzaldehyde, melting at 179–186° C., 11. 2-(1,2-benzisoxazol-3-yl)-a-(1-methyl-2-propenyl)-benzenemethanamine hydrochloride as a 8:2 mixture of diastereomers by $^1$H NMR starting from 2-(1,2-benzisoxazol-3-yl)-benzaldehyde and crotylmagnesium chloride, $^1$H-NMR (400 MHz, DMSO-d$_6$) d$_H$ 4.48, 4.42 (CHNH$_2$),
12. 2-(1,2-Benzisoxazol-3-yl)-a-(2-methyl-2-propenyl)-benzenemethanamine hydrochloride starting from 2-(1,2-benzisoxazol-3-yl)-benzaldehyde and 2-methyl-2-propenylmagnesium bromide, melting at 170–200° C.,
13. 3-(1,2-benzisoxazol-3-yl)-a-(2-propenyl)-benzenemethanamine (Z)-butenedioate starting from 3-(1,2-benzisoxazol-3-yl)-benzaldehyde, melting at 148–150° C.,

EXAMPLE 12

(R)-2-(1,2-Benzisoxazol-3-yl)-α-2-propenyl-benzenemethanamine hydrochloride

A total of 3 grams of 2-(1,2-Benzisoxazol-3-yl)-α-2-propenyl-benzenemethanamine was separated by chiral HPLC using a Chiracel OJ 250×4.6 mm column (Baker) and eluting with hexane/ethanol: 90/10, containing 0.1–0.2% diethylamine at a flow of 1 ml/min at room temperature. The first fractions were combined, evaporated to dryness under reduced pressure and converted into its hydrochloric acid salt by the addition of one equivalent hydrochloric acid in methanol. Recrystallisation from ethanol/diethyl ether afforded 1.02 g of (R)-2-(1,2-Benzisoxazol-3-yl)-α-2-propenyl-benzenemethanamine hydrochloride, melting at 191° C., α (c=0.5 in methanol): +19.0.

In a similar manner, the following compounds were resolved:
1. (R)-(+)-2-(6-fluoro-1,2-benzisoxazol-3-yl)-a-2-propenyl-benzenemethanamine hydrochloride, melting at 148–150° C., a (c=0.5 in methanol) +10.7,
2. (R)-(+)-2-(6-chloro-1,2-benzisoxazol-3-yl)-a-2-propenyl-benzenemethanamine hydrochloride, melting at 144–159° C., a (c=0.7 in methanol) +21.0,
3. (R)-(+)-2-(1,2-benzisoxazol-3-yl)-4-fluoro-a-2-propenyl-benzenemethanamine (E)-butenedioate, melting at 104–109° C., a (c=0.5 in methanol) +9.4,
4. (R)-(+)-2-(1,2-benzisoxazol-3-yl)-5-fluoro-a-2-propenyl-benzenemethanamine (E)-butenedioate, melting at 171–173° C., a (c=0.5 in methanol) +14.0,
5. (+)-2-(1,2-benzisoxazol-3-yl)-a-2-propynyl-benzenemethanamine (E)-butenedioate, melting at 165–170° C., a (c=0.7 in methanol) +9.4,
6. (+)-2-(6-chloro-1,2-benzisoxazol-3-yl)-a-2-propynyl-benzenemethanamine (E)-butenedioate (2:1 salt), melting at 176–179° C., a (c=0.5 in methanol) +20.7,

EXAMPLE 13

(S)-2-(1,2-Benzisoxazol-3-yl)-α-2-propenyl-benzenemethanamine hydrochloride

The second fractions of the chiral HPLC separation described under example 12 were combined, evaporated to dryness under reduced pressure and converted into its hydrochloric acid salt by the addition of one equivalent hydrochloric acid in methanol. Recrystallisation from ethanol/diethyl ether afforded 1.0 g of (S)-2-(1,2-Benzisoxazol-3-yl)-α-2-propenyl-benzenemethanamine hydrochloride, melting at 191° C., α (c=0.5 in methanol): –19.5.

In a similar manner, the following compounds were resolved:
1. (S)-(–)-2-(6-fluoro-1,2-benzisoxazol-3-yl)-a-2-propenyl-benzenemethanamine (E)-butenedioate, melting at 146–149° C., a (c=0.5 in methanol): –9.4,
2. (S)-(–)-2-(1,2-benzisoxazol-3-yl)-4-fluoro-a-2-propenyl-benzenemethanamine (E)-butenedioate, melting at 97–108° C., a (c=0.5 in methanol): –10.9,
3. (S)-(–)-2-(1,2-benzisoxazol-3-yl)-5-fluoro-a-2-propenyl-benzenemethanamine (E)-butenedioate, melting at 174–176° C., a (c=0.56 in methanol): –12.6,
4. (–)-2-(1,2-benzisoxazol-3-yl)-a-2-propynyl-benzenemethanamine (E)-butenedioate, melting at 161–169° C., a (c=0.8 in methanol) –10.4,
5. (–)-2-(6-chloro-1,2-benzisoxazol-3-yl)-a-2-propynyl-benzenemethanamine (E)-butenedioate (2:1 salt), melting at 198–202° C., a (c=0.5 in methanol) –19.7,

EXAMPLE 14

2-(1-Methyl-1H-indazol-3-yl)-αt-2-propenyl-benzenemethanamine hydrochloride

Starting from 0.6 g of 2-(1-methyl-1H-indazol-3-yl)-benzaldehyde, according to the procedure described for example 7, 0.48 g of 2-(1-methyl-1H-indazol-3-yl)-α-2-propenyl-benzenemethanamine hydrochloride was obtained as a solid, melting at 137° C.

EXAMPLE 15

2-(1,2-Benzisoxazol-3-yl)-α-butyl-benzenemethanamine hydrochloride

In a similar way, as described for example 11 2-(1,2-benzisoxazol-3-yl)-α-butyl-benzenemethanamine was prepared by using butyllithium in stead of allylmagnesium bromide. The hydrochloride salt melted at 152° C.

EXAMPLE 16

α-[2-(1,2-Benzisoxazol-3-yl)phenyl]-N-methyl-benzeneethanamine hydrochloride

A solution of 4.9 g of 2-(1,2-benzisoxazol-3-yl)-benzaldehyde in 250 ml of dry toluene, containing 20 g of 4 Å molecular sieves, is cooled to –10° C. Into this solution monomethylamine, dried over potassium hydroxide, was bubbled slowly during 0.5 h. After stirring at room temperature for 2 h, the solution was filtered. The filtrate was evaporated to dryness under reduced pressure, yielding 5.1 g of crude methylimine.

Alternatively, a mixture containing 2 g of 2-(1,2-Benzisoxazol-3-yl)-benzaldehyde, 0.96 g of benzylamine, a catalytic amount of p-toluenesulfonic acid and 50 ml of dry methanol was stirred at room temperature under nitrogen. After 3 h the mixture was evaporated to dryness under reduced pressure, water was added and the mixture was extracted several times with ethyl acetate. The organic layers were combined, washed with water, dried over magnesium sulphate and evaporated to dryness under reduced pressure, yielding 2.7 g of crude benzylimine.

Under a nitrogen atmosphere, 0.53 g of the crude methylimine (or alternatively 0.7 g of the crude benzylimine) dissolved in 10 ml of dry tetrahydrofuran, was added dropwise to a solution of 2.25 ml of a 2N solution of benzylmagnesium chloride in dry tetrahydrofuran diluted with 40 ml of dry tetrahydrofuran. The reaction mixture was stirred for 16 h at room temperature. An aqueous solution of ammonium chloride was added and the mixture extracted several times with ethyl acetate. The organic layers were combined, washed with water, dried over magnesium sulphate and evaporated to dryness under reduced pressure. The residue was purified by chromatography on silica gel, eluting with 1% ethyl acetate in heptane. This afforded 0.28 g of pure compound, which was dissolved in ethanol and converted into its hydrochloride salt by addition of a solution of hydrogen chloride in ethanol and precipitated by addition of diethyl ether. The precipitated salt was filtered off and recrystallised from ethanol/diethyl ether, affording 0.2 g of α-[2-(1,2-benzisoxazol-3-yl)phenyl]-N-methyl-benzeneethanamine hydrochloride, melting at 175° C.

In a similar way were prepared:
1. 2-(1,2-benzisoxazol-3-yl)-N-methyl-a-2-propenyl-benzenemethanamine: using methylamine and allylmagnesium bromide, M.S. (C.I.) (M/Z) : 279 [M+H]$^+$,
2. α-[2-(1,2-benzisoxazol-3-yl)phenyl]-N-benzyl-benzeneethanamine: using benzylamine and benzylmagnesium bromide, melting at 153° C.
3. 2-(1,2-benzisoxazol-3-yl)-N-benzyl-α-2-propenyl-benzenemethanamine: using benzylamine and allylmagnesium bromide, melting at 132° C.
4. 2-(1,2-benzisoxazol-3-yl)-N-phenylethyl-α-2-propenyl-benzenemethanamine: using phenylethylamine and allyl-magnesium bromide, M.S. (C.I.) (M/Z): 369 [M+H]$^+$.

EXAMPLE 17

(S)-N-[1-[2-(1,2-Benzisoxazol-3-yl)phenyl]-3-butenyl]-L-valine methyl ester

In 250 ml of ethanol, 28 g of 2-(1,2-benzisoxazol-3-yl)-benzaldehyde and 21 g of L-valine methyl ester hydrochloride were suspended. After addition of 17.5 ml of triethylamine the mixture was stirred at 40° C. for 16 h. The reaction mixture was evaporated to dryness under reduced pressure. To this residue 250 ml of dry diethyl ether were added. After stirring for 0.5 h at room temperature the precipitate was filtered off and the filtrate was evaporated to dryness under reduced pressure to afford 42 g of a solid.

Under an atmosphere of nitrogen, 36 g of this solid was dissolved in 270 ml of dry tetrahydrofuran, where after 13.95 g of zinc and 13.95 ml of allyl bromide were added. The mixture was stirred at room temperature for 16 h, after which the precipitate was filtered off. The filtrate was diluted with water and extracted several times with ethyl acetate. The combined organic layers were washed with water, dried over magnesium sulphate and evaporated to dryness under reduced pressure to yield 39.8 g of (S)-N-[1-[2-(1,2-benzisoxazol-3-yl)phenyl]-3-butenyl]-L-valine methyl ester as a solid.

In a similar way were prepared:
(S)-N-[1-[2-(6-chloro-1,2-benzisoxazol-3-yl)phenyl]-3-butenyl]-L-valine methyl ester; starting from 2-(6-chloro-1,2-benzisoxazol-3-yl)-benzaldehyde.
(S)-N-[1-[2-(6-fluoro-1,2-benzisoxazol-3-yl)phenyl]-3-butenyl]-L-valine methyl ester; starting from 2-(6-fluoro-1,2-benzisoxazol-3-yl)-benzaldehyde.

EXAMPLE 18

[S-(R*,R*)]-2-[[1-[2-(1,2-Benzisoxazol-3-yl)phenyl]-3-butenyl]amino]-3-methyl-1-butanol Under an atmosphere of nitrogen, 5.6 g of lithium aluminum hydride were added to 500 ml of dry tetrahydrofuran. The mixture was cooled to −10° C. and a solution of 30 g of (S)-N-[1-[2-(1,2-benzisoxazol-3-yl)phenyl]-3-butenyl]-L-valine methyl ester in 500 ml of dry tetrahydrofuran was added slowly. The mixture was stirred at −10° C. for 16 h, after which 22 ml of water was slowly added. After stirring at room temperature for 0.5 h, magnesium sulphate was added. The solids were filtered off and the filtrate was evaporated to dryness under reduced pressure to yield 25 g of [S-(R*,R*)]-2-[[1[2-(1,2-benzisoxazol3-yl)phenyl]-3-butenyl]amino]-3-methyl-1-butanol.

In a similar way were prepared:
[S-(R*, R*)]-2-{{1-[2-(6-Chloro-1,2-benzisoxazol-3-yl)phenyl]-3-butenyl]amino]-3-methyl-1-butanol; starting from (S)-N-[1-[2-(6-chloro-1,2-benzisoxazol-3-yl)phenyl]-3-butenyl]-L-valine methyl ester.
[S-(R*, R*)]-2-{{1-[2-(6-fluoro-1,2-benzisoxazol-3-yl)phenyl]-3-butenyl]amino]-3-methyl-1-butanol; starting from (S)-N-[1-[2-(6-fluoro-1,2-benzisoxazol-3-yl)phenyl]-3-butenyl]-L-valine methyl ester.

EXAMPLE 19

(S)-2-(1,2-Benzisoxazol-3-yl)-α-2-propenyl-benzenemethanamine hydrochloride

To a solution of 18 g of [S-(R*,R*)]-2-[[1-[2-(1,2-benzisoxazol-3-yl)phenyl]-3-butenyl]amino]-3-methyl-1-butanol in 310 ml of methanol were added 34.4 ml of 40% aqueous methylamine and 276 ml of water. To this mixture was slowly added 61.6 g of periodic acid. After stirring at room temperature for 4 h, the mixture was extracted several times with diethyl ether. To the combined organic layers were added 100 ml of 4N aqueous HCl. The amount of diethyl ether was reduced under reduced pressure to 20% of its original volume. After stirring at room temperature for 0.5 h, the remaining mixture was cooled to 0° C.–5° C. and the pH was adjusted to 7 by the addition of 4N aqueous sodium hydroxide. The mixture was extracted several times with ethyl acetate. The combined organic layers were washed with water, dried over magnesium sulphate and evaporated to dryness under reduced pressure to yield 14 g of a solid. This solid was dissolved in ethanol and a solution of hydrogen chloride in ethanol was added until the pH of the resulting solution was slightly acidic. The mixture was evaporated to dryness under reduced pressure and the resulting residue was dissolved in 25 ml of dry ethanol and 50 ml of dry diethyl ether were added. After stirring at room temperature for 16 h, the precipitate was collected and dried to yield 6.5 g of a solid which was recrystallised from ethanol/diethyl ether to afford 6.2 g of pure (S)-2-(1,2-benzisoxazol-3-yl)-α-2-propenyl-benzenemethanamine hydrochloride, mp 191° C., α (c=0.5 in methanol): −19.5.

In a similar way were prepared:
1. (S)-(−)-2-(6-fluoro-1,2-benzisoxazol-3-yl)-a-2-propenyl-benzenemethanamine hydrochloride, melting at 166–174° C., a (c=0.4 in methanol) : −11.2,
2. (S)-(−)-2-(6-chloro-1,2-benzisoxazol-3-yl)-a-2-propenyl-benzenemethanamine hydrochloride, melting at 169–178° C., a (c=0.9 in methanol) −7.8.

EXAMPLE 20

2-(1,2-Benzisoxazol-3-yl)-N,N-dimethyl-benzenemethanamine hydrochloride

In one portion, a total of 2.0 g of 2-(1,2-benzisoxazol-3-yl)-benzaldehyde was added to a solution of 8.0 g of dimethylamine hydrochloride in 70 ml of methanol. The reaction mixture was stirred at room temperature for 16 h, after which 2.0 g of sodium borohydride were added. After stirring at room temperature for another 24 h, the solids were filtered off, and the residue was washed with dichloromethane. The combined filtrate was dried over magnesium sulphate and evaporated to dryness under reduced pressure. The resulting solid was purified by chromatography on silica gel, eluting with ethyl acetate, affording 0.89 g. This solid was dissolved in ethyl acetate, and triturated with a solution of hydrogen chloride in methanol. This solution was evaporated to dryness under reduced pressure and the residue was crystallised from ethanol/diethyl ether/hexane, yielding 0.54 g of pure 2-(1,2-benzisoxazol-3-yl)-N, N-dimethyl-benzenemethanamine hydrochloride, melting at 190° C.

EXAMPLE 21

The intermediate imines, prepared by using primary amines, can be isolated as described under example 16, prior to the reduction with sodium borohydride.

In a similar way were prepared:
1. 2-(1,2-benzisoxazol-3-yl)-N-methyl-benzenemethanamine hydrochloride, melting at 230° C.,
2. 2-(1,2-benzisoxazol-3-yl)-N-2-propenyl-benzenemethanamine hydrochloride, melting at 176° C.,
3. 2-(1,2-benzisoxazol-3-yl)-N-benzyl-benzenemethanamine ethanedioate, melting at 165° C.,
4. 2-(1,2-benzisoxazol-3-yl)-N-[(2-methoxyphenyl)methyl]-benzenemethanamine ethanedioate, melting at 184° C.,
5. 2-(1,2-benzisoxazol-3-yl)-N-[[4-(1,2,3-thiazol-4-yl)phenyl]methyl]-benzenemethanamine hydrochloride, melting at 176° C.,
6. N-[[2-(1,2-benzisoxazol-3-yl)phenyl]methyl]-3-pyridinemethanamine dihydrochloride, melting at 154° C.,
7. N-[[2-(1,2-benzisoxazol-3-yl)phenyl]methyl]-benzeneethanamine hydrochloride, melting at 192° C.

EXAMPLE 22

2-(1,2-Benzisoxazol-3-yl)-N-[[2-(1,2-benzisoxazol-3-yl)phenyl]methyl]-benzenemethanamine A mixture of 2.0 g of 2-(1,2-benzisoxazol-3-yl)-benzaldehyde and 7.0 of ammonium acetate in 200 ml of dry methanol was refluxed in the presence of 3 Å molecular sieves for 12 h, after which 2.0 g of sodium borohydride were added. After stirring at room temperature for another 24 h, the solids were filtered off, and the residue was washed with dichloromethane. The combined filtrate was dried over magnesium sulphate and evaporated to dryness under reduced pressure to afford 3.5 g of an oil. Crystallisation from diethyl ether yielded 1.7 g of 2-(1,2-benzisoxazol-3-yl)-N-[[2-(1,2-benzisoxazol-3-yl)phenyl]methyl]-benzenemethanamine, melting at 138° C.

EXAMPLE 23

α-Amino-2-(1,2-benzisoxazol-3-yl)-benzeneacetonitrile [Z]-2-butenedioate

In 40 ml of water 10 g of sodium cyanide and 11 g of ammonium chloride were dissolved. A suspension of 44.6 g of 2-(1,2-benzisoxazol-3-yl)-benzaldehyde in 40 ml of methanol was added and the resulting reaction mixture was stirred vigorously for 2 h. A total of 100 ml of water were added and the mixture was extracted several times with toluene. The combined organic layers were washed with water and extracted with two 200 ml portions of 2N HCl. The aqueous layers were combined, the pH adjusted to pH 7 with sodium hydrogencarbonate and the resulting mixture was extracted several times with diethyl ether. The combined organic layers were dried over magnesium sulphate and evaporated to dryness under reduced pressure to afford 4.7 g of a solid, which was dissolved in diethyl ether. To this solution 2.2 g of maleic acid dissolved in diethyl ether was added. The precipitate formed was filtered off and dried to yield 3 g of α-amino-2-(1,2-benzisoxazol-3-yl)-benzeneacetonitrile [Z]-2-butenedioate, melting at 126° C.

EXAMPLE 24

Methyl α-amino-2-(1,2-benzisoxazol-3-yl)-benzeneacetate

To a mixture of 6 ml of concentrated hydrochloric acid and 6 ml of water was added 2.0 g of α-amino-2-(1,2-benzisoxazol-3-yl)-benzeneacetonitrile [Z]-2-butenedioate. This mixture was heated at reflux for 20 h, cooled to room temperature and the pH adjusted to 8 with concentrated aqueous ammonia. The precipitate was filtered off, washed with water and dissolved in 1N aqueous sodium hydroxide. This solution was washed with diethyl ether, neutralised with 2N aqueous hydrochloric acid and extracted several times with diethyl ether. The combined organic layers were washed with water, dried over magnesium sulphate and evaporate to dryness. The residue was dissolved in a mixture of 8 ml of 1N aqueous sodium hydroxide and 5 ml of ethanol, 0.5 g of decolourising charcoal was added, the mixture was heated on a steam bath, and filtered. The filtrate was acidified with 5N aqueous hydrochloric acid. The precipitate formed was filtered off and washed with water. The aminoacid obtained was not purified further, but was dissolved in 20 ml of dry diethyl ether. Into this solution was bubbled diazomethane, obtained by adding 33% aqueous sodium hydroxide to a suspension of 1 g of N-methyl-N-nitroso-p-toluenesulphonamide in 6 ml of ethanol. After stirring the reaction mixture at room temperature for 2 h under nitrogen, 1 ml of concentrated acetic acid was added. After 0.5 h at room temperature, 50 ml of 2N aqueous sodium carbonate was added. The organic layer was collected, washed with water, dried over magnesium sulphate and evaporated to dryness to yield 0.6 g of methyl α-amino-2-(1,2-benzisoxazol-3-yl)-benzeneacetate.

EXAMPLE 25

2-(1,2-Benzisoxazol-3-yl)-benzenemethanol

A suspension of 10 g of 2-(1,2-benzisoxazol-3-yl)-benzaldehyde and 3.4 g of sodium borohydride in 800 ml of ethanol was stirred for 16 h under an atmosphere of nitrogen. Water was added and the mixture was extracted with dichloromethane. The combined organic layers were washed with brine, dried over magnesium sulphate and evaporated to dryness under reduced pressure to yield 8.5 g of a solid, which was purified by chromatography on silica gel, eluting with 1% of ethyl acetate in hexane, affording 7.0 g of 2-(1,2-benzisoxazol-3-yl)-benzenemethanol, melting at 55° C.

EXAMPLE 26

2-(1,2-Benzisoxazol-3-yl)-α-2-propenyl-benzenemethanol

To 5 ml of acetic acid were added 3.0 g of zinc wool and 0.3 g of copper(II) acetate monohydrate. This mixture was stirred at room temperature for 0.5 h. The solids were filtered off and washed with diethyl ether and tetrahydrofuran. This solid was suspended in 15 ml of tetrahydrofuran and a solution of 5.0 g of 2-(1,2-benzisoxazol-3-yl)-benzaldehyde and 3.75 g of propargyl bromide in 15 ml of tetrahydrofuran was added slowly. The resulting mixture was heated at reflux for 1 h, cooled to room temperature and quenched with 10 ml of 2N aqueous hydrochloric acid. The resulting mixture was extracted several times with diethyl ether, the combined organic layers were washed with water, dried over magnesium sulphate and evaporated to dryness under reduced pressure to afford 4.8 g of 2-(1,2-benzisoxazol-3-yl)-α-2-propenyl-benzenemethanol as an oil, M.S. (C.I.) (M/Z) 264 $[M+H]^+$, 246 (100%) $[M+H–H_2O]^+$.

EXAMPLE 27

2-(1,2-Benzisoxazol-3-yl)-α-methyl-benzenemethanol

In 500 ml of dry diethyl ether were dissolved 9.25 g of 2,6-di-tert-butyl-4-methylphenol under nitrogen. To this solution were slowly added 21 ml of a 2M solution of trimethylaluminium in toluene. The mixture was stirred at room temperature for 1 h after which a solution of 6.25 g of 2-(1,2-benzisoxazol-3-yl)-benzaldehyde in 500 ml of dry toluene was slowly added. After stirring the mixture at room temperature for 60 h, water was slowly added and the mixture was extracted several times with diethyl ether. The combined organic layers were washed with water, dried over magnesium sulphate and evaporated to dryness under reduced pressure to afford 13.8 g of a solid which was purified by chromatography on silica gel, eluting with toluene, to afford 5.0 g of 2-(1,2-benzisoxazol-3-yl)-α-methyl-benzenemethanol, M.S. (C.I.) (M/Z) : 240 $[M+H]^+$, 222 (100%) $[M+H–H_2O]^+$.

EXAMPLE 28

1-[2-(1,2-Benzisoxazol-3-yl)phenyl]-ethanone

In 46 ml of dry pyridine was dissolved 4.6 g of 2-(1,2-benzisoxazol-3-yl)-α-methyl-benzenemethanol. Under an atmosphere of nitrogen, 4.6 g of chromium trioxide was slowly added at room temperature. After stirring at room temperature for 4 h, 200 ml of diethyl ether were added to the reaction mixture. The precipitates were filtered off and washed with diethyl ether. The filtrate was washed with 5 portions of 100 ml of 2N aqueous hydrochloric acid and 2 portions of 200 ml of water, dried over magnesium sulphate and evaporated to dryness to afford 4.5 g of 1-[2-(1,2-benzisoxazol-3-yl)phenyl]-ethanone, melting at 108° C.

EXAMPLE 29

2-(1,2-Benzisoxazol-3-yl)-α,N-dimethyl-benzenemethanamine ethanedioate

To a solution of 2 grams of 1-[2-(1,2-benzisoxazol-3-yl) phenyl]-ethanone in 20 ml of dry diethyl ether were added 20 ml of monomethylamine at −78° C. After the addition of 2 ml of titanium tetrachloride, the reaction mixture was allowed to warm up. After stirring at room temperature for another 16 h, the precipitate was filtered off. The resulting filtrate was evaporated to dryness to afford 1.8 g of an oil. Under an atmosphere of nitrogen the oil obtained was dissolved in 100 ml of dry ethanol and 1.5 g of sodium borohydride were added slowly. After stirring at room temperature for 48 h, the solids were filtered off, and the residue was washed with dichloromethane. The combined filtrate was dried over magnesium sulphate and evaporated to dryness under reduced pressure, to afford 1.67 of a solid which was dissolved in 5 ml of dry ethanol and treated with a solution of 0.84 g of ethanedioic acid in ethanol. The precipitate was filtered off and recrystallised from ethanol to afford 2.0 g of 2-(1,2-benzisoxazol-3-yl)-α,N-dimethyl-benzenemethanamine ethanedioate, melting at 185° C.

EXAMPLE 30

2-[[2-(1,2-Benzisoxazol-3-yl)phenyl]methyl]-1H-isoindole-1,3(2H)-dione

Under an atmosphere of nitrogen, 24 ml of methanesulfonyl chloride were added drop-wise to a solution of 6.6 g of 2-(1,2-benzisoxazol-3-yl)-benzenemethanol in 100 ml of dry dichloromethane at 0° C. After stirring the reaction mixture at room temperature for 4 h, water was added. The organic layer was collected, washed with brine, dried over magnesium sulphate and evaporated to dryness under reduced pressure to yield a solid, which was purified by chromatography on silica gel, eluting with 20% of ethyl acetate in heptane, affording 4 g of a solid.

This solid was dissolved in 100 ml of dry N,N,-dimethylformamide and 3.2 g of potassium phtalimide were added. The reaction mixture was heated at 100° C. under nitrogen for 3 h. After cooling to room temperature the mixture was pored into ice-water and extracted several times with ethyl acetate. The combined organic layers were washed with brine, dried over magnesium sulphate and evaporated to dryness under reduced pressure to yield 5.3 g of a solid, which was crystallised from ethyl acetate/diethyl ether, affording 4.9 g of 2-[[2-(1,2-benzisoxazol-3-yl) phenyl]methyl]-1H-isoindole-1,3(2H)-dione, melting at 142° C.

EXAMPLE 31

2-(1,2-Benzisoxazol-3-yl)-benzenemethanamine hydrochloride

A mixture of 100 ml of dry ethanol, 4.8 g of 2-[[2-(1,2-benzisoxazol-3-yl)phenyl]methyl]-1H-isoindole-1,3(2H)-dione and 4.1 g of hydrazine monohydrate was refluxed for 4 h. After cooling to room temperature, ethyl acetate and 1 N aqueous sodium hydroxide were added. The organic layer was collected, washed with brine, dried over magnesium sulphate and evaporated to dryness under reduced pressure to yield a solid, which was triturated with a solution of hydrochloric acid in methanol. Crystallisation from ethyl acetate/ethanol/diethyl ether, afforded 2.2 g of 2-(1,2-benzisoxazol3-yl)-benzenemethanamine hydrochloride, melting at 233° C.

EXAMPLE 32

3-[2-(1-Azido-3-butynyl)phenyl]-1,2-benzisoxazole

A mixture containing 4.0 g of 2-(1,2-benzisoxazol-3-yl)-α-2-propenyl-benzenemethanol, 4.32 g of triphenylphosphine, 2.61 g of diethyl azodicarboxylate and 4.12 g of diphenylphosphoryl azide in 50 ml of benzene was stirred at room temperature for 24 h. Evaporation of the solvent under reduced pressure afforded a solid which was purified by chromatography on silica gel, eluting with 5% ethanol in toluene, to afford 1.5 g of 3-[2-(1-azido-3-butynyl)phenyl]-1,2-benzisoxazole as an oil, M.S. (C.I.) (M/Z): 289 $[M+H]^+$.

EXAMPLE 33

2-(1,2-Benzisoxazol-3-yl)-α-2-propynyl-benzenemethanamine ethanedioate

A mixture containing 1.0 g of 3-[2-(1-azido-3-butynyl) phenyl]-1,2-benzisoxazole, 1.0 g of triphenylphosphine, 10 ml of diethyl ether, 10 ml of tetrahydrofuran and 5 ml of water was stirred at room temperature for 16 h. Water was added and the mixture extracted several times with diethyl ether. The organic layers were combined, washed with brine, dried over magnesium sulphate and evaporated to dryness under reduced pressure. The residue was dissolved in a mixture of diethyl ether/ethyl acetate and treated with 0.32 g of oxalic acid. The precipitate was filtered off and dried to afford 0.82 g of 2-(1,2-benzisoxazol-3-yl)-α-2-propynyl-benzenemethanamine ethanedioate, melting point >250° C.

EXAMPLE 34

2-[2-(1,2-Benzisoxazol-3-yl)-benzylamino]-3-phenyl-propionamide

To a solution of 3.87 g of N-fluorenylmethoxycarbonyl-L-phenyl-propionamide (Fmoc—LPhe—OH, Bachem) in a mixture of 25 ml of dichloromethane and 15 ml of N,N-dimethylformamide was added 0.63 g of diisopropylcarbodiimide. After stirring for 0.5 h, dichloromethane was removed by evaporation and 0.5 g of Wang resin (Bachem, loading 0.98 mmol/g) suspended in 10 ml of N,N-dimethylformamide was added. The suspension was stirred for 1 h at room temperature, the resin was filtered and washed with 5×10 ml of N,N-dimethylformamide. The resin was suspended in 10 ml of 25% piperidine in N,N-dimethylformamide and stirred for 10 min. The resin was filtered and resuspended in 10 ml of 25% piperidine in N,N-dimethylformamide and stirred for 10 min. The resin was filtered and washed with N,N-dimethylformamide until neutral.

The resin was suspended in 5 ml of N,N-dimethylformamide, 400 mg of 2-(1,2-benzisoxazol-3-yl)-benzaldehyde was added, followed by 15 ml of trimethyl orthoformate, and the resulting suspension was stirred for 1 h. Then 330 mg sodium cyanoborohydride was added, followed, after 15 min, by 400 μl of acetic acid. After stirring for 1 h, the resin was filtered and washed with 5×10 ml of N,N-dimethylformamide and 5×10 ml of ethanol. To the resin was added 1 ml of N,N-dimethylformamide and 10 ml of a 9 M solution of methylamine in methanol, and the suspension was stirred overnight. The resin was filtered and washed with 3×5 ml of methanol. The combined filtrate and washings were evaporated till dryness. The resulting material was dissolved in 0.1 M hydrochloric acid and lyophilized, yielding 120 mg of 2-[2-(1,2-benzisoxazol-3-yl)-benzylamino]-3-phenyl-propionamide (65%, FAB-MS [M+H] 385, about 20% of dialkylated material present ([M−H] 608). This material can be purified by preparative HPLC.

EXAMPLE 35

2-(1,2-benzisoxazol-3-yl)-a-methyl-a-(2-propenyl)-benzene methanamine (E)-butenedioate (2-Bromophenyl)(4-methyl-2,6,7-trioxabicyclo[2.2.2]octane)methane A suspension of 25.6 g of 2-bromophenylacetic acid in 100 ml of thionyl chloride was refluxed for 3 h. The excess thionyl chloride was removed under reduced pressure to give 30 g of the crude intermediate 2-bromophenylacetoyl chloride as an oil. This crude acid chloride was dissolved in 100 ml of methylene chloride and added to a solution of 19.3 ml of pyridine and 12.5 ml of 3-methyl-3-oxetanemethanol in 300 ml of methylene chloride at 0° C. The solution was stirred at 0° C. for 1 h then warmed to room temperature and stirred for 4 h. The reaction was diluted with 600 ml of methylene chloride then washed with 400 ml each of water, 2M hydrochloric acid, 5% sodium carbonate solution, water and brine. The organic layer was dried over sodium sulfate and evaporated to give 33.8 g of the crude 3-methyl-3-oxetanemethyl 2-bromophenylacetate. This crude ester was dissolved in 100 ml of methylene chloride and cooled to 0° C. To this solution was added 7 ml of boron trifluoride etherate, the solution was stirred for 1 h then quenched by the addition of 30 ml of triethylamine followed by 300 ml of ether. The crystalline solid was filtered off and the filtrate evaporated to yield 34.8 g of (2-bromophenyl)(4-methyl-2,6,7-trioxabicyclo[2.2.2]octane)methane as a gum which slowly solidifies, GC-M.S. (E.I.) (M/Z): 298 [M]⁺.

(2-fluorophenyl)[(4-methyl-2,6,7-trioxabicyclo[2.2.2] octane)methyl]-methanone

A mechanically stirred solution of 27.4 g of (2-bromophenyl)(4-methyl-2,6,7-trioxabicyclo[2.2.2] octane)methane in 500 ml of tetrahydrofuran was cooled to −65° C. To this cold solution was added rapidly 67 ml of a 1.5 M solution of butyllithium in hexane. The solution was warmed to −20° C. and stirred for 20 min. The solution was cooled down to −40° C. and a solution of 17.2 g 2-fluorobenzaldehyde in 50 ml of tetrahydrofuran added by cannular. The solution was warmed to 0° C. and stirred for 1.5 h then quenched by the addition of 200 ml of water and 100 ml of ether was added. The organic layer was separated and the aqueous layer extracted with 100 ml of ether. The combined organic layers were dried over sodium sulfate and evaporated to yield 30.9 g of crude [(4-methyl-2,6,7-trioxabicyclo[2.2.2]octane)methyl]-α-(2-fluorophenyl)-benzene methanol as a gum which solidifies. To this material was added 400 ml toluene and 138.3 g of manganese dioxide. The suspension was refluxed overnight under Dean-Stark conditions then cooled to room temperature and filtered through dicalite. The residue was washed with 200 ml of tetrahydrofuran and the filtrates evaporated to yield 20.4 g of (2-fluorophenyl)[(4-methyl-2,6,7-trioxabicyclo[2.2.2] octane)methyl]-methanone as a gum, GC-M.S. (E.I.) (M/Z): 342 [M]⁺.

Ethyl [2-(1,2-benzisoxazol-3-yl)-phenyl]acetate

To a solution of 4.78 g of acetone oxime in 250 ml of tetrahydrofuran was added 7.38 g of potassium tert-butoxide. The suspension was stirred for 20 min then a solution of 20.4 g of (2-fluorophenyl)[(4-methyl-2,6,7-trioxabicyclo[2.2.2]octane)methyl]-methanone in 100 ml of tetrahydrofuran was added and the solution refluxed for 18 h. The solution was cooled to room temperature and diluted with 200 ml of water then extracted with two 500 ml portions of ethyl acetate. The combined organic layers were washed with 200 ml of brine then dried over sodium sulfate and evaporated to yield 22.1 g of crude O-[(2-(4-methyl-2, 6,7-trioxabicyclo[2.2.2]octane)methyl) benzoylphenyl] oxime 2-propanone. To a solution of 9.2 g of the crude O-[(2-(4-methyl-2,6,7-rioxabicyclo[2.2.2]octane)ethyl)-benzoylphenyl] oxime 2-propanone in 100 ml of ethanol was added 15 ml of concentrated sulfuric acid with exteme caution. The solution was refluxed for 45 min then cooled to room temperature then poured onto ice and extracted with two 500 ml portions of ether. The combined organic layers were dried over sodium sulfate and evaporated to a brown gum which was purified twice by flash chromatography eluting with methylene chloride then with heptane-acetone (4:1) to give 1.01 g of ethyl [2-(1,2-benzisoxazol-3-yl)-phenyl]acetate as an oil, GC-M.S. (E.I.) (M/Z): 281 [M]$^+$.

Ethyl 2-[2-(1,2-benzisoxazol-3-yl) phenyl]-2-methyl-4-pentenoate

A solution of 0.75 ml of diisopropylamine in 15 ml of tetrahydrofuran was cooled to 0° C. and 3.55 ml of a 1.5 M solution of butyllithium in hexane was added dropwise. The solution was stirred at this temperature for 10 min then cooled below −60° C. with an acetone-cardice bath and a solution of 1 g of ethyl [2-(1,2-benzisoxazol-3-yl)-phenyl] acetate dissolved in 10 ml of tetrahydrofuran was added dropwise. The deep orange coloured solution was stirred for 45 min then 0.45 ml of allyl bromide was added dropwise. The solution was stirred at a temperature below −60° C. for 0.5 h then warmed up to below 0° C. over 0.5 h and stirred at this temperature for 1.5 h. The reaction was quenched by the addition of 20 ml of saturated ammonium chloride solution then extracted with three 50 ml portions of ether which were dried over sodium sulfate. Evaporation followed by flash chromatography eluting with 8:2 heptane-ethyl acetate afforded 0.91 g of the intermediate ethyl 1-[2-(1,2-benzisoxazol-3-yl)-phenyl]-4-pentenoate as a pale yellow gum. A solution of 0.9 g of this intermediate dissolved in 5 ml of tetrahydrofuran was added to a solution of lithium diisopropylamide prepared from 15 ml of tetrahydrofuran, 2.8 ml of a 1.5 M solution of butyllithium in hexane and 0.55 ml of diisopropylamine and the mixture was stirred at a temperature below −60° C. (acetone-cardice bath). The solution was stirred for 45 min then methyl iodide was added and the solution stirred at this temperature for 10 min. The solution was warmed to 0° C. over 15 min then stirred at this temperature for 1.25 h. The reaction was quenched by the addition of 20 ml of saturated ammonium chloride solution then extracted with three 50 ml portions of ether which were dried over sodium sulfate. Evaporation followed by flash chromatography eluting with 8:2 heptane-ethyl acetate afforded 0.76 g of ethyl 1-[2-(1,2-benzisoxazol-3-yl)-phenyl]-1-methyl-4-pentenoate as a pale yellow gum, GC-M.S. (E.I.) (M/Z): 334 [M−H]$^+$; $\delta_H$ (400 MHz; CDCl$_3$) 1.61 (CH$_3$)

2-[2-(1,2-Benzisoxazol-3-yl)-2-methyl-4-pentenoic acid

To a solution of 0.75 g of ethyl 2-[2-(1,2-benzisoxazol-3-yl)-phenyl]-2-methyl-4-pentenoate in 10 ml of 2-methoxyethanol was added 5 ml of 10M potassium hydroxide solution. The solution was refluxed overnight then cooled to room temperature and poured onto ice. This aqueous solution was acidified with 5M hydrochloric acid and extracted with three 100 ml portions of ether. The extracts were evaporated and azeotroped with toluene. Flash chromatography of the residue, eluting with 0 to 10% methanol in methylene chloride, afforded 0.52 g of 2-[2-(1,2-benzisoxazol-3-yl)-phenyl]-2-methyl-4-pentenoic acid as a gum, $^1$H NMR (400 MHz; CDCl$_3$) $\delta_H$ 1.52 (Me).

2-(1,2-benzisoxazol-3-yl)-a-methyl-a-(2-propenyl)-benzene methanamine (E)-butenedioate To a solution of 2-[2-(1,2-benzisoxazol-3-yl)phenyl]-2-methyl-4-pentenoic acid in 5 ml of toluene was added 0.36 ml of diphenylphosphoryl azide and 0.24 ml of triethylamine. The solution was stirred at 90° C. for 1 h then diluted with 50 ml of toluene and washed with 25 ml each of 2M hydrochloric acid, 5% sodium carbonate and brine. The solution was evaporated to 0.55 g of a partially solid gum. A sample of 0.21 g of this material was treated with 3 ml of 2-methoxyethanol and 2 ml of 10M potassium hydroxide solution. This solution was refluxed overnight then cooled to room temperature, diluted with 10 ml of water and extracted with three 25 ml portions of methylene chloride. The combined organic layers were washed with 50 ml of brine, evaporated and azeotroped with toluene. Flash chromatography, eluting with a 9:1 mixture of methylene chloride-methanol, afforded 68 mg of product. This was converted to the (E)-butenedioate salt and crystalised from methanol-ether to give 78 mg of 2-(1,2-benzisoxazol-3-yl)-a-methyl-a-(2-propenyl)-benzenemethanamine (E)-butenedioate melting at 196–200° C.

EXAMPLE 36

2-(1,2-Benzisoxazol-3-yl)-a-(4-fluorobenzyl)-benzenemethanamine hydrochloride.

To a stirred suspension of 2.23 g of 2-(1,2-benzisoxazol-3-yl)-benzaldehyde and 2.6 g of magnesium sulfate in 25 ml of methylene chloride was added 1.7 ml of diphenylmethanamine and the stirring continued overnight. The reaction was filtered through dicalite and the filtrate evaporated to give 3.9 g crude N-[2-(1,2-benzisoxazol-3-yl)-benzylidene]-1,1-diphenylmethanamine as a gum which slowly solidified. A stirred solution of 0.75 g of N-[2-(1,2-benzisoxazol-3-yl)-benzylidene]-1,1-diphenylmethanamine in 15 ml tetrahydrofuran was cooled to −65° C. and 2.5 ml of a 1M solution of potassium tert-butoxide in tetrahydrofuran was added dropwise. The purple coloured solution was stirred for 5 min then 4-fluorobenzyl bromide was added rapidly and the reaction allowed to slowly warm to room temperature. The reaction was diluted with 25 ml of water then extracted with 100 ml then 50 ml of methylene chloride. The combined organic extracts were dried over sodium sulphate then evaporated to give 1.18 g of crude N-(diphenylmethylidene)-2-(1,2-Benzisoxazol-3-yl)-a-(4-fluorobenzyl)-benzenemethanamine which was not characterised due to instability. To a solution of 1.1 g of N-(diphenylmethylidene)-2-(1,2-benzisoxazol-3-yl)-a-(4-fluorobenzyl)-benzenemethanamine in 20 ml of acetone was added 9 ml of 1 M hydrochloric acid. The solution was stirred overnight then evaporated and 15 ml of 4M sodium hydroxide solution added. The solution was extracted with 100 ml then 50 ml of methylene chloride. The organic extracts were dried and evaporated to an oil which was purified by flash chromatography eluting with a 19:1 mixture of methylene chloride-methanol to yield the pure amine free base which was dissolved in methanol and acidified with a solution of hydrogen chloride in methanol, evaporated and crystalised from methanol-ether to yield 0.18 g of 2-(1,2-benzisoxazol-3-yl)-a-(4-fluorobenzyl)-benzenemethanamine hydrochloride, melting at 238–241° C.

The following primary amines salts were similarly prepared:

1. 2-(1,2-benzisoxazol-3-yl)-a-benzyl-benzenemethanamine hydrochloride, melting at 210–246° C. (dec),
2. 2-(1,2-benzisoxazol-3-yl)-a-[(thien-3-yl)-methyl)-benzenemethanamine hydrochloride employing 3-(bromomethyl)thiophene (prepared by the method reported by E. Campaigne and B. F. Tullar in "Organic Synthesis", Coll. Vol. IV, 1963, pp 921 and using carbon tetrachloride in place of benzene), melting at 264–267° C.
3. 2-(1,2-benzisoxazol-3-yl)-a-(3-methyl-2-butenyl)-benzenemethanamine (Z)-butenedioate employing 4-bromo-2-methyl-2-butene, melting at 132–135° C.,
4. 2-(1,2-benzisoxazol-3-yl)-a-(2-butenyl)-benzenemethanamine hydrochloride as a 3:7 mixture of E/Z geometrical isomers employing 1-bromo-2-butene, $^1$H-NMR (400 MHz, DMSO-d$_6$) d$_H$ 1.38 (CH$_3$), 1.34 (CH$_3$), 5. 2-(1,2-benzisoxazol-3-yl)-a-(3-butenyl)-benzenemethanamine hydrochloride employing 1-iodo-3-butene (prepared by the method of L. Kaplan, *J. Chem Soc., Chem. Commun.*, 1968, 754), $^1$H-NMR (400 MHz, DMSO-d$_6$) d$_H$ 4.55 (CHNH$_2$).
6. 2-(1,2-benzisoxazol-3-yl)-a-(cyclopropylmethyl)-benzenemethanamine hydrochloride employing cyclopropylmethyl iodide (prepared by the method of J. San Filippo, Jr., J. Silbermann and P. J. Fagan, *J. Am. Chem. Soc.*, 1978, 100, 4834), $^1$H-NMR (400 MHz, DMSO-d$_6$) dH 4.62 (CHNH$_2$).
7. 2-(1,2-benzisoxazol-3-yl)-a-(2-chloropropenyl)-benzenemethanamine hydrochloride employing 2,3-dichloro-1-propene, $^1$H-NMR (400 MHz, DMSO-d$_6$) d$^H$ 4.93 (CHNH$_2$),
8. 2-(1,2-benzisoxazol-3-yl)-a-(4,4,4-trifluorobutyl)-benzenemethanamine (E)-butenedioate starting from 2-(6-chloro-1,2-benzisoxazol-3-yl)-benzaldehyde and employing 1-iodo-4,4,4-trifluorobutane, melting at 203–210° C.,
9. 2-(6-chloro-1,2-benzisoxazol-3-yl)-a-butyl-benzenemethanamine hydrochloride starting from 2-(6-chloro-1,2-benzisoxazol-3-yl)-benzaldehyde and employing butyl iodide, melting at 209–214° C.,
10. 2-(6-chloro-1,2-benzisoxazol-3-yl)-a-(2-propynyl)-benzenemethanamine hydrochloride starting from 2-(6-chloro-1,2-benzisoxazol-3-yl)-benzaldehyde and employing propargyl bromide, melting at 209–214° C.

The following secondary amines salts were similarly prepared:
11. 2-[2-(1,2-benzisoxazol-3-yl)-phenyl]-1,2,3,6-tetrahydropyridine starting from 1-chloro-3-iodopropane, melting at 242–268° C.,
12. 2-[2-(1,2-benzisoxazol-3-yl)-phenyl]-pyrrolidine starting from cis-1,4-dichloro-2-butene, melting at 253–261° C.

EXAMPLE 37

2-(1,2-Benzisoxazol-3-yl)-a-(3-cyclohexenyl)-benzenemethanamine hydrochloride

A stirred solution 0.5 g of 2-(1,2-benzisoxazol-3-yl)-benzaldehyde in 25 ml of tetrahydrofuran was cooled to 0° C. and 2.4 ml of a 1M solution of lithium bis(trimethylsilyl) amide in hexanes was added dropwise. The mixture was stirred at this temperature for 1 h then 0.36 ml 3-bromocyclohexene was added and the entire solution was then added to a suspension of 0.3 g of zinc powder in 5 ml of tetrahydrofuran. The suspension was stirred at room temperature overnight. The reaction was quenched by the addition of 5 ml of water and the mixture filtered. The mixture was extracted with 60 ml of methylene chloride and the organic extract washed with three 30 ml portions of water then dried over sodium sulfate. The solvent was removed in vacuo and the residue purified by flash chromatography eluting with a 19:1 mixture of methylene chloride-methanol. The pure fractions were acidified with hydrogen chloride gas in methanol and the evaporated residue triturated with heptane to yield 0.41 g of 2-(1,2-benzisoxazol-3-yl)-a-(3-cyclohexenyl)-benzene methanamine hydrochloride, $^1$H-NMR (400 MHz, DMSO-d$_6$) d$_H$ 4.33 (CHNH$_2$).

In a similar way was prepared:
1. 2-(1,2-benzisoxazol-3-yl)-a-(2-propynyl)-benzenemethanamine ethanedioate: starting from 2-(1,2-benzisoxazol-3-yl)-benzaldehyde and employing propargyl bromide, melting at 230–243° C.

EXAMPLE 38

22-(1,2-benzisoxazol-3-yl)-a-propyl-benzenemethanamine hydrochloride

To a solution of 1.16 g of 2-(1,2-benzisoxazol-3-yl)-a-(2-propenyl)-benzenemethanamine in 50 ml of toluene was added 0.06 g of 10% palladium on calcium carbonate and the mixture was hydrogenated at atmospheric pressure for 16 h. The mixture was filtered through dicalite and the filtrate evaporated and submitted to flash chromatography eluting with a 19:1:0.2 mixture of methylene chloride-methanol-ammonia solution to give the pure amine fractions. These fractions were evaporated and acidified with a solution of hydrogen chloride in methanol and evaporated to gum and crystallised from acetone-ether to yield 0.2 g of 2-(1,2-benzisoxazol-3-yl)-a-propyl-benzenemethanamine hydrochloride, melting at 118–126° C.

In a similar manner was prepared:
1. 2-(6-fluoro-1,2-benzisoxazol-3-yl)-a-(2-methyl-propyl)-benzenemethanamine (E)-butenedioate: starting from 2-(6-fluoro-1,2-benzisoxazol-3-yl)-a-(2-methyl-2-propenyl)-benzenemethanamine hydrochloride, melting at 174–184° C.

EXAMPLE 39

2-(1,2-Benzisoxazol-3-yl)-a-methyl-benzenemethanamine hydrochloride

2-[2-(1,2-benzisoxazol-3-yl]-a-methyl-benzyl alcohol

To a stirred solution of 1.07 g of 2-(1,2-benzisoxazol-3-yl)-benzaldehyde in 20 ml of tetrahydrofuran at 0° C. was added 1.8 ml of a 3M solution of methylmagnesium bromide in ether dropwise. The solution was stirred for 50 min then warmed to room temperature and stirred overnight. The reaction was quenched by the addition of 25 ml of saturated ammonium chloride and the mixture was extracted with 100 ml then 50 ml of ether. The combined organic extracts were dried over sodium sulfate and evaporated to yield 1.17 g of 2-[2-(1,2-benzisoxazol-3-yl]-a-methyl-benzyl alcohol as a gum, $^1$H-NMR (200 MHz, CDCl$_3$) d$_H$ 1.54 (CH$_3$).

3-[2-(1-Azidoethyl)-phenyl]-1,2-benzisoxazole

To a stirred solution of 0.6 g of 2-[2-(1,2-benzisoxazol-3-yl]-a-methylbenzyl alcohol and 0.65 g of triphenylphosphine in 10 ml tetrahydrofuran at 0° C. was added 0.39 ml of diethyl azodicarboxylate followed by a solution of 0.54 ml of diphenylphosphoryl azide in 5 ml of tetrahydrofuran. The solution was warmed to room temperature and stirred for 1.5 h. The reaction was evaporated and purified by flash chromatography eluting with 1:1 toluene-heptane to yield 0.27 g of 3-[2-(1-azidoethyl)-phenyl]-1,2-benzisoxazole as a colourless gum, $^1$H-NMR (200 MHz, CDCl$_3$) d$_H$ 5.10 (CHN$_3$).

2-(1,2-Benzisoxazol-3-yl)-a-methyl-benzenemethanamine hydrochloride

To a stirred solution of 0.64 g of 3-[2-(1-azidoethyl)-phenyl]-1,2-benzisoxazole in 10 ml of tetrahydrofuran and 0.1 ml of water was added 0.71 g of triphenyl phosphine. The solution was stirred for 2 days then diluted with 25 ml of water and the solution was extracted with two 50 ml portions of ether and the organic layers were dried over sodium sulfate then evaporated to give a pale yellow gum. This residue was dissolved in a small amount of methanol and 0.37 g of oxalic acid was added and warmed to dissolve. Ether was added and the white solid formed was separed and recrystalised from methanol-ether. To this solid was added 25 ml of a 5% aqueous solution of sodium carbonate and the solution extracted with 50 ml and then 25 ml of methylene chloride. The combined organic layers were washed with 25 ml water, 25 ml of brine then dried over sodium sulfate. Evaporation afforded a colourless oil which was dissolved in methanol and hydrogen chloride in methanol added until the solution was acidic. Evaporation and addition of ether yielded 2-(1,2-benzisoxazol-3-yl)-a-methyl-benzenemethanamine hydrochloride, melting at 229–236° C.

In a similar way was prepared:
1. 2-(1,2-benzisoxazol-3-yl)-a-ethyl-benzenemethanamine hydrochloride, melting at 190–204° C.

EXAMPLE 40

2-(6-Fluoro-1,2-benzisoxazol-3-yl)-a-phenyl-benzenemethanamine hydrochloride 2-(6-fluoro-1,2-benzisoxazol-3-yl)-a-phenyl-phenylmethyl alcohol To a stirred solution of 1.0 g of 2-(6-fluoro-1,2-benzisoxazol-3-yl)-benzaldehyde in 20 ml of tetrahydrofuran at 0° C. was added 4.6 ml of a 1M solution of phenyl-magnesium bromide in tetrahydrofuran dropwise. The solution was stirred for 1.25 h then the reaction was quenched by the addition of 20 ml of saturated ammonium chloride followed by 120 ml of water. The mixture was extracted with three 30 ml portions of ethyl acetate then the combined organic layers were washed with two 30 ml prtions of water. The combined organic extracts were dried over sodium sulfate and evaporated to yield 1.34 g of 2-[2-(1,2-benzisoxazol-3-yl]-a-phenyl-phenylmethyl alcohol as a gum, $^1$H-NMR (200 MHz, CDCl$_3$) d$_H$ 3.90 (CHOH).

[2-(6-Fluoro-1,2-benzisoxazol-3-yl)-phenyl](phenyl)-methanone

A stirred solution of 1.23 g [2-(6-fluoro-1,2-benzisoxazol-3-yl)-phenyl](phenyl)-methanone in 125 ml of toluene in a flash fitted with a Dean-Stark trap was added 6 g of manganese dioxide and the suspension was refluxed for 1.25 h then cooled to room temperature and filtered through dicalite. The residue was washed with 125 ml of toluene and the filtrates evaporated to yield 1.08 g of [2-(6-fluoro-1,2-benzisoxazol-3-yl)-phenyl](phenyl)-methanone, GC-M.S. (E.I.) (M/Z): 317 [M]$^+$.

2-(6-Fluoro-1,2-benzisoxazol-3-yl)-a-phenyl-benzenemethanamine hydrochloride

To a solution of of [2-(6-fluoro-1,2-benzisoxazol-3-yl)-phenyl](phenyl)-methanone in 10 ml of formamide was added 5 ml of formic acid and the solution was refluxed for 5 days. The mixture was cooled to room temperature then poured onto 150 ml of ice-water and the separated solid filtered, washed with water and disolved in 100 ml of methylene chloride. The solution was washed with a 50 ml of a 5% w/v solution of sodium carbonate then two 50 ml portions of water, dried over sodiuym sulphate and evaporated and the residue submitted to flash chromatography eluting with a mixture of 9:1 methylene chloride-ether. This product was suspended in a 1 M solution of hydrochloric acid and stirred at a temperature of 100° C. for 3 h then 12 ml of ethanol was added and the suspension was stirred for a further 2.25 h. The hot solution was filtered and the filrate evaporated, cooled then basified with solid potassium carbonate. The solid product was filtered off, washed with water and dissolved in ether. The solution was washed with 5% w/v solution of sodium carbonate then two portions of water. The organic solution was dried over sodium sulphate and evaporated to give 0.16 g the product as a gum. This material was disolved in 5 ml of methanol and acidified with a solution of hydrogen chloride in methanol. Addition of ether followed by heptane resulted in the formation of 0.15 g of 2-(6-fluoro-1,2-benzisoxazol-3-yl)-a-phenyl-benzenemethanamine hydrochloride, melting at 125–135° C.

EXAMPLE 41

Rat Sleep Analysis

Suppression of REM sleep in male Wistar rats was measured after treatment with compounds according to the invention or reference antidepressants using the methods described by Ruigt et al.(Electroencephalography and clinic Neurophysiology,1989, 73, pages 52–63 & 64–71)

The values reported in Table 1 are expressed as percentage change over placebo for the amount of REM sleep in the first 3 hours after drug administration.

| | | Dose (mg/kg) | | | | | | | | |
|---|---|---|---|---|---|---|---|---|---|---|
| Example | Route | 0.1 | 0.32 | 0.46 | 1 | 2.2 | 3.2 | 4.6 | 10 | 22 | 32 |
| Example 13 | IP | −17 | −26 | | −100 | | | | | | |
| Example 11 | IP | | −44 | | −88 | | | | | | |
| Am | IP | | | | | | | | −22 | −100 | |
| Im | IP | | | | | | | | | −100 | |
| Ve | IP | | | | | 2.2 | −77 | | | | |
| Fl | IP | | | | | | | | 40 | | −100 |
| Mo | IP | | | | | | | | | −61 | −100 |

IP = intra-peritoneal Am = Amitriptyline Im = Imipramine Ve = Venlafaxine Fl = Fluvoxamine Mo = Moclobemide

EXAMPLE 42

The Mouse Marble Burying Assay

This assay was carried out essentially according to the procedure described by Treit et al. (1981) Pharmacol Biochem Behav; 15; 619–626

The results are presented as BUR ED$_{50}$ (sc). This is the effective dose causing 50% inhibition of burying compared to control mice.

| Example No | BUR ED$_{50\ (sc)}$ |
|---|---|
| 11 | 1.04 |
| 11(2) | 0.7 |
| 11(3) | 2.68 |

-continued

| Example No | BUR ED$_{50}$ (sc) |
|---|---|
| 12(2) | 3.4 |
| 13 | 0.39 |
| 13(1) | 1.0 |
| 13(5) | 0.4 |
| 36 | 2.8 |
| 36(1) | 2.5 |
| 36(2) | 1.2 |
| 36(6) | 1.5 |
| 37 | 3.1 |

The present invention relates to the use of an $I_h$ channel modulator in the manufacture of a medicament for use in psychiatry. To certain novel methanamine derivatives, to processes for their preparation, to pharmaceutical formulations containing them and to their use in medical therapy, particularly for use in psychiatry.

The hyperpolarization activated cation current ($I_h$), also indicated as queer or anomolous rectifier current ($I_q$ and $I_{AR}$ respectively), is a membrane current that is carried by $I_h$ channels, with the characteristics that it activates at potentials around or below resting membrane potential. It is carried by both sodium and potassium ions and is unique in that it does not pass lithium ions. The current reverses at approximately −30 mV and the time constant of activation varies with membrane potential, temperature, intracellular cAMP concentration, and other modulators, but typically is about 200 ms at −120 mV at room temperature. $I_h$ is blocked by 1–5 mM caesium (Cs$^+$) (Pape H. C. (1996) Annu. Rev. Physiol. 58:299–327). The $I_h$ channel is not blocked by 1 mM barium (Ba$^{2+}$).

Pape H. C. (Neuroscience 1994 59(2), 363–73) showed that zatebradine (UL-FS49) and its derivative DK-AH268, known as a specific bradycardic agents, are capable of reducing the conductance underlying $I_h$ at concentrations in the range of 1E-5 to 1E-3 M. Apparently the mechanism involved is a use-dependent blockade with no alteration in the gating properties. ZD7288 (4-(N-ethyl-N-phenylamino)-1,2-dimethyl-6-(methylamino)-pyrimidinium-chloride), which also has selective bradycardic properties, was shown to be capable of blocking $I_h$ with an IC$_{50}$ of 2E-6 M (Harris, N. C. and Constanti, A., 1995, J. Neurophysiol., 74(6):2366–2378). ZD7288 is thought to be a selective blocker of $I_h$ since it did not significantly affect other bioelectrical cell properties. Similar data have been published previously (Harris, N.C., Libri, V. and Constanti, A., 1994, Neurosci. Lett., 176:221-225) for ZM227189, a triazinium iodide derivative of ZD7288.

It has now surprisingly been found that $I_h$ channel modulators are effective in the treatment or prevention of psychiatric disorders, including depression, anxiety and psychosis.

Accordingly, the present invention provides the use of an $I_h$ channel modulator in the manufacture of a medicament for the treatment or prevention of a psychiatric disorder, including depression, anxiety and psychosis.

The present invention further includes the use of an $I_h$ channel modulator in the manufacture of a medicament for the treatment or prevention of a psychiatric disorder, with the proviso that the modulator is not a compound of formula (D):

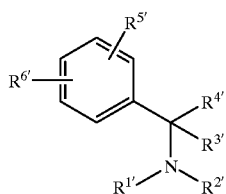

wherein $R^{1'}$ and $R^{2'}$, which may be the same or different, are each selected from $C_{6-12}$aryl, $C_{2-14}$heteroaryl, $C_{6-12}$aryl$C_{1-6}$alkyl, $C_{2-14}$heteroaryl$C_{1-6}$alkyl (where the alkyl, aryl or heteroaryl moiety may be optionally substituted by one or more substituents selected from $C_{1-6}$alkoxy, $C_{1-6}$alkyl, $C_{3-6}$cycloalkyl, $C_{4-6}$cycloalkenyl, $C_{6-12}$aryl, $C_{2-14}$heteroaryl, halogen, amino, hydroxy, halo$C_{1-6}$alkyl, nitro, $C_{1-6}$alkylthio, sulphonamide, $C_{1-6}$alkylsulphonyl, hydroxy$C_{1-6}$alkyl, $C_{1-6}$alkoxycarbonyl, carboxyl, carboxy$C_{1-6}$alkyl, carboxamide and $C_{1-6}$alkylcarboxamide), hydrogen, $C_{1-6}$alkyl, $C_{3-6}$cycloalkyl, $C_{3-6}$cycloalkyl-$C_{1-6}$alkyl, $C_{4-6}$cycloalkenyl, $C_{2-6}$alkenyl, $C_{2-6}$alkynyl and $C_{1-6}$alkoxy$C_{1-6}$alkyl (where the alkyl, cycloalkyl, cycloalkenyl, alkenyl, alkynyl, or alkoxyalkyl moieties may be optionally substituted by one or more substituents selected from amino, halogen, hydroxy, $C_{1-6}$alkylcarboxamide, carboxamide, carboxy, $C_{1-6}$alkoxycarbonyl, $C_{1-6}$alkylcarboxy and carboxy$C_{1-6}$alkyl) or one of $R^{1'}$ and $R^{2'}$ are as hereinbefore defined and one is hydroxy;

$R^3$ and $R^4$, which may be the same or different, are each selected from $C_{6-12}$aryl, $C_{2-14}$heteroaryl, $C_{6-12}$aryl$C_{1-6}$alkyl, $C_{2-14}$heteroaryl$C_{1-6}$alkyl (where the alkyl, aryl or heteroaryl moiety may be optionally substituted by one or more substituents selected from $C_{1-6}$alkoxy, $C_{1-6}$alkyl, $C_{3-6}$cycloalkyl, $C_{4-6}$cycloalkenyl, $C_{6-12}$aryl, $C_{2-14}$heteroaryl, halogen, amino, hydroxy, halo$C_{1-6}$alkyl, nitro, $C_{1-6}$alkylthio, sulphonamide, $C_{1-6}$alkylsulphonyl, hydroxy $C_{1-6}$alkyl, $C_{1-6}$alkoxycarbonyl, carboxyl, carboxy$C_{1-6}$alkyl, $C_{1-6}$alkylcarboxamide and carboxamide), hydrogen, $C_{1-6}$alkyl, $C_{3-6}$cycloalkyl, $C_{3-6}$cycloalkyl$C_{1-6}$alkyl, $C_{4-6}$cycloalkenyl, $C_{2-6}$alkenyl, $C_{2-6}$alkynyl, $C_{1-6}$alkoxy$C_{1-6}$alkyl, halo$C_{1-6}$alkyl, halo$C_{2-6}$alkenyl, halo$C_{2-6}$alkynyl, cyano, carboxyl, $C_{1-6}$alkylcarboxy and carboxy$C_{1-6}$alkyl (where the alkyl, cycloalkyl, cycloalkenyl, alkenyl, alkynyl, or alkoxyalkyl moieties may be optionally substituted by one or more substituents selected from amino, hydroxy, $C_{1-6}$alkylcarboxamide, carboxamide, carboxy, $C_{1-6}$alkoxycarbonyl, $C_{1-6}$alkylcarboxy and carboxy-$C_{1-6}$alkyl); or one of $R^{3'}$ or $R^{4'}$ together with one of $R^{1'}$ or $R^{2'}$ and the N atom to which it is attached form a 5- or 6-membered heterocyclic ring.

$R^5$ represents one or more ring substituents selected from halogen, hydrogen $C_{1-6}$alkyl and $C_{1-6}$alkoxy; and
$R^{6'}$ represents a single ring substituent of formula:

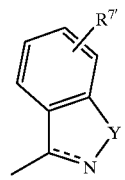

wherein the dotted line represents an optional bond; Y is oxygen or -NR$^{8'}$ (where R$^{8'}$ is hydrogen or $C_{1-6}$alkyl) and R$^{7'}$ represents one or more substituents selected from hydrogen, halogen, haloC$_{1-6}$alkyl, C$_{1-6}$alkyl and C$_{1-6}$alkoxy;

or a pharmaceutically acceptable salt or solvate thereof.

The compounds of formula (D) above are disclosed in PCT application No. PCT/EP 97/01904, the contents of which are incorporated herein by reference.

I$_h$ channel modulators can both change I$_h$ channel conductance and/or I$_h$ channel open probability. These terms are well known to a skilled person or described in the literature, for example, Hille, B. Ionic channels of excitable membranes (second edition). Sinauer Associates Inc. Sunderland, Massachusetts, 1992. and Single-channel recording (second edition). Sakmann, B. and Neher, E. (eds). Plenum Press, New York, 1995. I$_h$ channel modulators include agents which inhibit the conductance of the channel and/or the open probability and in particular those modulators which block the I$_h$ channel as assessed by measuring I$_h$ current and/or the change in membrane potential caused by activation or inhibition or block of I$_h$ current. More specifically, I$_h$ channel modulators include modulators with an IC$_{50}$ in the I$_h$ channel functional assay described herein in the range 1E-5 to 1E-12 mol.l$^{-1}$ (pIC$_{50}$ 5 to 12) or more preferably in the range 1E-6 to 1E-9 mol.l$^{-1}$ (pIC$_{50}$ 6 to 9).

I$_h$ channel modulators according to the present invention, further include those agents which show at least 5 fold selectivity in potency in the I$_h$ channel functional assay over activity on one or more (including 2, 3 or 4) known ion channel(s), such as voltage-dependent Na$^+$, K$^+$ and Ca$^{2+}$ channels as measured in a functional assay (for methods see for example Ogata, N., Yoshii,M., and Narahashi, T., 1989, Brain Res., 476:140–144). More particularly 5 to 10 fold selectivity and preferably 10 fold selectivity or more. I$_h$ channel modulators that show at least 5 fold selectivity in potency in the I$_h$ channel functional assay over activity on one or more (including 2, 3 or 4) known monoaminergic receptor(s), such as the G-protein coupled receptors for noradrenaline, serotonin, dopamine, GABA, glutamate and glycine and ligand-activated ion channels for serotonin, GABA, glutamate and glycine, or the monoaminergic uptake site, such as the membrane transporters for noradrenaline, serotonin, dopamine, GABA, glutamate and glycine, as determined in a functional and/or binding assay known to be specific for that type of receptor or transporter. More particularly 5 to 10 fold selectivity and preferably 10 fold selectivity or more are also included within the scope of the present invention. Included within the scope of the present invention, are I$_h$ channel modulators which have one or more of the aforementioned characteristics.

Depression states in the treatment of which the compounds of formula (I) and their pharmaceutically acceptable salts and solvates are particularly useful, are those classified as *affective disorders* in the Diagnostic and Statistical Manual of Mental Disorders. Fourth Edition-Revised, American Psychiatric Association, Washington, D.C. (1994), including the mood disorders, other specific affective disorders and bipolar and depressive disorders not otherwise specified.

Other uses in human therapy for the compounds of formula (I) or a pharmaceutically acceptable salt or solvate thereof includes the treatment of the following conditions:

anxiety disorders, including phobic neuroses, panic neuroses, anxiety neuroses, post-traumatic stress disorder and acute stress disorder.

attention deficit disorders.

eating disorders, including obesity, anorexia nervosa and bulimia.

personality disorders, including borderline personality disorders.

schizophrenia and other psychotic disorders, including schizo affective disorders, dilusional disorders, shared psychotic disorder, brief psychotic disorder and psychotic disorder.

narcolepsy-cataplexy syndrome.

substance related disorders.

sexual function disorders.

The present invention further provides a method for the treatment or prevention of a psychiatric disorder, including any of the aforementioned disorders or conditions, in an animal, for example, a mammal including a human, which comprises administering to said animal an effective amount of an I$_h$ channel modulator.

A further feature of the present invention includes the use of an I$_h$ channel modulation assay for identifying compounds useful for the treatment or prevention of psychiatric disorders. Such assay can, for example, include taking a brain slice, or a cultured brain slice, or ganglia of the peripheral nervous system, or primary cell cultures of central and/or peripheral nervous tissue, or cell lines expressing I$_h$ channels in order to incubate and/or expose these cells and tissues to test compounds with the aim to assess whether these test compounds affect I$_h$ current and/or the change in membrane potential caused by activation or inhibition or block of I$_h$ current.

The present invention includes within its scope, compounds which are modulators of the I$_h$ channel, including those novel I$_h$ channel modulators which have the IC$_{50}$ and pIC$_{50}$ values mentioned above and/or the selectivity in the I$_h$ channel functional assay over the activity on one or more (including 2, 3 or 4) known ion channel(s) and/or activity on one or more (including 2, 3 or 4) known monoaminergic receptor(s) or uptake site as mentioned above; with the proviso that the compounds are not the compounds of formula (D) above.

The present invention further includes the compounds of formula (I) :

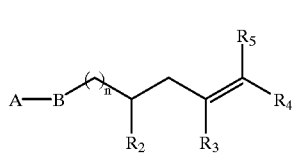

(I)

wherein A is a group selected from (a), (b) or (c):-

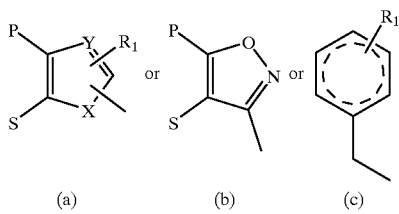

(a)　　　　　(b)　　　　　(c)

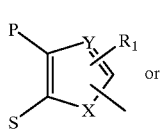

(a)

or

-continued

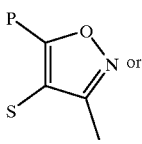

(b)

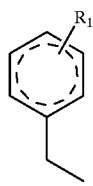

(c)

wherein Y is CH or N;

X is O, S, CH=CH, or CH=N;

P and S, which may be the same or different, each represent hydrogen, $C_{1-4}$alkyl, $C_{1-3}$alkoxy, cyano, halogen, trifluoromethyl, phenyl or pyrrole wherein the phenyl or pyrrole moieties may be optionally substituted with halogen or $C_{1-3}$alkyl; or P and S together with the ethylene group to which they are bonded form a 1,2-phenylene, a pyridinediyl (including 2,3-and 3,4-pyridinediyl), or a 1-cyclohexen-1,2-diyl group, which groups may be optionally substituted by one or more substituents selected from hydrogen, $C_{1-4}$alkyl, $C_{1-3}$alkoxy, cyano, halogen trifluoromethyl, phenyl and pyrrole wherein the phenyl or pyrrole moieties may be optionally substituted with halogen or $C_{1-3}$alkyl;

$R_1$ represents one or more ring substituents selected from hydrogen, $C_{1-4}$alkyl, $C_13$alkoxy, cyano, halogen, trifluoromethyl, phenyl and pyrrole wherein the phenyl or pyrrole moieties may be optionally substituted with halogen or $C_{1-3}$alkyl;

B is a bivalent radical derived from an aromatic group selected from (d), (e) or (f):-

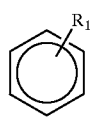

(d)

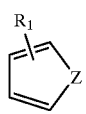

(e)

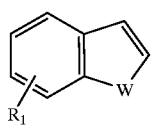

(f)

Z is O or S; W is O, S or CH=CH; $R_1$ is as hereinbefore defined;

$R_2$ is $NH_2$ $R_3$, $R_4$, and $R_5$, which may be the same or different, each represent halogen, $C_{1-4}$alkyl or hydrogen, or $R_4$ and $R_5$ together form a carbon—carbon bond;

n is 0 or 1;

or a physiologically acceptable salt or solvate thereof;

with the proviso that when A is group (b) wherein P and S together with the ethylene group to which they are bonded form a 1,2-phenylene group, which group may be optionally substituted by one or more substituents selected from hydrogen, $C_{1-4}$alkyl, $C_{1-3}$alkoxy, cyano, halogen, trifluoromethyl, phenyl and pyrrole wherein the phenyl or pyrrole moieties may be optionally substituted with halogen or $C_{1-3}$alkyl; $R_2$, $R_3$, $R_4$ and $R_5$ are as herein before defined and n is 0; then B is a group (e) or (f).

As used herein the term alkyl as a group or part of a group means a straight or branched chain alkyl group. Such alkyl groups include methyl, ethyl, i-propyl, n-propyl, n-butyl, s-butyl, t-butyl, n-pentyl, isopently, neopentyl, n-hexyl, isohexyl and neohexyl. References to alkenyl groups include groups which may be in the E- or Z-form or a mixture thereof and which when they contain at least three carbon atoms, may be branched. Examples of particular alkenyl groups include vinyl, allyl, butenyl, isobutenyl, pentenyl, isopentenyl, hexenyl, isohexenyl, neohexenyl and 1-methyl-2-propenyl. The terms alkoxy and alkynyl have meanings as understood by the person skilled in the art and include straight and branched chains. Examples of alkoxy groups include methoxy and ethoxy and examples of alkynyl groups include ethynyl, propynyl and butynyl.

As used herein the terms cycloalkyl and cycloalkenyl have meanings as understood by the person skilled in the art and include cyclopropyl, cyclobutyl, cyclobutenyl, cyclopentyl, cyclopentenyl, cyclopentadienyl, cyclohexyl, cyclohexenyl and cyclohexadienyl.

The term halogen includes chloro, bromo, fluoro and iodo. The term halo$C_{1-6}$alkyl means an alkyl group in which one or more hydrogens is replaced by halo and preferably containing one, two or three halo atoms. Examples of such groups include trifluoromethyl and fluoroisopropyl.

As used herein the term aryl as a group or part of a group means $C_{6-12}$aryl aromatic groups and includes one or two $C_6$ aromatic rings. The term covers fused ring systems as well as systems in which rings are connected through a linking group, for example —N—, —C—, —O— or —S—, or a bond. Examples of such groups include phenyl, naphthyl, and biphenyl.

As used herein the term heteroaryl as a group or part of a group means $C_{2-14}$heteroaryl aromatic groups optionally substituted with one or more substituents independently selected from hydrogen, halogen, $C_{1-6}$alkyl or $C_{1-6}$alkoxy and includes one or two $C_{5-7}$ aromatic rings containing one or more (for example, one to three) heteroatoms selected from oxygen, sulphur, and nitrogen. The term includes the substituent $R^6$ as hereinbefore defined, fused ring systems as well as systems in which rings are connected through a linking group, for example —N—, —C—, —O— or —S—, or a bond. Examples of such groups include 1,2-benzoisoxazolyl, pyridyl, thiadiazolyl, indazolyl, benzofuryl, quinolyl, thienyl and isoquinolyl.

The term 5- and 6-membered heterocyclic ring means a saturated or partially saturated 5- and 6-membered ring. Examples of such saturated groups include piperidinyl and pyrrolidinyl and partially saturated groups include tetrahydropyridinyl.

The term halo$C_{1-6}$alkyl means an alkyl group in which one or more hydrogens is replaced by halo and preferably containing one, two or three halo atoms. Examples of such groups include trifluorobutyl and trifluoromethyl.

The term halo$C_{2-6}$alkenyl means an alkenyl group in which one or more hydrogens is replaced by halo and preferably containing one, two or three halo groups. The halo atoms may be present on saturated or unsaturated carbon atoms. Examples of such groups include 2-chloropropenyl, 3,3-difluoropropenyl and 1,1-difluoropropenyl.

The term haloC$_{2-6}$alkynyl mean s an alkynyl group in which one or more hydrogens is replaced by halo and preferably containing one, two or three halo groups. The term includes alkynyl groups with a terminal halo atom. Examples of such groups include 3-chloropropynyl and 3-bromopropynyl.

It will be appreciated that some of the compounds of formula (I) and their salts and solvates may contain one or more centres of chirality and exist as stereoisomers including diastereomers and enantiomers. The present invention includes the aforementioned stereoisomers within its scope and each of the individual (R) and (S) enantiomers of the compounds of formula (I) and their salts and solvates substantially free ie associated with less than 5%, preferably less than 2%, in particular less than 1% of the other enantiomer and mixtures of such enantiomers in any proportions including racemic mixtures containing substantially equal amounts of the two enantiomers.

Ring substituent R$_1$ in formula (I) may be in any one or more of the available ring positions. Specific examples of single ring substituents include 4-chloro, 2 and 4 fluoro or 4-methyl-. Examples of multiple substituents include 2-fluoro-4-methyl, 4-chloro-3-fluoro and 3,4-dichloro.

In formula (I), the A group may be attached to the B group via any available carbon atom and vice versa The B groups may be attached via any available B group ring carbon atom to the carbon atom of the side chain:-

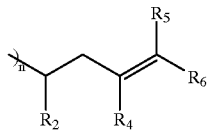

For example, when group A has the structure (a) then the B group may be attached to an y of the heterocyclic ring carbons. When group A has the structure (b) then the B group is attached to the A group at position 3 and when the A group has structure (c) then the B group is attached by the methylene carbon. When the B group has structure (d) then the A group may be attached at any position but preferrably ortho-related to the side chain. When the B group has structure (e) or (f) then the A group may be attached at positions 2- or 3.

The compounds of formula (I) further include the compounds of formula (IA), (IB) and (IC) below:-

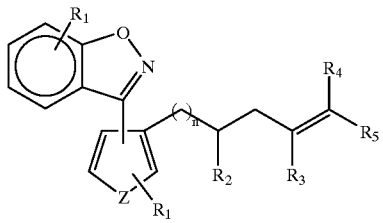

wherein Z, R$_2$, R$_2$, R$_3$, R$_4$ and R$_5$ are as herein before defined and n is 0; or a physiologically acceptable salt or solvate thereof;

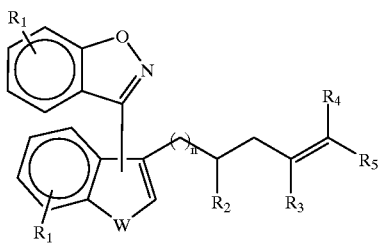

wherein W, R$_1$, R$_2$, R$_3$, R$_4$ and R$_5$ are as herein before defined and n is 0; or a physiologically acceptable salt or solvate thereof, and

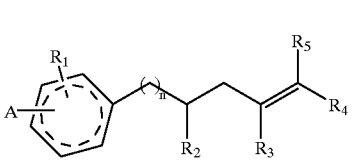

wherein A, R$_1$, R$_2$, R$_3$, R$_4$ and R$_5$ are as herein before defined and n is 0 or 1, preferably n is 0; or a physiologically acceptable salt or solvate thereof;
with the proviso that A is not a group (b) wherein P and S together with the ethylene group to which they are bonded form a 1,2-phenylene group, which group may be optionally substituted by one or more substituents selected from hydrogen, C$_{1-4}$alkyl, C$_{1-3}$alkoxy, cyano, halogen, trifluoromethyl, phenyl and pyrrole wherein the phenyl or pyrrole moieties may be optionally substituted with halogen or C$_{1-3}$alkyl; R$_2$, R$_3$, R$_4$ and R$_5$ are as herein before defined and n is 0; or a physiologically acceptable salt or solvate thereof.

The compounds of formula (I), (IA), (IB), (IC) and the compounds herein which fall within the scope of formula (I), may hereinafter be referred to as compounds according to the present invention.

Examples of groups of formula A include benzoxazolyl, benzothiazolyl, naphthalenyl, isothiazolyl, thiophenyl, furanyl, isoxazolyl, quinolinyl, isoxazolopyridinyl, 4,5,6,7-tetrahydro-benzisoxozolyl, isoquinolinyl, benzofuranyl, benzothiophenyl, benzisothiazolyl, pyridinyl, phenyl and benzyl. Each of the aforementioned groups may optionally be substituted by a group selected from hydrogen, halogen, C$_{1-4}$alkyl, C$_{1-3}$alkoxy, cyano, trifluoromethyl, phenyl and pyrrole wherein the phenyl or pyrrole moieties may be optionally substituted with halogen or C$_{1-3}$alkyl. Such subtituted groups include 2-methoxybenzyl, 3-methoxybenzyl, 4-fluorophenyl, 3-cyanophenyl, 3-trifluoromethylphenyl, 3,5-dimethyl isoxazol4-yl, 5-chlorobenzofuran-2-yl and 5-fluorobenzothiophen-2-yl.

Examples of formula B include benzene, furan, benzofuran and thiophene.

Preferred A groups according to the invention include isoxazolopyridinyl, naphthyl, benzofuranyl, benzothiophenyl phenyl, substituted phenyl, tetrahydrobenzisoxazolyl, isoquinolinyl, thiazolyl, furanyl, benzyl.

Preferred B groups include phenyl and thienyl.

Most preferred R$_1$ groups include hydrogen, fluorine, chlorine, methyl, trifluoromethyl, and methoxy.

Groups R$_3$, R$_4$ and R$_5$ are preferably hydrogen.

For therapeutic use, salts of the compounds of formula (1), (IA), (IB) and (IC) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

Pharmaceutically acceptable acid addition salts include those derived from mineral acids such as hydrochloric, hydrobromic, hydroiodic, phosphoric, metaphosphoric, nitric and sulphuric acids, and organic acids, such as tartaric, acetic, trifluoroacetic, citric, malic, lactic, maleic, malonic, fumaric, benzoic, ascorbic, propionic, glycolic, gluconic, succinic and methanesulphonic and arylsulphonic, for example p-toluenesulphonic acids.

Preferred salts according to the invention include hydrochloric, fumaric [(E) butenedioic] and maleic [(Z) butenedioic] acid addition salts. Solvates according to the invention include hydrates.

In a further aspect of the invention there are provided the compounds of formula (I), (IA), (IB) and (IC) and their pharmaceutically acceptable salts and solvates for use in therapy, more particularly in the treatment or prevention of psychiatric disorders.

The present invention further includes a method for the treatment of an animal, for example, a mammal including a human, suffering from or liable to suffer from a psychiatric disorder or any of the aforementioned disorders or conditions, which comprises administering an effective amount of a compound of formula (I), (IA), (IB) or (IC) or a pharmaceutically acceptable salt or solvate thereof.

In yet a further aspect, the present invention provides the use of a compound of formula (I), (IA), (IB) or (IC) or a pharmaceutically acceptable salt or solvate thereof in the manufacture of a medicament for the treatment or prevention of a psychiatric disorder or any of the aforementioned disorders or conditions.

The amount of an $I_h$ channel modulator or a compound of formula (I), (IA), (IB) or (IC) or a pharmaceutically acceptable salt or solvate thereof, also referred to herein as the active ingredient, which is required to achieve a therapeutic effect will, of course, vary with the particular compound, the route of administration, the age and condition of the recipient, and the particular disorder or disease being treated.

A suitable daily dose for any of the above mentioned disorders will be in the range of 0.01 to 100 mg per kilogram body weight of the recipient (e.g. a human) per day, preferably in the range of 0.1 to 50 mg per kilogram body weight per day and most preferably in the range 0.1 to 10 mg per kilogram body weight per day. The desired dose may be presented as one, two, three, four, five or more sub-doses administered at appropriate intervals throughout the day.

While it is possible for the active ingredient to be administered alone, it is preferable to present it as a pharmaceutical formulation. Accordingly, the present invention further provides a pharmaceutical formulation comprising an $I_h$ channel modulator or a compound of formula (I), (IA), (IB) or (IC) or a pharmaceutically acceptable salt or solvate thereof, together with a pharmaceutically acceptable carrier thereof and optionally other therapeutic agents. The carrier must be "acceptable" in the sense of being compatible with the other ingredients of the formulation and not deleterious to the recipients thereof.

Formulations include those suitable for oral, rectal, nasal, topical (including transdermal, buccal and sublingual), vaginal or parenteral (including subcutaneous, intramuscular, intravenous, intradermal and intravitreal) administration.

The formulations may be prepared by any methods well known in the art of pharmacy, for example, using methods such as those described in Gennaro et al., Remington's Pharmaceutical Sciences (18th ed., Mack Publishing company, 1990, see especially Part 8: Pharmaceutical Preparations and their Manufacture). Such methods include the step of bringing into association the active ingredient with the carrier which constitutes one or more accessory ingredients. Such accessory ingredients include those conventional in the art, such as, fillers, binders, diluents, disintegrants, lubricants, colorants, flavoring agents and wetting agents.

Formulations suitable for oral administration may be presented as discrete units such as pills, tablets or capsules each containing a predetermined amount of active ingredient; as a powder or granules; as a solution or suspension. The active ingredient may also be presented as a bolus or paste, or may be contained within liposomes.

Formulations for rectal administration may be presented as a suppository or enema.

For parenteral administration, suitable formulations include aqueous and non-aqueous sterile injection. The formulations may be presented in unit-dose or multi-dose containers, for example, sealed vials and ampoules, and may be stored in a freeze dried (lyophilised) condition requiring only the addition of the sterile liquid carrier, for example, water prior to use.

Formulations suitable for administration by nasal inhalation include fine dusts or mists which may be generated by means of metered dose pressurised aerosols, nebulisers or insufflators.

The present invention further includes the following processes for the preparation of compounds of formula (I), (IA), (IB) and (IC).

According to a further aspect of the invention, there is provided a process for preparing a compound of formula (I) or a physiologically acceptable salt or solvate thereof, which comprises:

(A) reacting a compound of formula (II)

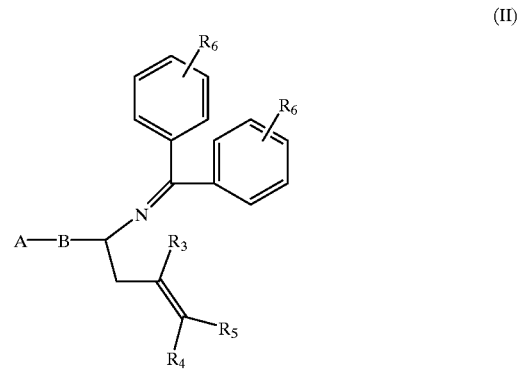

(II)

wherein $R^6$ is hydrogen or halogen, with a hydrolysing agent;

(B) reacting an imine of formula (IIA)

(IIA)

with an appropriate organometallic reagent in the presence of an inert solvent; or (C) for compounds of formula (I) wherein n is 1, the reduction of a compound of formula (XV)

(XVa)

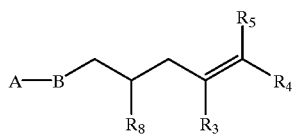

wherein $R_8$ is an azido group, and A, B, $R_3$ $R_4$ and $R_5$ are as previously defined; and where necessary or desired, following processes A to C above, any one or more of the following further steps in any order may be performed:

(i) removing any remaining protecting group(s);
  (ii) converting a compound of formula (I) or a protected form thereof into a further compound of formula (I) or a protected form thereof;
  (iii) converting a compound of formula (I) or a protected form thereof into a pharmaceutically acceptable salt or solvate of a compound of formula (I) or a protected form thereof;
  (iv) converting a pharmaceutically acceptable salt or solvate of a compound of formula (I) or a protected form thereof into a compound of formula (I) or a protected form thereof;
  (v) converting a pharmaceutically acceptable salt or solvate of a compound of formula (I) or a protected form thereof into another pharmaceutically acceptable salt or solvate of formula (I);
  (vi) where the compound of formula (I) is obtained as a mixture of (R) and (S) enantiomers resolving the mixture to obtain the desired enantiomer.
  (vii) cleavage of a compound of fomula (I) from a solid phase resin.

In the following description the symbols A, B, $R_1$, $R_2$, $R_3$, $R_4$, $R_5$ and n have the meanings ascribed to them in formula (I) unless otherwise stated.

Process A, may be effected by hydrolysis of compounds of formula (II) wherein $R^6$ is hydrogen or a halogen, preferably p-F. The reaction can conveniently be carried out in the presence of acid for example 1 M HCl in acetone.

Compounds of formula (II) may be prepared from compounds of formula (III), for example, by deprotonation, typically by addition of base, preferably lithium tert. butoxide in an inert solvent, such as tetrahydrofuran, at a temperature of –100° to 25° C followed by the addition of a reagent $R^4R^5C=C(R^3)CH_2L^1$, in which $L^1$ is a suitable leaving group, such as mesylate or triflate or, a halo atom including iodo, chloro or bromo. This general process is described by C. Giafranco et. al. (J. Org. Chem. 1996, 61, 5134)

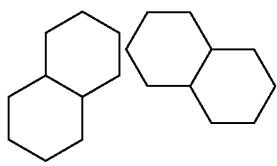

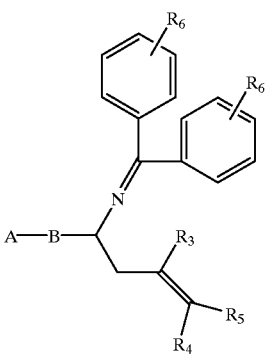

(II)

(III)

Compounds of formula (III), wherein $R^6$ is as hereinbefore described, may be prepared by reacting aldehydes of formula (IV) with an appropriate diarylmethanamine, such as diphenyl or bis-p-fluorophenylmethanamine. The reaction may be carried out azeotropically by distillation or with a drying agent such as titanium tetrachloride, magnesium sulfate or with molecular sieves in an apolar solvent, for example, methylene chloride.

In an alternative process B compounds of formula (I) may be prepared by reaction of an intermediate imine of formula (IIA), such as that prepared from aldehydes of formula (IV) and lithium bis(trimethylsilyl)amide, with an appropriate organometallic reagent, such as a Grignard, or a lithium or zinc reagent derived from $R^4R^5C=C(R^3)CH_2L^2$ in which $L^2$ is a suitable leaving group, such as a chloro or bromo atom, in the presence of an inert solvent such as hexane, toluene or tetrahydrofuran, at a temperature of –100° C. to 100° C., typically at room temperature. This general process is described by D. J. Hart et. al. (J. Org. Chem. 1983, 48, 289).

(IV)

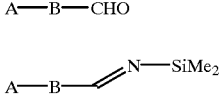

(IIA)

Aldehydes of formula (IV) can be prepared by means of intermolecular palladium coupling reactions using the appropriate trialkyl arylstannyl reagent such as A—$SnBu_3$ with the appropriate bromo or iodo-aryl aldehyde, B(Y)CHO, where Y is a bromo or iodo atom. The reaction may conveniently be carried out in anhydrous xylene solution at 80–115° C. using a palladium catalyst such as tetrakis(triphenylphosphine)palladium (0), or by reaction of an aryl boronic acid reagent, such as A—$B(OH)_2$, with the bromo or iodo-arylaldehydes, in a basic medium, such as 2 N aqueous sodium carbonate solution in a toluene-ethanol mixture at 50–100° C. and using the above mentioned catalyst. Alternatively, this coupling may be carried out by reacting the appropriate aryl or heteroaryl derivative A—L², where L² is a suitable leaving group such as a chloro, bromo or iodo atom, with commercially available 2-formylbenzene boronic acid using the hitherto described reaction conditions. Reagents of formula $R^4R^5C=C(R^3)CH_2L^1$ and $R^4R^5C=C(R^3)CH_2L^2$ may be obtained commercially.

Aldehydes of formula (IV) where A represents a benzisoxazol-3-yl group may be prepared from compounds of formula (VI) where $R^7$ is hydrogen or halogen and $L_2$ is a leaving group such as nitro or halogen, preferably fluoro atom via the intermediate compound of formula (V) using the process described by Schutske G. M. (J. Org. Chem., 1984, 49, 180–183) for the synthesis of 3-phenyl-1,2-benzisoxazole. Hydrolysis to the aldehyde can be carried out using various catalysts, for example dilute acids such as hydrochloric acid at temperatures between 20–100° C.

Compounds of formula (VI), in which $R^7$ represents hydrogen or a halogen atom, in particular fluoro or chloro, may be prepared by the addition of organo-metallic reagents derived from compounds of formula (VII), where $L_2$ is a suitable leaving group, such as a halo atom including iodo, fluoro, bromo or chloro, using methods well known to a person skilled in the art, to a compound of formula (VIII).

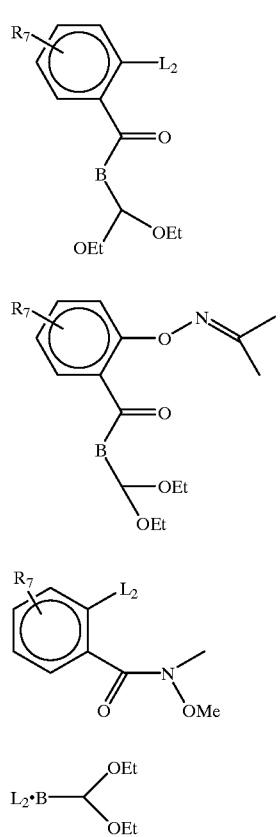

Compounds of formula (VIII), where $R^7$ is as previously assigned, can be obtained commercially or prepared from commercial compounds using the general process described by S. Nahm and S. Weinreb, Tetrahedron Lett., 1981, 22, 3815, using methods well known to a skilled person In an alternative process compounds of formula (VI) can be prepared by the addition of the above mentioned reagents (VII) to an aldehyde of formula (IX) where $L_2$ and $R^7$ are as previously defined, followed by oxidation by the methods described below for the alcohol (X).

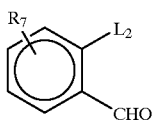

Aldehydes of formula (IV) wherein A is pyridinoisoxazole can be prepared by oxidation of compounds of formula (X), in which two substituents on the pyridine ring have adjacent positions, to give compounds of formula (XII). The oxidation may typically be carried out using a suspension of chromium trioxide and dicalite in dichloromethane at room temperature or by using other methods well known in the art for the oxidation of alcohols to ketones such as chromium trioxide in pyridine or manganese dioxide in toluene at temperatures of 50–100° C. Subsequent treatment of these ketones in the manner described above for ketones of formula (VI) gives the corresponding aldehydes of formula (IV) in which A is a pyridoisoxazole group.

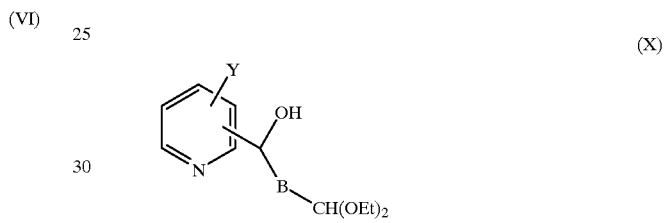

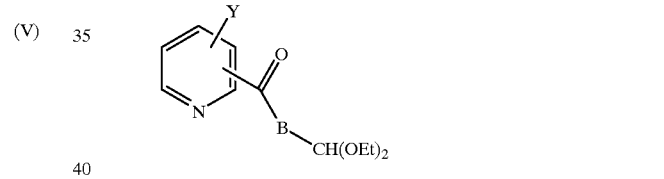

Compounds of formula (X) may be prepared by reaction of the appropriate lithio fluoro or chloropyridine derivatives, derived from the corresponding fluoro or chloro pyridine by treatment with a lithium amide base such as lithium diisopropylamide, with the aldehyde (XII). This latter aldehyde may be prepared from o-bromobenzaldehyde diethyl acetal by treatment with n-butyl lithium followed by reaction with dimethyl formamide using procedures well known in the art.

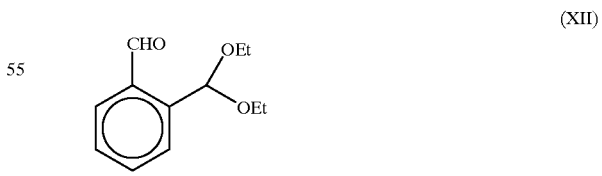

Aldehydes of formula (IV) where A represents 4,5,6,7-tetrahydro-1,2-benzisoxazole may be prepared from a compound of formula (XIII) wherein $L^2$ is a halo atom for example bromo or chloro by treatment with an alkyl lithium reagent such as butyl lithium followed by dimethylformamide.

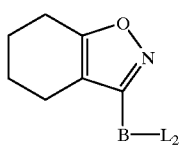
(XIII)

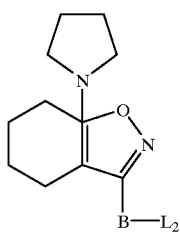
(XIV)

Compounds of formula (XIII) may be prepared from compounds of formula (XIV) by the removal of elements of pyrrolidine in the presence of acid. Compounds of formula (XIV) may be prepared by a 1,3-dipolar addition reaction as described in the literature M. E. Kuehne et. al. J. Org Chem. 1964, 29, 1582.

Aldehydes of formula (IV) where A isoxazole or substituted isoxazole may be prepared from a compound of formula (XV) wherein $L^2$ is a halo atom for example bromo or chloro and P and S are as hitherto discribed by treatment with an alkyl lithium reagent such as butyl lithium followed by dimethylformamide.

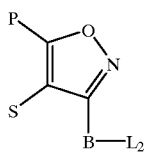
(XV)

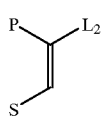
(XVI)

Compounds of formula (XV) where P and S are as hitherto described may be prepared from compounds of formula (XVI) where P and S are as hitherto discribed by a 1,3-dipolar addition reaction followed by an in situ dehydrohalogenation in a similar manner to that described in the literature M. E. Kuehne et. al. J. Org. Chem., 1964, 29, 1582.

According to a third general process C, compounds of formula (I) wherein $R^2$ is an amino group and n=1 can be prepared by reacting a compound of formula (XVa) wherein $R^8$ is an azido group with a suitable reducing agent, for example lithium aluminium hydride, sodium borohydride, or hydrazine in the presence of palladium or tin complexes. Alternatively, the reaction may be carried out with hydrogen and a suitable hydrogenation catalyst or with triphenylphosphine in a suitable mixture of solvents such as water and diethyl ether or tetrahydrofuran, for example at 20° C. to 60° C.

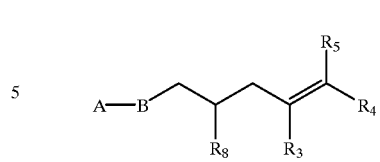
(XVa)

Compounds of formula (XVa) wherein $R^8$ is an azido group can be prepared from compounds of formula (XVa) wherein $R^8$ is a hydroxyl with a mixture of triphenylphosphine, diethyl azodicarboxylate and diphenylphosphoryl azide in an apolar solvent such as toluene or benzene at elevated temperature, for example 20° C. to 60° C., or by reacting a compound of formula (XVa) wherein $R^9$ is a leaving group as hereinbefore described by substitution with inorganic azide salts in a polar solvent at an elevated temperature.

Compounds of formula (XVa) where $R^8$ is a hydroxyl group may be prepared by reaction of compounds of formula (XVII) with an appropriate organometallic reagent, such as a such as a Grignard, or a lithium or zinc reagent derived from $R^5R^6C=C(R^4)CH_2L^2$ in which $L^2$ is a suitable leaving group, such as a chloro or bromo atom, in the presence of an inert solvent such as hexane, toluene or tetrahydrofuran, at a temperature of –100° C. to 100° C., typically at room temperature.

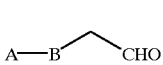
(XVII)

Compounds of formula (XVII) may be prepared by methods hereinbefore described utilizing aldehydes such as (XVIII) in which $L_3$ is a halogen such as chloro or bromo and $R_{10}$ is a $C_{1-6}$ alkyl or $C_{3-5}$ cycloalkyl group, prepared by methods described in the literature (B Wünsch, Arch. Pharm. (Weinheim) 1990, 323, 493).

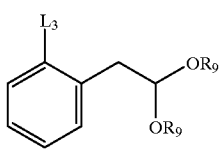
(XVIII)

The present invention further includes all novel intermediates hereinbefore described.

The following examples are intended for illustration only and are not intended to limit the scope of the invention in any way.

EXAMPLE 1

The next section describes the methods used for

A) determining the potency of compounds to inhibit the hyperpolarisation-activated inward cation current $I_h$ in dorsal root ganglion (DRG) cells of the rat; the effect is measured as the decrease in $I_h$ activation rate and is expressed as the half maximal effect concentration ($IC_{50}$) or the negative logarithm of this $IC_{50}$ (known as $pIC_{50}$).

B) determining the potency of compounds to inhibit marble burying behaviour in mice (BUR)

Methods
A) hyperpolarisation-activated cation current ($I_h$)
Culture of dissociated DRG neurons To obtain E15 DRGs, pregnant Wistar rats were sacrificed. Embryos were removed and spinal cords with DRG attached to both sides were dissected out and collected in Hanks balanced salt solution (HBSS; Gibco). DRG were separated from the spinal cord and pooled in HBSS without $Ca^{2+}$ and $Mg^{2+}$. Dissociation of intact DRG was started by incubation with a 0.25% trypsin solution for 30 min at 37° C. Trypsination was stopped by diluting the enzyme and centrifugation (1 min; 2500 rpm). After aspiration of the supernatant the tissue pellet was triturated with DMEMF10 (DMEM supplemented with 10% fetal bovine serum (Hyclone), 6 g/l glucose and 2 mM I-glutamine) and centrifuged for 10 min at 1700 rpm. Dissociated DRG cells were resuspended in culture medium (DMEMF10 with 50 ng/ml NGF 2.5S (Alomone labs)), counted and plated out in a density of $1–2 \cdot 10^5$ cells on collagen (50 μg/ml) and/or poly-l-lysine (10-20 pg/ml) coated glass coverslips in 24-well tissue culture plates. Plates were kept in a humidified incubator at 37° C and 5% $CO_2$ for 72 hrs. Glial cell proliferation was inhibited when necessary by adding cytosine arabinoside (Ara-c) at a concentration of $5.10^{-7}$ M. After 3 days fresh culture medium was administered. Medium was subsequently changed every 3–4 days.

Electrophysiological measurements

DRG cells were sampled with the whole cell voltage clamp method. Glass electrodes were pulled from thick-walled borosilicate capillaries with filament (1 mm outer diameter). Pipette resistance was 2–5 MΩ. Series resistance (5–15MΩ) was compensated for to ensure so that potential errors made in the determination of the actual membrane potential were less then 2 mV. Cell capacitance (10–75 pF) compensation was used to compensate for capacitive currents. The extracellular solution contained (in mM): NaCl 140; KCl 5; $CaCl_2$ 2; $MgCl_2$ 1; D(+) glucose 5.6; HEPES 5; Sucrose 30; pH=7.4. The pipette solution contained (in mM): K-gluconate 119; NaCl 5; KCl 13; CsCl 2; $CaCl_2$ 1; EGTA 10; HEPES 10; pH=7.2. Cells were preincubated for more then 1 ½ hours with different concentrations (1E-9 to 1E-4 M) of test compound dissolved in extracellular solution at room temperature (20° C.) in normal air. Larger cells that appeared round with a pronounced halo under phase-contrast microscopy were selected because almost all of them expressed $I_h$. Data were acquired with a Digidata 1200® analogue to digital interface using PCLAMP® software (both from Axon Instruments). For $I_h$ activation the cell was held at −63 mV and stepped to −123 mV (potentials after correction for liquid junction potential). Current traces were selected for soundness, averaged and fitted to a first order exponential using PCLAMP® software (fit between 60 and 950 ms to avoid biasing by transient currents). Activation time constants (τ) for $I_h$ under different drug concentrations were derived from this fit. The activation rate constant for $I_h$ is defined as $k_{act}=1/\tau$.

Determination of (p)$IC_{50}$ for inhibition of $I_h$

The $pIC_{50}$ is the (−) log concentration of a compound at which the $I_h$ activation rate constant $k_{act}$ is reduced by 50%. $pIC_{50}$ for a compound could be estimated adequately by fitting $k_{act}$ to the logarithm of the concentration with a logistic function using PRISM® software (Graphpad Inc.). The function chosen is:

$k_{act}=A/(1+10^{\wedge}(\log([compound])+pIC_{50}))$; A is $k_{act}$ at [compound]=0 M.

Averaging all control measurements yields that $A=3.52\ s^{-1}$ and the maximum $k_{act}$ was forced to this value for all compounds in this study. The Hill slope that normally is estimated in concentration-effect relations appeared to be about 1 and was subsequently fixed to this value. The advantage of fixing Hill slope, minimum ($k_{act}=0\ S^{-1}$) and maximum ($k_{act}=3.52\ s^{-1}$) values is that only one parameter has to be estimated from a limited number of datapoints, which improves precision of the estimate.

B) marble burying behaviour in mice (BUR)

This assay was carried out essentially according to the procedure described by Treit et al. (1981) Pharmacol Biochem Behav; 15; 619–626

The results are presented as BUR $\log(ED_{50})$ (s.c.). This is the logarithm of the effective dose (in μmol•$kg^{-1}$) causing 50% inhibition of burying compared to placebo-injected mice.

Results

TABLE I

Summary of data for compound-induced inhibition of $I_h$ activation rate constant (potency expressed as $pIC_{50}$ (mean ± SE)) and mice burying behaviour (potency expressed as $\log(ED_{50})$; $ED_{50}$ in μmol/kg).

| | $pIC_{50}$-$I_h$ | SE | log ($ED_{50}$-BUR) |
|---|---|---|---|
| 2-(1,2-Benzisoxazol-3-yl)-a-methyl-benzenemethanamine hydrochloride | 5.24 | 0.20 | 1.27 |
| 2-(6-chloro-1,2-benzisoxazol-3-yl)-a-2-propenyl-benzenemethanamine hydrochloride | 6.44 | 0.18 | 0.32 |
| (S)-(−)-2-(1,2-benzisoxazol-3-yl)-5-fluoro-a-2-propenyl-benzenemethanamine(E)-utenedioate | 5.98 | 0.24 | 0.70 |
| (S)-(−)-2-(6-fluoro-1,2-benzisoxazol-3-yl)-a-2-propenyl-benzenemethanamine(E)-butenedioate | 6.13 | 0.14 | 0.40 |
| (S)-(−)-2-(6-chloro-1,2-benzisoxazol-3-yl)-a-2-propenyl-benzenemethanamine hydrochloride | 6.79 | 0.19 | 0.08 |
| 2-(1,2-benzisoxazol-3-yl)-N-benzyl-benzenemethanamine ethanedioate | 5.06 | 0.12 | 1.65 |
| (R)-2-(1,2-Benzisoxazol-3-yl)-α-2-propenyl-benzenemethanamine hydrochloride | 5.12 | 0.11 | 1.73 |
| (S)-2-(1,2-Benzisoxazol-3-yl)-α-2-propenyl-benzenemethanamine hydrochloride | 6.48 | 0.17 | 0.11 |
| 2-(1,2-Benzisoxazol-3-yl)-α-methyl-benzenemethanol | 5.50 | 0.16 | 1.46 |
| 2-(1,2-Benzisoxazol-3-yl)-α-butyl-benzenemethanamine hydrochloride | 5.98 | 0.19 | 0.95 |

TABLE 2

Mice burying behaviour (potency expressed in mg/kg)

| Example | BUR sc ED50(mg/kg) |
|---|---|
| 15(4) | 8.6 |
| 15(6) | 11.6 |
| 15(25) | 3.2 |
| 16(2) | 9.9 |
| 16(4) | 9 |
| 15(14) | 19 |
| 15(34) | 6.9 |
| 15(37) | 9 |
| 16(7) | 7.6 |
| 16(6) | 3.8 |

TABLE 3

Mice burying behaviour (potency expressed in mg/kg)

| Compound | BUR s.c. ED$_{50}$ (mg/kg) | I$_h$ amplitude |
| --- | --- | --- |
| Example 16(5) | 1.7 | 90% inhibition at 1E-5 M |

EXAMPLE 2

2-(2-fluoro-4-methylphenyl)benzaldehyde

A mixture of 2 g of 4-bromo-3-fluorotoluene, 1.75 g of 2-formylbenzeneboronic acid, 0.36 g of tetrakis (triphenylphosphine)-palladium (0) and 11.6 ml of 2N aqueous sodium carbonate, in 50 ml of a 9:1 mixture of toluene-ethanol was heated to 100° C. for 3 h. The mixture was cooled to room temperature, diluted with 100 ml of methylene chloride and washed with 50 ml of 5% sodium bicarbonate containing 5 ml of 0.880 ammonia. The organic layer was dried over sodium sulfate and evaporated to dryness under reduced pressure. The resulting oil was purified by chromatography on silica gel eluting with ethyl acetate-heptane (1:3) to give 1.62 g of 2-(2-fluoro-4-methylphenyl)benzaldehyde as an oil, GC-M.S. (E.I.) (M/Z): 214 [M$^+$].

In a similar manner were prepared:

2-(benzo[b]thiophen-3-yl)benzaldehyde, starting from 3-bromobenzothiophene (prepared by the method of J. Szmuszkovicz and E. J. Modest, *J. Am. Chem. Soc.* 1950, 72, 571), GC-M.S. (E.I.) (M/Z): 238 [M$^+$], 2-(napth-2-yl)benzaldehyde starting from 2-bromonapthalene, $^1$H-NMR (200 MHz, CDCl$_3$) d 10.03 (CHO), 2-(benzo[b]furan-3-yl)benzaldehyde, starting from 3-bromobenzofuran (prepared by the method of D. S. Noyce and R. W. Nichols, *J. Org. Chem.* 1972, 37, 4311), GC-M.S. (E.I.) (M/Z): 222 [M$^+$], 2-phenylbenzaldehyde starting from iodobenzene, GC-M.S. (E.I.) (M/Z): 182 [M$^+$], 2-(2-methoxyphenyl)benzaldehyde starting from 2-bromoanisole, GC-M.S. (E.I.) (M/Z): 212 [M$^+$], 2-(napth-1-yl)benzaldehyde starting from 1-bromonapthalene, GC-M.S. (E.I.) (M/Z): 232 [M$^+$], 2-(quinolin-3-yl)benzaldehyde starting from 3-bromoquinoline, melting at 83–85° C., 2-(thien-3-yl)benzaldehyde starting from 3-bromothiophene, IR: 1694 cm$^{-1}$, 2-(thien-2-yl)benzaldehyde starting from 2-bromothiophene, IR: 1691 cm$^{-1}$, 2-(isoquinolin-4-yl)benzaldehyde starting from 4-bromoisoquinoline, GC-M.S. (E.I.) (M/Z): 233 [M$^+$], 2-(pyridin-3-yl)benzaldehyde starting from 3-bromopyridine, $^1$H-NMR (200 MHz, CDCl$_3$) d 10.00 (CHO), 2-(4-pyrolinylphenyl)benzaldehyde starting from 1-(4-iodophenyl)pyrole, $^1$H-NMR (200 MHz, CDCl$_3$) d 10.04 (CHO), 2-(thiazol-2-yl)benzaldehyde starting from 2-bromothiazole, melting at 76–77° C., 2-(4-phenyl-3-fluorophenyl)benzaldehyde starting from 4-bromo-3-fluorobiphenyl, melting at 107–108° C., 2-(furan-3-yl)benzaldehyde starting from 3-bromofuran, GC-M.S. (E.I.) (M/Z): 196 [M$^+$], 2-(3,5-dimethylisozazol-4-yl)benzaldehyde starting from 3,5-dimethyl-4-iodoisoxazole, melting at 128–129° C., 2-benzylbenzaldehyde starting from benzyl bromide, $^1$H-NMR (200 MHz, CDCl$_3$) d 10.25 (CHO), 2-(2-chlorophenyl)benzaldehyde starting from 2-bromochlorobenzene, GC-M.S. (E.I.) (M/Z): 215 [M$^+$—H], 2-(5-chlorothien-2-yl)benzaldehyde starting from 2-bromo-5-chlorothiophene, melting at 101–103° C., 2-(3-fluoro-4-methylphenyl)benzaldehyde starting from 4-bromo-2-fluorotoluene, GC-M.S. (E.I.) (M/Z): 214 [M$^+$], 2-(3-fluoro-4-chlorophenyl)benzaldehyde starting from 4-bromo-2-chloro-1-fluorobenzene, GC-M.S. (E.I.) (M/Z): 234 [M$^+$], 2-(3-methoxybenzyl)benzaldehyde starting from 1-bromomethyl-3-methoxybenzene, $^1$H-NMR (200 MHz, CDCl$_3$) d 10.25 (CHO), 2-(2-methoxybenzyl)benzaldehyde starting from 1-bromomethyl-2-methoxybenzene (prepared by the method of H. B. Misra and J. P. Shukla, *J. Indian Chem. Soc.* 1951, 28, 277), $^1$H-NMR (200 MHz, CDCl$_3$) d 10.35 (CHO), 2-(3-cyanophenyl)benzaldehyde starting from 3-bromobenzonitrile, $^1$H-NMR (200 MHz, CDCl$_3$) d 9.95 (CHO).

2-(5-fluoro-2-methylphenyl)benzaldehyde starting from 2-bromo-4-fluorotoluene, $^1$H-NMR (200 MHz, CDCl$_3$) d 9.92 (CHO).

2-(4-methylphenyl)benzaldehyde starting from 4-bromotoluene, $^1$H-NMR (200 MHz, CDCl$_3$) d 10.00 (CHO).

2-(3-trifluoromethylphenyl)benzaldehyde starting from 3-bromobenzotrifluoride, $^1$H-NMR (200 MHz, CDCl$_3$) d 9.96 (CHO).

2-(4-fluorophenyl)benzaldehyde starting from 4-fluorobromobenzene, $^1$H-NMR (200 MHz, CDCl$_3$) d 9.98 (CHO).

2-(2-fluorophenyl)benzaldehyde starting from 1-bromo-2-fluorobenzene, $^1$H-NMR (200 MHz, CDCl$_3$) d 9.91 (CHO).

2-(4-chloro-2-fluorophenyl)benzaldehyde starting from 1-bromo-4-chloro-2-fluorobenzene, $^1$H-NMR (200 MHz, CDCl$_3$) d 9.92 (CHO).

2-(5-chloro-2-methylphenyl)benzaldehyde staring from 2-bromo-4-chlorotoluene, $^1$H-NMR (200 MHz, CDCl$_3$) d 9.75 (CHO).

2-(3-chloro-2-methylphenyl)benzaldehyde staring from 2-bromo-5-chlorotoluene, $^1$H-NMR (200 MHz, CDCl$_3$) d 9.72 (CHO).

EXAMPLE 3

2-(benzoxazol-2-yl)benzaldehyde

A mixture of 12.5 g of 2-tributylstannylbenzoxazole (prepared by the method of P. Jutzi and W. Gilge, *J. Organometallic Chem.* 1983, 246, 159, using tributyltin chloride as a less toxic replacement for trimethyltin chloride) 5.66 g 2-bromobenzaldehyde, and 0.46 g tetrakis (triphenylphosphine)-palladium (0) in 300 ml of anhydrous xylene under a nitrogen atmosphere was heated to 115° C. for 12 h. The reaction mixture was cooled to room temperature and evaporated to dryness under reduced pressure. The resulting oil was purified by chromatography on silica eluting with ethyl acetate-heptane (1:5) to afford 5.8 g of 2-(benzoxazol-2-yl)benzaldehyde, GC-M.S. (E.I.) (M/Z): 223 [M$^+$].

In a similar manner was prepared:

2-(benzothiazol-2-yl)benzaldehyde starting from 2-tributylstannylbenzothiazole (prepared by the method of P. Jutzi and W. Gilge, *J. Organometallic Chem.* 1983, 246, 159, from benzothiazole, using tributyltin chloride as a less toxic replacement for trimethyltin chloride), melting at 117–120° C.

EXAMPLE 4

2-(benzo[b]furan-2-yl)benzaldehyde

A mixture of 3 g of benzo[b]furan-2-boronic acid, 3.14 g 2-bromobenzaldehyde, 0.56 g tetrakis(triphenylphosphine)-palladium (0), and 17 ml of 2N aqueous sodium carbonate in 50 ml of a 9:1 mixture of toluene-ethanol, under a nitrogen atmosphere, was heated to 100° C. for 10 h. The mixture was cooled to room temperature, diluted with 100 ml of methylene chloride and washed with 50 ml of 5% sodium bicarbonate containing 5 ml of 0.880 ammonia. The organic layer was dried over sodium sulfate and evaporated to dryness under reduced pressure to give 2-(benzo[b]furan-2-yl)benzaldehyde as a brown gum, GC-M.S. (E.I.) (M/Z): 222 [M$^+$].

In a similar manner were prepared:
2-(benzo[b]thiophen-2-yl)benzaldehyde starting from 2,4,6-tri(2-benzo[b]thienyl)cyclotriboroxane (prepared by the method of R. P. Dickinson and B. Iddon *J. Chem. Soc.* (C), 1970, 1926), $^1$H-NMR (200 MHz, CDCl$_3$) d 10.25 (CHO),
2-(5-fluorobenzo[b]thiophen-2-yl)benzaldehyde starting from 2,4,6-tri(2-(5-fluorobenzo[b]thienyl)) cyclotriboroxane (prepared by the method of R. P. Dickinson and B. Iddon *J. Chem. Soc.* (C), 1970, 1926), itself prepared from 5-fluorobenzo[b]thiophene (prepared by the method of B Février, G Dupas, J Bourguignon and G Quéguiner, *J. Heterocyclic Chem.*, 1983, 30, 1085), $^1$H-NMR (200 MHz, CDCl$_3$) d 10.24 (CHO),
2-(5-chlorobenzofuran-2-yl)benzaldehyde starting from 5-chlorobenzofuran-2-boronic acid (prepared by the method of R. P. Dickinson and B. Iddon *J. Chem. Soc.* (C) 1970, 1926), itself prepared from 5-chlorobenzo[b]furan (prepared by the method of T. Ota, S. Hasegawa, S Inoue and K. Sato, *J. Chem. Soc. Perkin Trans. I*, 1988, 3029), $^1$H-NMR (200 MHz, CDCl$_3$) d 10.36 (CHO).

EXAMPLE 5

2-(3a,4,5,6,7,7a-Hexahydro-7a-pyrrolidino-1,2-benzisoxazol-3-yl)-bromobenzene

To a stirred solution of 6.3 g of 2-bromobenzohydroximinoyl chloride (A. Q. Hussein, M. M. El-Abadelah, W. S. Sabri, *J. Heterocycl. Chem.*, 1983, 20, 301) in 100 ml methylene chloride at room temperature was added 9.4 g of 1-pyrrolidinocyclohexene (prepared by the method of M. E. Kuehne, *J. Am. Chem. Soc.*, 1959, 81, 5400) dropwise with external cooling. The solution was stirred for 19 h then evaporated and 150 ml of water was added and the suspension extracted with two 200 ml portions of methylene chloride. The combined organic layers were washed with 100 ml of brine and evaporated to an oil. To this oil was added 35 ml of methanol and the crystalline product filtered off to yield 5 g of 2-(3a,4,5,6,7,7a-hexahydro-7a-pyrrolidino-1,2-benzisoxazol-3-yl)-bromobenzene melting at 134° C.

In a similar manner were prepared:
2-bromo-(5-phenylisoxazol-3-yl)benzene starting from a-bromostyrene; $^1$H-NMR (400 MHz, CDCl$_3$) d 6.96 (CHCN).
2-bromo-(5-methylisoxazol-3-yl)benzene starting from 2-bromopropene; $^1$H-NMR (400 MHz, CDCl$_3$) d 2.51 (Me).
2-bromo-(isoxazol-3-yl)benzene starting from vinylbromide; $^1$H-NMR (400 MHz, CDCl$_3$) d 6.97 (CHCN).

EXAMPLE 6

2-(4,5,6,7-Tetrahydro-1,2-benzisoxazol-3-yl)-bromobenzene

To a stirred solution of 5.8 g of 2-(3a,4,5,6,7,7a-hexahydro-7a-pyrrolidino1,2-benzisoxazol-3-yl)-bromobenzene in 60 ml of methanol was added 100 ml of concentrated hydrochloric acid and the solution was refluxed for 20 min. The solution was cooled to room temperature and neutralised with 10M potassium hydroxide solution. The solution was extracted with 400 ml then 200 ml of methylene chloride and the combined organic layers were dried over sodium sulfate and evaporated to yield 4.5 g of 2-(4,5,6,7-tetrahydro1,2-benzisoxazol-3-yl)-bromobenzene as a gum, GC-M.S. (E.I.) (MIZ): 277 [M]$^+$.

EXAMPLE 7

2-(4,5,6,7-Tetrahydro-1,2-benzisoxazol-3-yl)-benzaldehyde

To a solution of 4.1 g of 2-(4,5,6,7-tetrahydro-1,2-benzisoxazol-3-yl)-bromobenzene in 100 ml of ether at a temperature of −40° C. was added 11 ml of a 1.5M solution of butyllithium in hexane with magnetic stirring. The reaction was warmed to −20° C. and held at this temperature for 5 minutes. The lithio species was quenched by the addition of 1.3 ml of N,N-dimethylformamide. To the reaction was added 100 ml of saturated ammonium chloride and the solution was extracted with two 200 ml portions of ether. The combined organic layers were dried over sodium sulfate and evaporated to yield 3.5 g of 2-(4,5,6,7-tetrahydro-1,2-benzisoxazol-3-yl)-benzaldehyde, GC-M.S. (E.I.) (M/Z): 226 [M−H]$^+$.

In a similar manner were prepared:
2-(5-phenyl isoxazol-3-yl)benzaldehyde, starting from 2-bromo-(5-phenylisoxazol-3-yl)benzene melting at 90–97° C.,
2-(5-methylisoxazol-3-yl)benzaldehyde, starting from 2-bromo-(5-methylisoxazol-3-yl)benzene; $^1$H-NMR (400 MHz, CDCl$_3$) d 2.54 (Me).
2-(isoxazol-3-yl)benzaldehyde, starting from 2-bromo-(isoxazol-3-yl)benzene; $^1$H-NMR (400 MHz, CDCl$_3$) d 6.63 (CHCN).

EXAMPLE 8

2-formylbenzaldehyde diethylacetal

To a solution of 10.4 g of 2-bromobenzaldehyde diethyl acetal in 200 ml of dry diethyl ether at −65° C. was added 27.5 ml of a 1.6 M solution of butyllithium in hexanes. The solution was stirred at this temperature for 30 min. then slowly warmed to −40° C. when 3.4 ml of dimethylformamide was added dropwise. The reaction was warmed to room temperature then 100 ml of water was added and the organic layer was separated. The aqueous layer was extracted with two 100 ml portions of ether and the combined organic extracts were dried over sodium sulfate and evaporated to give 8.5 g of 2-formylbenzaldehyde diethylacetal as an oil; ; $^1$H-NMR (200 MHz, CDCl$_3$) d 5.06 (CHOEt).

EXAMPLE 9

(2-fluoropyridin-3-yl)-2-(diethoxymethyl)-phenylmethanol

To a solution of 2.5 ml of diisopropylamine in 20 ml of dry tetrahydrofuran at −78° C. was added 11 ml of a 1.6 M solution of butyllithium in hexanes. The solution was stirred for 20 min. then a solution of 1.15 g of 2-fluoropyridine in 3 ml of tetrahydrofuran was added. The solution was stirred at −78° C. for 30 min then a solution of 2-formylbenzaldehyde diethylacetal in 3 ml of tetrahydrofuran was added dropwise. This solution was stirred for 1 h then warmed to room temperature overnight. The reaction was poured into a 5% solution of sodium carbonate and extracted with two 300 ml portions of ether. The combined organic layers were washed with 300 ml of water then the same volume of brine and dried over sodium sulfate. Evaporation of the solvent afforded (2-fluoropyridin-3-yl)-2-(diethoxymethyl)-phenyl methanol as a viscous oil; $^1$H-NMR (200 MHz, CDCl$_3$) d 5.60 (CHOEt).

In a similar manner were prepared:
(3-fluoropyridin-4-yl)-2-(diethoxymethyl)-phenylmethanol starting from 3-fluoropyridine; $^1$H-NMR (200 MHz, CDCl$_3$) d 5.58 (CHOEt).
(4-chloropyridin-3-yl)-2-(diethoxymethyl)-phenylmethanol starting from 4-chloropyridine; $^1$H-NMR (200 MHz, CDCl$_3$) d 5.63 (CHOEt).

EXAMPLE 10

(2-fluoropyridin-3-yl)-2-(diethoxymethyl)-phenylmethanone

To a stirred suspension of 11.8 g of dicalite in 100 ml of dry methylene chloride was added 7.38 g of chromium trioxide. The suspension was stirred for 30 min then a solution of (2-fluoropyridin-3-yl)-2-(diethoxymethyl)-phenylmethanol in 100 ml of methylene chloride was added. The supension was stirred overnight. The suspension was filtered through dicalite and washed with methylene chloride. The filtrate was washed with 100 ml portions of 1 M sodium hydroxide solution, water and brine and evaporated and azeotroped with toluene. Flash chromatography eluting with 30 to 50% ethyl acetate in heptane afforded (2-fluoropyridin-3-yl)-2-(diethoxymethyl)-phenylmethanone as a gum; $^1$H-NMR (200 MHz, CDCl$_3$) d 5.60 (CHOEt), In a similar manner were prepared:
(3-fluoropyridin-4-yl)-2-(diethoxymethyl)-phenylmethane starting from (3-fluoropyridin-4-yl)-2-(diethoxymethyl)-phenylmethanol; $^1$H-NMR (200 MHz, CDCl$_3$) d 5.75 (CHOEt),
(4-chloropyridin-3-yl)-2-(diethoxymethyl)-phenylmethane starting from (4-chloropyridin-3-yl)-2-(diethoxymethyl)-phenylmethanol; $^1$H-NMR (200 MHz, CDCl$_3$) d 5.84 (CHOEt).

EXAMPLE 11

2-(Isoxazolo[5,4-b]pyridin-3-yl)-benzaldehyde

To a solution of 0.49 g of acetone oxime in 8 ml of dry tetrahydrofuran was added 0.75 g of potassium tert-butoxide. The solution was stirred for 15 min. then a solution of 1.86 g of (2-fluoropyridin-3-yl)-2-(diethoxymethyl)-phenylmethanone in 8 ml of tetrahydrofuran was added. The solution was stirred at room temperature for 30 min. then quenched by the addition of 25 ml of a 1:1 water-saturated ammonium chloride solution. The solution was extracted with two 50 ml portions of ether and the combined ether extracts were washed with brine and dried over sodium sulfate. Evaporation afforded the intermediate 3-[2-(diethyloxymethyl)-benzoyl]-2-[((isopropylidene)amino] oxy]-pyridine which was not characterised but dissolved in 30 ml of ethanol and 20 ml of 2 M hydrochloric acid added and the solution refluxed for 15 min. The solution was cooled to room temperature and the crystals of 2-(isoxazolo [5,4-b]pyridin-3-yl)-benzaldehyde were collected by filtration and dried in vacuo, $^1$H-NMR (200 MHz, CDCl$_3$) d 10.26 (CHO).

In a similar manner were prepared:
2-(Isoxazolo[5,4-c]pyridin-3-yl)-benzaldehyde starting from (3-chloropyridin-4-yl)-2-(diethoxymethyl)-phenylmethane; m.p 169–179° C.,
2-(Isoxazolo[4,5-c]pyridin-3-yl)-benzaldehyde starting from (4-chloropyridin-3-yl)-2-(diethoxymethyl)-phenylmethane; $^1$H-NMR (200 MHz, CDCl$_3$) d 10.26 (CHO).

EXAMPLE 12

3-Bromo-2-(diethoxymethyl)-benzo[b]furan

To a solution of 2.6 g of 3-bromo-2-benzo[b] furancarboxaldehyde (see M. Cugnon de Sevricourt and M. Robba, Bull. Chim. Soc. Fr., 1977, 142) in 2.7 ml of triethyl orthoformate was added 33 mg of para-toluene sulfonic acid and the solution stirred at at room temperature overnight. The solution was diluted with a 5% sodium carbonate solution and extracted with ether. The ether extracts were dried over sodium sulfate and evaporated to give 3-bromo-2-(diethoxymethyl)-benzo[b]furan as a liquid; $^1$H-NMR (200 MHz, CDCl$_3$) d 5.76 (CHOEt).

In a similar manner was prepared:
3-Bromo-4-(diethoxymethyl)-thiophene, starting from 4-bromo-3-thiophenecarboxaldehyde (prepared by the method of D. W. Hawkins, B. Iddon, D. S. Longthorne and P. J. Rosyk, J. Chem. Soc., Perkin Trans. 1, 1994, 2735), $^1$H-NMR (200 MHz, CDCl$_3$) d 5.52 (CHOEt).

EXAMPLE 13

2-(Diethoxymethyl)-3-(2-fluorobenzoyl)-benzo[b] furan

To a solution of 3 g of 3-bromo-2-(diethoxymethyl)-benzo[b]furan in 80 ml of dry ether under nitrogen at −100° C was added 17.4 ml of a 1.7 M solution of tert-butyllithium in hexanes. The solution was stirred at the low temperature for 2 h then a solution of 2.76 g of N-methoxy-N-methyl-2-fluorobenzamide in 20 ml of dry ether was added and the solution stirred at the low tempertature for 10 min. The solution was then allowed to slowly warm to 0° C., water was added and the organic layer was separated, washed with water and dried over sodium sulfate and evaporated. Gravity chromatography eluting 0 to 50% toluene in heptane afforded 0.91 g of 2-(diethoxymethyl)-3-(2-fluorobenzoyl)-benzo[b]furan as an oil, $^1$H-NMR (200 MHz, CDCl$_3$) d 5.76 (CHOEt).

In a similar manner were prepared:
2-(Diethoxymethyl)-5-(2-fluorobenzoyl)-thiophene, starting from 2-bromo-5-(diethoxymethyl)-thiophene (see D. J. Chadwick, J. Chambers, P. K. Hodgson, G. D, Meakins and R. L. Snowden, J. Chem. Soc., Perkin Trans. 1, 1994, 2735), $^1$H-NMR (200 MHz, CDCl$_3$) d 5.75 (CHOEt),
2-(diethoxymethyl)-4-(2-fluorobenzoyl)-thiophene, starting from 3-bromo-5-(diethoxymethyl)-thiophene (see D. J. Chadwick, J. Chambers, P. K. Hodgson, G. D, Meakins and R. L. Snowden, J. Chem. Soc., Perkin Trans. 1, 1994, 2735), $^1$H-NMR (200 MHz, CDCl$_3$) d 5.72 (CHOEt),
3-(diethoxymethyl)-4-(2-fluorobenzoyl)-thiophene, starting from 3-bromo-4-(diethoxymethyl)-thiophene, $^1$H-NMR (200 MHz, CDCl$_3$) d 6.04 (CHOEt).

2-(diethoxymethyl)-3-(2-fluorobenzoyl)-thiophene, starting from 3-bromo-2-(diethoxymethyl)-thiophene (see D. J. Chadwick, J. Chambers, P. K. Hodgson, G. D, Meakins and R. L. Snowden, *J. Chem. Soc., Perkin Trans.* 1, 1994, 2735), 1H-NMR (200 MHz, CDCl3) d 6.13 (CHOEt), 2-(diethoxymethyl)-3-(2-fluorobenzoyl)-furan, starting from 3-bromo-2-(diethoxymethyl)-furan (see D. J. Chadwick, J. Chambers, P. K. Hodgson, G. D, Meakins and R. L. Snowden, *J. Chem. Soc., Perkin Trans.* 1, 1994, 2735), 1H-NMR (200 MHz, CDCl3) d 5.90 (CHOEt).

EXAMPLE 14

3-(1,2-Benzisoxazol -3-yl)-2-benzo[b] furancarboxaldehyde

To a solution of 0.21 g of acetone oxime in 10 ml of dry tetrahydrofuran was added 0.32 g of potassium tert-butoxide and the suspension was stirred for 1 h. To this suspension was added a solution of 0.9 g of 2-(diethoxymethyl)-3-(2-fluorobenzoyl)-benzo[b]furan in 10 ml of tetrahydrofuran. The resulting solution was refluxed for 4.5 h then cooled to room temperature and brine added. The mixture was extracted with ether and the organic extracts were washed with water and dried over sodium sulfate. Evaporation afforded the crude 0.99 g of crude O-[2-[2-(diethoxymethyl)-3-benzo[b]furanoyl]phenyl]oxime-2-propanone which was not characterised but dissolved in 10 ml of ethanol and 10 ml of 2 M hydrochloric acid added. The mixture was refluxed for 3 h the cooled to room temperature and and the precipitate collected and recrystallised from methylene chloride-ether to give 0.11 g of 3-(benzisoxazol-3-yl)-2-thiophenecarboxaldehyde melting at 173–174° C.

In a similar manner were prepared:
5-(1,2-Benzisoxazol-3-yl)-2-thiophenecarboxaldehyde, starting from 2-(diethoxymethyl)-5-(2-fluorobenzoyl)-thiophene, melting at 179–182° C.,
4-(1,2-benzisoxazol-3-yl)-2-thiophenecarboxaldehyde, starting from 2-(diethoxymethyl)-4-(2-fluorobenzoyl)-thiophene, melting at 152–155° C.,
4-(1,2-benzisoxazol-3-yl)-3-thiophenecarboxaldehyde, starting from 3-(diethoxymethyl)-4-(2-fluorobenzoyl)-thiophene, melting at 150–153° C.,
3-(1,2-benzisoxazol-3-yl)-2-thiophenecarboxaldehyde, starting from 2-(diethoxymethyl)-3-(2-fluorobenzoyl)-thiophene, melting at 154.5–155.5° C.,
3-(1,2-benzisoxazol-3-yl)-2-furancarboxaldehyde, starting from 2-(diethoxymethyl)-3-(2-fluorobenzoyl)-furan, melting at 191–192° C.

EXAMPLE 15

2-(benzo[b]furan-2-yl)-a-2-propenyl-benzenemethanamine hydrochloride

To a solution of 3.0 g of 2-(benzo[b]furan-2-yl)-benzaldehyde in 60 ml of tetrahydrofuran, cooled at 0° C. under a nitrogen atmosphere, was added 16.2 ml of a 1 M solution of lithium bis(trimethylsilyl)amine in hexane. After stirring at 0° C. for 20 min 16.2 ml of a 1 M solution of allylmagnesium bromide in tetrahydrofuran was added and the resulting solution stirred at 0° C. for 40 min, then allowed to warm to room temperature over 1 h. Saturated aqueous ammonium chloride was added and the mixture was extracted with dichloromethane. The combined organic layers were dried over sodium sulfate and evaporated to dryness under reduced pressure to give a brown oil. The compound was purified by chromatography on silica gel, eluting with 5% methanol in dichloromethane. The pure compound was dissolved in methanol and converted to its hydrochloride salt by addition of a solution of hydrogen chloride in methanol and crystallisation was initiated by addition of diethyl ether. The crystallised salt was filtered affording 2.4 g of 2-(benzo[b]furan-2-yl)-a-2-propenyl-benzenemethanamine hydrochloride, melting at 225–227° C.

In a similar way were prepared:
(1) 2-(benzo[b]thiophen-3-yl)-a-2-propenyl-benzenemethanamine (Z)-butenedioate, starting from 2-(benzo[b]thiophen-3-yl)-benzaldehyde, melting at 185–187° C.,
(2) 2-(napth-2-yl)-a-2-propenyl-benzenemethanamine (Z)-butenedioate, starting from 2-(napth-2-yl)benzaldehyde, melting at 182–185° C.,
(3) 2-(benzo[b]furan-3-yl)-a-2-propenyl-benzenemethanamine hydrochloride, starting from 2-(benzo[b]furan-3-yl)benzaldehyde, melting at 160–165° C.,
(4) 2-phenyl-a-2-propenyl-benzenemethanamine hydrochloride, starting from 2-phenylbenzaldehyde, melting at 214–218° C.,
(5) 2-(2-methoxyphenyl)-a-2-propenyl-benzenemethanamine hydrochloride, starting from 2-(2-methoxyphenyl)benzaldehyde, melting at 236–240° C.,
(6) 2-(napth-1-yl)-a-2-propenyl-benzenemethanamine hydrochloride, starting from 2-(napth-1-yl)benzaldehyde, melting at 102–107° C.,
(7) 2-(thien-3-yl)-a-2-propenyl-benzenemethanamine (E)-butenedioate, starting from 2-(thien-3-yl)benzaldehyde, melting at 196–198° C.,
(8) 2-(thien-2-yl)-a-2-propenyl-benzenemethanamine (E)-butenedioate, starting from 2-(thien-2-yl)benzaldehyde, melting at 196–197° C.,
(9) 2-(4-pyrolinylphenyl)-a-2-propenyl-benzenemethanamine (E)-butenedioate, starting from 2-(4-pyrolinylphenyl)benzaldehyde, melting at 213–215° C.,
(10) 2-(4-phenyl-3-fluorophenyl)-a-2-propenyl-benzenemethanamine (E)-butenedioate, starting from 2-(4-phenyl-3-fluorophenyl)benzaldehyde, melting at 205–208° C.,
(11) 2-(furan-3-yl)-a-2-propenyl-benzenemethanamine (E)-butenedioate, starting from 2-(furan-3-yl)benzaldehyde, melting at 183–185° C.
(12) 2-benzyl-a-2-propenyl-benzenemethanamine (E)-butenedioate, starting from 2-benzylbenzaldehyde, melting at 181–183° C.,
(13) 2-(2-chlorophenyl)-a-2-propenyl-benzenemethanamine (E)-butenedioate, starting from 2-(2-chlorophenyl)benzaldehyde, melting at 189–191° C.,
(14) 2-(5-chlorothien-2-yl)-a-2-propenyl-benzenemethanamine (E)-butenedioate, starting from 2-(5-chlorothien-2-yl)benzaldehyde, melting at 192–199° C.,
(15) 2-(2-fluoro-4-methylphenyl)-a-2-propenyl-benzenemethanamine (E)-butenedioate, starting from 2-(2-fluoro-4-methylphenyl)benzaldehyde, melting at 209–211° C.,
(16) 2-(3-fluoro-4-methylphenyl)-a-2-propenyl-benzenemethanamine (E)-butenedioate, starting from 2-(3-fluoro-4-methylphenyl)benzaldehyde, melting at 194–196° C.,
(17) 2-(3-fluoro-4-chlorophenyl)-a-2-propenyl-benzenemethanamine (E)-butenedioate, starting from 2-(3-fluoro-4-chlorophenyl)benzaldehyde, melting at 192–194° C.,

(18) 2-(3-methoxybenzyl)-a-2-propenyl-benzenemethanamine (E)-butenedioate, starting from 2-(3-methoxybenzyl)benzaldehyde, melting at 163–165° C.,

(19) 2-(2-methoxybenzyl)-a-2-propenyl-benzenemethanamine (E)-butenedioate, starting from 2-(2-methoxybenzyl)benzaldehyde, melting at 172–174° C.,

(20) 2-(benzoxazol-2-yl)-a-2-propenyl-benzenemethanamine (E)-butenedioate, starting from 2-(benzoxazol-2-yl)benzaldehyde, melting at 202–204° C.,

(21) 2-(benzothiazol-2-yl)-a-2-propenyl-benzenemethanamine hydrochloride, starting from 2-(benzothiazol-2-yl)benzaldehyde, melting at 240–242° C.,

(22) 2-(benzo[b]thiophen-2-yl)-a-2-propenyl-benzenemethanamine hydrochloride, starting from 2-(benzo[b]thiophen-2-yl)benzaldehyde, melting at 106–108° C.,

(23) 2-(5-fluorobenzo[b]thiophen-2-yl)-a-2-propenyl-benzenemethanamine hydrochloride, starting from 2-(5-fluorobenzo[b]thiophen-2-yl)benzaldehyde, melting at 104–106° C.,

(24) 2-(5-chlorobenzofuran-2-yl) -a-2-propenyl-benzenemethanamine hydrochloride, starting from 2-(5-chlorobenzofuran-2-yl)benzaldehyde, melting at 226–228° C.,

(25) 2-(4,5,6,7-tetrahydro-1,2-benzisoxazol-3-yl)-a-2-propenyl-benzenemethanamine (Z)-butenedioate starting from 2-(4,5,6,7-tetrahydro1,2-benzisoxazol-3-yl)-benzaldehyde, melting at 144–145° C.,

(26) 2-(1,2-benzisoxazol-3-yl)-a-2-propenyl-2-thiophenemethanamine (E)-butenedioate starting from 3-(benzisoxazol-3-yl)-2-thiophenecarboxaldehyde, melting at 173–178° C.,

(27) 2-(1,2-benzisoxazol-3-yl)-a-2-propenyl-2-furanmethanamine (E)-butenedioate starting from 3-(1,2-benzisoxazol-3-yl)-2-furancarboxaldehyde, melting at 158–165° C.,

(28) 4-(1,2-benzisoxazol-3-yl)-a-2-propenyl-2-thiophenemethanamine (E)-butenedioate starting from 4-(1,2-benzisoxazol-3-yl)-2-thiophenecarboxaldehyde, melting at 161–164° C.,

(29) 5-(1,2-benzisoxazol-3-yl)-a-2-propenyl-2-thiophenemethanamine (E)-butenedioate starting from 5-(1,2-benzisoxazol-3-yl)-2-thiophenecarboxaldehyde, melting at 182–189° C.,

(30) 4-(1,2-benzisoxazol-3-yl)-a-2-propenyl-3-thiophenemethanamine (E)-butenedioate (2:1 salt) starting from 4-(1,2-benzisoxazol-3-yl)-3-thiophenecarboxaldehyde, melting at 188–190° C.,

(31) 3-(1,2-benzisoxazol-3-yl)-a-2-propenyl-2-benzo[b]furanmethanamine (E)-butenedioate starting from 3-(1,2-benzisoxazol-3-yl)-2-benzo[b]furancarboxaldehyde, melting at 210–216° C.

(32) 2-(5-fluoro-2-methylphenyl)-a-2-propenyl-benzenemethanamine (E)-butenedioate starting from 2-(5-fluoro-2-methylphenyl)benzaldehyde, melting at 190–192° C.

(33) 2-(4-methylphenyl)-a-2-propenyl-benzenemethanamine (E)-butenedioate starting from 2-(4-methylphenyl)benzaldehyde, melting at 198–200° C.

(34) 2-(3-trifluoromethylphenyl)-a-2-propenyl-benzenemethanamine (E)-butenedioate starting from 2-(3-trifluoromethylphenyl)benzaldehyde, melting at 194–196° C.

(35) 2-(4-fluorophenyl)-a-2-propenyl-benzenemethanamine (E)-butenedioate starting from 2-(4-fluorophenyl)benzaldehyde, melting at 201–203° C.

(36) 2-(2-fluorophenyl)-a-2-propenyl-benzenemethanamine (E)-butenedioate starting from 2-(2-fluorophenyl)benzaldehyde melting at 225–226° C.

(37) 2-(4-chloro-2-fluorophenyl)-a-2-propenyl-benzenemethanamine (E)-butenedioate starting from 2-(4-chloro-2-fluorophenyl)benzaldehyde, melting at 213–215° C.

(38) 2-(5-chloro-2-methylphenyl)-a-2-propenyl-benzenemethanamine (E)-butenedioate starting from 2-(5-chloro-2-methylphenyl)benzaldehyde, melting at 179–184° C.

(39) 2-(3-chloro-2-methylphenyl)-a-2-propenyl-benzenemethanamine (E)-butenedioate staring from 2-(3-chloro-2-methylphenyl)benzaldehyde, melting at 192–196° C.

(40) 2-(5-phenylisoxazol-3-yl)-a-2-propenyl-benzenemethanamine (E)-butenedioate, starting from 2-(5-phenylisoxazol-3-yl)benzaldehyde, melting at 165–180° C.,

(41) 2-(5-methylisoxazol-3-yl)-a-2-propenyl-benzenemethanamine (Z)-butenedioate, starting from 2-(5-methylisoxazol-3-yl)benzaldehyde, melting at 130–138° C.,

EXAMPLE 16

2-(3,5-dimethylisozazol-4-yl)-a-2-propenyl-benzenemethanamine (E)-butenedioate

To a stirred suspension of 1 g of 2-(3,5-dimethylisozazol-4-yl)benzaldehyde and 2.4 g of anhydrous magnesium sulfate was added 0.86 ml of diphenylmethanamine, and the stirring continued overnight. The reaction was filtered through dicalite and the filtrate evaporated to give an oil that crystallised on addition of diethyl ether and cooling to 4° C., to give 1.55 g of N-[2-(3,5-dimethylisoxazol4-yl)-benzylidene]-1,1-diphenylmethanamine, melting at 165–167° C. A stirred solution of 0.81 g of N-[2-(3,5-dimethylisoxazol-4-yl)-benzylidene]-1,1-diphenylmethanamine in 15 ml of tetrahydrofuran was cooled to −78° C. and 6.6 ml of a 1 M solution of potassium tert-butoxide in tetrahydrofuran was added dropwise. The purple coloured solution was stirred for 15 min then 0.57 ml of allyl bromide was added rapidly and the reaction allowed to slowly warm to room temperature. The reaction mixture was diluted with 25 ml of saturated aqueous ammonium chloride and extracted into dichloromethane. The combined organic extracts were dried over sodium sulfate then evaporated to give crude N-(diphenylmethylidene)-2-(3,5-dimethylisozazol-4-yl)-a-2-propenyl-benzenemethanamine which was not characterised due to instability. The crude product was dissolved in 15 ml of acetone and 5 ml of 1 M hydrochloric acid added. The solution was stirred overnight and then the acetone was removed by evaporation and the crude product was redissolved in 20 ml of dichloromethane. The solution was extracted with two 20 ml portions of 2N hydrochloric acid. The combined acid extracts were washed with 10 ml of dichloromethane and then basified with 4N sodium hydroxide solution. The basic extracts were combined and re-extracted with three 20 ml portions of dichloromethane, the combined organic extracts were dried over sodium sulfate and evaporated to give 153 mg of product. The product was dissolved in 1 ml of methanol and 73 mg of fumaric acid was added. The product was crystallised by trituration with ether and cooling to 4° C. to yield 167 mg of 2-(3,5-dimethylisozazol-4-yl)-a-2-propenyl-benzenemethanamine (E)-butenedioate, melting at 198–200° C.

In a similar manner were prepared:
(1) 2-(quinolin-3-yl)-a-2-propenyl-benzenemethanamine (E)-butenedioate, starting from 2-(quinolin-3-yl)-benzaldehyde, melting at 194–197° C.,
(2) 2-(isoquinolin-4-yl)-a-2-propenyl-benzenemethanamine (E)-butenedioate, starting from 2-(isoquinolin-4-yl)-benzaldehyde, melting at 246–248° C.,
(3) 2-(pyrimidin-3-yl)-a-2-propenyl-benzenemethanamine (E)-butenedioate, starting from 2-(pyrimidin-3-yl) benzaldehyde, melting at 75–77° C.,
(4) 2-(thiazol-2-yl)-a-2-propenyl-benzenemethanamine (E)-butenedioate, starting from 2-(thiazol-2-yl)benzaldehyde, melting at 156–161° C.
(5) 2-(isoxazolo[5,4-b]pyridin-3-yl)-a-2-propenyl-benzenemethanamine (Z)-butenedioate starting from 2-(isoxazolo[5,4-b]pyridin-3-yl)-benzaldehyde, melting at 187–188° C. (dec),
(6) 2-(isoxazolo[5,4-c]pyridin-3-yl)-a-2-propenyl-benzenemethanamine (E)-butenedioate starting from 2-(isoxazolo[5,4-c]pyridin-3-yl)-benzaldehyde, melting at 183–189° C.,
(7) 2-(isoxazolo[4,5-c]pyridin-3-yl)-a-2-propenyl-benzenemethanamine (Z)-butenedioate starting from 2-(isoxazolo[4,5-c]pyridin-3-yl)-benzaldehyde, melting at 151–153° C.,
(8) 2-(isoxazol-3-yl)-a-2-propenyl-benzenemethanamine (E)-butenedioate, starting from 2-(isoxazol-3-yl) benzaldehyde, melting at 150–175° C.,

EXAMPLE 17

2-(3-cyanophenyl)-a-2-propynyl-benzenemethanamine

To a stirred suspension of 3.58 g of 2-(3-cyanobenzyl) benzaldehyde and 10.4 g of anhydrous magnesium sulfate was added 3.6 ml of diphenylmethanamine, and the stirring continued overnight. The reaction was filtered through dicalite and the filtrate evaporated to give an oil that crystallised on addition of diethyl ether and cooling to 4° C., to give 4.11 g of N-[2-(3-cyanobenzyl)benzylidene]-1,1-diphenylmethanamine, melting at 113–115° C. A stirred solution of 1.0 g of N-[2-(3-cyanobenzyl)benzylidene]-1,1-diphenylmethanamine in 15 ml of tetrahydrofuran was cooled to −78° C. and 6.7 ml of a 1 M solution of potassium tert-butoxide in tetrahydrofuran was added dropwise. The purple coloured solution was stirred for 20 min then 0.9 ml of propargyl bromide was added rapidly and the reaction allowed to slowly warm to room temperature. The reaction mixture was diluted with 25 ml of saturated aqueous ammonium chloride and extracted into dichloromethane. The combined organic extracts were dried over sodium sulfate the evaporated to give crude N-(diphenylmethylidene)-2-(3-cyanobenzyl)-a-2-propynyl-benzenemethanamine which was not characterised due to instability. The crude product was dissolved in 20 ml of acetone and 5 ml of 1 M hydrochloric acid added. The solution was stirred at room temperature for 3 h then cooled to 4° C. overnight. The acetone was removed by evaporation and the crude product redissolved in 20 ml of dichloromethane. The solution was extracted with two 20 ml portions of 2N hydrochloric acid. The combined acid extracts were washed with 10 ml of dichloromethane and then basified with 4N sodium hydroxide solution. The basic extracts were combined and re-extracted with three 20 ml portions of dichloromethane, the combined organic extracts were dried over sodium sulfate and evaporated to give 120 mg of product. The product was dissolved in 1 ml of methanol and 57 mg of fumaric acid was added. The product was crystallised by trituration with ether and cooling to 4° C. to yield 120 mg of 2-(3-cyanobenzyl)-a-2-propynyl-benzenemethanamine (E)-butenedioate, melting at 182–184° C.

In a similar manner was prepared:
2-(isoxazolo[5,4-b]pyridin-3-yl)-a-2-propynyl-benzenemethanamine (Z)-butenedioate starting from 2-(isoxazolo[5,4-b]pyridin-3-yl)-benzaldehyde, melting at 180–185° C. (dec).

EXAMPLE 18

[2-(2-Dimethoxyethyl)-phenyl](2-fluorophenyl)-methanone

A stirred solution of 10.0 g of 2-(2-bromophenyl) acetaldehyde dimethylacetal (B. Wünsch, Arch. Pharm. (Weinheim) 1990, 323, 493) in 100 ml of anhydrous tetrahydrofuran was cooled to −78° C. under a nitrogen atmosphere. To this solution was added 29.3 ml of a 1.6 M solution of n-butyllithium in hexane. The solution was warmed to 30° C. over 30 min during which time a precipitate formed. The suspension was re-cooled to −78° C. and a solution of 7.46 g of N-methoxy-N-methyl-2-fluorobenzamide in 100 ml of tetrahydrofuran was added by cannular. The solution was warmed to room temperature and stirred for 1 h, then quenched by the addition of 100 ml of water and extracted with 300 ml then 200 ml of dichloromethane. The combined organic extracts were dried over sodium sulfate and evaporated to yield crude product which was purified by chromatography on silica gel, eluting with 15% ethyl acetate in hexane, affording 6.81 g of [2-(2-dimethoxyethyl)-phenyl](2-fluorophenyl)-methanone, $^1$H-NMR (200 MHz, CDCl$_3$) d 3.29 (CH$_3$).

EXAMPLE 19

2-[2-(1,2-benzisoxazol-3-yl)-phenyl] acetaldehyde

To a solution of 1.91 g of acetone oxime in 40 ml of tetrahydrofuran was added 2.93 g of potassium tert-butoxide. The suspension was stirred for 30 min then a solution of 6.81 g of [2-(2-dimethoxyethyl)-phenyl](2-fluorophenyl)-methanone in 30 ml of tetrahydrofuran was added and the solution was heated to reflux for 12 h. The solution was cooled to room temperature and diluted with 100 ml of water then extracted with 200 ml then 100 ml of ethyl acetate. The combined organic extracts were washed with 100 ml of brine then dried over sodium sulfate and evaporated to give 7.91 g of crude O-[2-(2-dimethoxyethyl) benzoyl-2-phenyl]-oxime 2-propanone. This material was dissolved in 90 ml of ethanol and 90 ml of 2N hydrochloric acid was added. The resulting mixture was heated to reflux for 3 h. After cooling to room temperature most of the organic solvent was removed by evaporation and the residual aqueous solution was extracted with 200 ml then 100 ml of dichloromethane. The combined organic extracts were washed with 100 ml of brine then dried over sodium sulfate, and evaporated to give 6.9 g of a mixture of the desired product and its corresponding diethyl acetal. This material was redissolved in 30 ml of chloroform and cooled to 0° C. To this solution was added 10 ml of a 50% aqueous solution of trifluoroacetic acid and the resulting mixture stirred at 0° C. for 3 h then at room temperature for 12 h. The reaction was quenched by adding 100 ml of water and the aqueous solution was extracted with 200 ml then 100 ml of dichloromethane. The combined organic extracts were washed with 100 ml of 5% sodium carbonate solution then dried over sodium sulfate and evaporated to give 5.5 g of crude 2-[2-(1,2-benzisoxazol-3-yl)-phenyl] acetaldehyde, $^1$H-NMR (200 MHz, CDCl$_3$) d 9.75 (CHO).

EXAMPLE 20

3-[2-(2-Hydroxy-4-pentenyl)phenyl]-1,2-benzisoxazole

To a stirred solution of 2 g of 2-[2-(1,2-benzisoxazol-3-yl)-phenyl] acetaldehyde in 50 ml of tetrahydrofuran at −78° C. under a nitrogen atmosphere was added 10 ml of a 1 M solution of allyl magnesium bromide in diethyl ether. The solution was warmed to room temperature and stirred for a further 2 h then quenched by addition of 50 ml of saturated aqueous ammonium chloride. The aqueous layer was extracted with 150 ml then 100 ml of dichloromethane and the combined organic extracts dried over sodium sulfate and evaporated to give crude product which was purified by chromatography eluting with 20% ethyl acetate in hexane, affording 1 g of 3-[2-(2-Hydroxy-4-pentenyl)phenyl]-1,2-benzisoxazole, $^1$H-NMR (200 MHz, CDCl$_3$) d 5.8 (CH=CH$_2$).

EXAMPLE 21

3-[2-(2-Azido-4-pentenyl)phenyl]-1,2-benzisoxazole

To a stirred solution of 1.0 g of 3-[2-(2-Hydroxy-4-pentyl)phenyl]-1,2-benzisoxazole and 1.0 g of triphenylphosphine in 20 ml of tetrahydrofuran at 0° C. was added 0.56 ml of diethyl azodicarboxylate followed by dropwise addition of 1.36 ml of diphenylphosphoryl azide. The solution was stirred at 0° C. for 1 h then warmed to room temperature and stirred a further 2 h. The reaction was quenched with 50 ml of water and extracted with 100 ml then 50 ml of dichloromethane. The combined organic fractions were dried over sodium sulfate and evaporated to give crude product, which was purified by chromatography on silica gel eluting with 7% ethyl acetate in hexane, affording 0.65 g of 3-[2-(2-Azido-4-pentenyl)phenyl]-1,2-benzisoxazole, $^1$H-NMR (200 MHz, CDCl$_3$) d 5.68 (CH=CH$_2$).

EXAMPLE 22

3-[2-(2-Amino-4-pentenyl)phenyl]-1,2-benzisoxazole (E)-butenedioate

To a stirred solution of 631 mg of 3-[2-(2-azido-4-pentenyl)phenyl]-1,2-benzisoxazole in 10 ml of anhydrous tetrahydrofuran at −40° C. under a nitrogen atmosphere was added 2.07 ml of a 1 M solution of lithium aluminium hydride in diethyl ether. The reaction mixture was warmed to room temperature then heated to 60° C. for 1 h. After cooling to room temperature and careful quenching with 4 N sodium hydroxide, 50 ml of water was added and the product extracted with 100 ml then 50 ml of dichloromethane. The combined organic extracts were dried over sodium sulfate and the solvent removed by evaporation to give crude product which was purified by chromatography on silica gel eluting with 10% methanol in dichloromethane, to give 315 mg of 3-[2-(2-amino-4-pentenyl)phenyl]-1,2-benzisoxazole. The product was dissolved in 1 ml of methanol and 131 mg of fumaric acid was added. Addition of diethyl ether and cooling to 4° C. led to crystallisation of 313 mg of 3-[2-(2-amino-4-pentenyl)phenyl]-1,2-benzisoxazole (E)-edioate, melting at 170–172° C.

We claim:

1. A compound of formula (I)

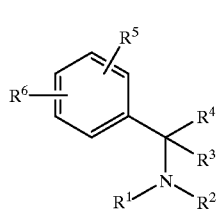

(I)

wherein $R^1$ and $R^2$, which may be the same or different, are each selected from $C_{6-12}$aryl, $C_{2-14}$heteroaryl, $C_{6-12}$aryl$C_{1-6}$alkyl, $C_{2-14}$heteroaryl$C_{1-6}$alkyl (where the alkyl, aryl or heteroaryl moiety may be optionally substituted by one or more substituents selected from $C_{1-6}$alkoxy, $C_{1-6}$alkyl, $C_{3-6}$cycloalkyl, $C_{4-6}$cycloalkenyl, $C_{6-12}$aryl, $C_{2-14}$heteroaryl, halogen, amino, hydroxy, halo$C_{1-6}$alkyl, nitro, $C_{1-6}$alkylthio, sulphonamide, $C_{1-6}$alkylsulphonyl, hydroxy-$C_{1-6}$alkyl, $C_{1-6}$alkoxycarbonyl, carboxyl, carboxy$C_{1-6}$alkyl, carboxamide and $C_{1-6}$alkylcarboxamide), hydrogen, $C_{1-6}$alkyl, $C_{3-6}$cycloalkyl, $C_{4-6}$cycloalkenyl, $C_{2-6}$alkenyl, $C_{2-6}$alkynyl and $C_{1-6}$alkoxy$C_{1-6}$alkyl (where the alkyl, cycloalkyl, cycloalkenyl, alkenyl, alkynyl, or alkoxyalkyl moieties may be optionally substituted by one or more substituents selected from amino, halogen, hydroxy, $C_{1-6}$alkylcarboxamide, carboxamide, carboxy, $C_{1-6}$alkoxycarbonyl, $C_{1-6}$alkylcarboxy and carboxy$C_{1-6}$alkyl) or one of $R^1$ and $R^2$ are as hereinbefore defined and one is hydroxy;

$R^3$ and $R^4$, which may be the same or different, are each selected from $C_{6-12}$aryl, $C_{2-14}$heteroaryl, $C_{6-12}$aryl$C_{1-6}$alkyl, $C_{2-14}$heteroaryl$C_{1-6}$alkyl (where the alkyl, aryl or heteroaryl moiety may be optionally substituted by one or more substituents selected from $C_{1-6}$alkoxy, $C_{1-6}$alkyl, $C_{3-6}$cycloalkyl, $C_{4-6}$cycloalkenyl, $C_{6-12}$aryl, $C_{2-14}$heteroaryl, halogen, amino, hydroxy, halo$C_{1-6}$alkyl, nitro, $C_{1-6}$alkylthio, sulphonamide, $C_{1-6}$alkylsulphonyl, hydroxy$C_{1-6}$alkyl, $C_{1-6}$alkoxycarbonyl, carboxyl, carboxy$C_{1-6}$alkyl, $C_{1-6}$alkylcarboxamide and carboxamide), hydrogen, $C_{1-6}$alkyl, $C_{3-6}$cycloalkyl, $C_{3-6}$cycloalkyl$C_{1-6}$alkyl, $C_{4-6}$cycloalkenyl, $C_{2-6}$alkenyl, $C_{2-6}$alkynyl, $C_{1-6}$alkoxy-$C_{1-6}$alkyl, halo $C_{1-6}$alkyl, halo$C_{2-6}$alkenyl, halo$C_{2-6}$alkynyl, cyano, carboxyl, $C_{1-6}$alkylcarboxy and carboxy$C_{1-6}$alkyl (where the alkyl, cycloalkyl, cycloalkenyl, alkenyl, alkynyl, or alkoxyalkyl moieties may be optionally substituted by one or more substituents selected from amino, hydroxy, $C_{1-6}$alkylcarboxamide, carboxamide, carboxy, $C_{1-6}$alkoxycarbonyl, $C_{1-6}$alkylcarboxy and carboxy$C_{1-6}$alkyl); or one of $R^3$ or $R^4$ together with one of $R^1$ or $R^2$ and the N atom to which it is attached form a 5- or 6-membered heterocyclic ring.

$R^5$ represents one or more ring substituents selected from halogen, hydrogen, $C_{1-6}$alkyl and $C_{1-6}$alkoxy; and R⁶ represents a single ring substituent of formula:

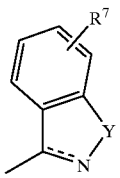

wherein the dotted line represents a bond; Y is oxygen or
—NR⁸

(where R⁸ is hydrogen or $C_{1-6}$alkyl) and R⁷ represents one or more substituents selected from hydrogen, halogen, halo$C_{1-6}$alkyl, $C_{1-6}$alkyl and $C_{1-6}$alkoxy; or a pharmaceutically acceptable salt or solvate thereof.

2. A compound according to claim 1 wherein R¹ and R², which may be the same or different, are each independently selected from $C_{6-12}$aryl, $C_{2-14}$heteroaryl, $C_{6-12}$aryl$C_{1-6}$alkyl, $C_{2-14}$heteroaryl$C_{1-6}$alkyl (where the alkyl, aryl or heteroaryl moiety may be optionally substituted by one or more substituents selected from $C_{1-6}$alkoxy, $C_{1-6}$alkyl, $C_{3-6}$cycloalkyl, $C_{4-6}$cycloalkenyl, $C_{6-12}$aryl, $C_{2-14}$heteroaryl, halogen, amino, hydroxy, halo$C_{1-6}$alkyl, nitro, $C_{1-6}$alkylthio, sulphonamide, $C_{1-6}$alkylsulphonyl, hydroxy$C_{1-6}$alkyl, carboxyl, carboxy$C_{1-6}$alkyl, carboxamide and $C_{1-6}$alkylcarboxamide), hydrogen, $C_{1-6}$alkyl, $C_{3-6}$cycloalkyl, $C_{4-6}$cycloalkenyl, $C_{2-6}$alkenyl, $C_{2-6}$alkynyl and $C_{1-6}$alkoxy$C_{1-6}$alkyl (where the alkyl, cycloalkyl, cycloalkenyl, alkynyl, or alkoxyalkyl moieties may be optionally substituted by one or more substituents selected from amino, hydroxy, $C_{1-6}$alkylcarboxamide, carboxamide, carboxy and carboxy$C_{1-6}$alkyl) or one of R¹ and R² are as hereinbefore defined and one is hydroxy;

R³ and R⁴, which may be the same or different, are each independently selected from $C_{6-12}$aryl, $C_{2-14}$heteroaryl, $C_{6-12}$aryl$C_{1-6}$alkyl, $C_{2-14}$heteroaryl-$C_{1-6}$alkyl (where the alkyl, aryl or heteroaryl moiety may be optionally substituted by one or more substituents selected from $C_{1-6}$alkoxy, $C_{1-6}$alkyl, $C_{3-6}$cycloalkyl, $C_{4-6}$cycloalkenyl, $C_{6-12}$aryl, $C_{214}$heteroaryl, halogen, amino, hydroxy, halo$C_{1-6}$alkyl, nitro, $C_{1-6}$alkylthio, sulphonamide, $C_{1-6}$alkylsulphonyl, carboxamide and $C_{1-6}$alkylcarboxamide), hydrogen, $C_{1-6}$alkyl, $C_{3-6}$cycloalkyl, $C_{4-6}$cycloalkenyl, $C_{2-6}$alkenyl, $C_{2-6}$alkynyl, $C_{1-6}$alkoxy$C_{1-6}$alkyl, cyano, carboxyl and carboxy$C_{1-6}$alkyl;

R⁵ represents one or more ring substituents selected from halogen, hydrogen, $C_{1-6}$alkyl and $C_{1-6}$alkoxy; and R⁶ represents a single ring substituent of formula:

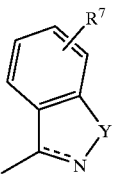

wherein the dotted line represents a bond; Y is oxygen or
—NR⁸ (where R⁸ is hydrogen or $C_{1-6}$alkyl) and R⁷ is hydrogen, halogen, $C_{1-6}$alkyl or $C_{1-6}$alkoxy; or a pharmaceutically acceptable salt or solvate thereof.

3. A compound according to claim 1 wherein one of R¹ and R² is hydrogen and the other is $C_{6-12}$aryl$C_{1-6}$alkyl (where the alkyl or aryl moiety may be optionally substituted by one or more ring substituents selected from $C_{1-6}$alkoxy and $C_{2-14}$heteroaryl); R³, R⁴ and R⁵ are hydrogen, Y is oxygen, the dotted line represents a bond and R⁷ is hydrogen or halogen; or a pharmaceutically acceptable salt or solvate thereof.

4. A compound of formula (I) according to claim 1, wherein R¹ and R² are both hydrogen; one of R³ and R⁴ is hydrogen and the other is $C_{1-6}$alkyl, $C_{2-6}$alkenyl, $C_{2-6}$alkynyl, $C_{1-6}$alkoxy$C_{1-6}$alkyl or $C_{6-12}$arylalkyl R⁵ is hydrogen, Y is oxygen or —NCH₃, the dotted line represents a bond and R⁷ is hydrogen or halogen; or a pharmaceutically acceptable salt or solvate thereof.

5. A compound according to claim 1 selected from:
2-(1,2-Benzisoxazol-3-yl)-benzenemethanamine;
2-(1,2-Benzisoxazol-3-yl)-α-2-propenyl-benzenemethanamine;
(R)-(+)-2-(1,2-Benzisoxazol-3-yl)-α-2-propenyl-benzenemethanamine;
(S)-(−)-2-(1,2-Benzisoxazol-3-yl)-α-2-propenyl-benzenemethanamine;
2-(1,2-Benzisoxazol-3-yl)-α-butyl-benzenemethanamine;
2-(1,2-Benzisoxazol-3-yl)-α-2-propynyl-benzenemethanamine;
2-(1-Methyl-1H-indazol-3-yl)-α-2-propenyl-benzenemethanamine;
(−)-2-(6-chloro-1,2-benzisoxazol-3-yl)-a-2-propynyl-benzenemethanamine; and
(S )-(−)-2-(6-chloro-1,2-benzisoxazol-3-yl)-a-2-propenyl-benzenemethanamine;
or pharmaceutically acceptable salt or solvate thereof.

6. A pharmaceutical formulation comprising a compound of formula (I) or a pharmaceutically acceptable salt or solvate thereof, as defined according to claim 1, together with a pharmaceutically acceptable carrier thereof.

7. A method for the treatment of a psychiatric disorder in an animal, which comprises administering to said animal an effective amount of a compound according to claim 1.

8. A method according to claim 7, wherein the psychiatric disorder is depression, anxiety or psychosis.

* * * * *